United States Patent
Arrington et al.

(10) Patent No.: US 7,101,884 B2
(45) Date of Patent: Sep. 5, 2006

(54) TYROSINE KINASE INHIBITORS

(75) Inventors: Kenneth L. Arrington, Elkins Park, PA (US); Mark E. Fraley, North Wales, PA (US); Barbara Hanney, North Wales, PA (US); Yuntae Kim, Harleysville, PA (US); Keith L. Spencer, Hatfield, PA (US)

(73) Assignee: Merck & Co., Inc., Rahway, NJ (US)

( * ) Notice: Subject to any disclaimer, the term of this patent is extended or adjusted under 35 U.S.C. 154(b) by 105 days.

(21) Appl. No.: 10/489,594

(22) PCT Filed: Sep. 10, 2002

(86) PCT No.: PCT/US02/28779

§ 371 (c)(1),
(2), (4) Date: Mar. 12, 2004

(87) PCT Pub. No.: WO03/024969

PCT Pub. Date: Mar. 27, 2003

(65) Prior Publication Data

US 2005/0070546 A1    Mar. 31, 2005

Related U.S. Application Data

(60) Provisional application No. 60/322,075, filed on Sep. 14, 2001.

(51) Int. Cl.
*C07D 403/04* (2006.01)
*C07D 403/14* (2006.01)
*A61K 31/416* (2006.01)
*A61K 31/4162* (2006.01)

(52) U.S. Cl. ............ 514/249; 514/259.1; 514/303; 514/403; 544/262; 544/350; 546/118; 548/361.1

(58) Field of Classification Search ............ 544/262, 544/350; 546/118; 548/361.1; 514/258, 514/249, 303, 403, 259.1
See application file for complete search history.

(56) References Cited

U.S. PATENT DOCUMENTS

| 6,245,759 B1 | 6/2001 | Bilodeau et al. |
| 6,306,874 B1 | 10/2001 | Fraley et al. |
| 6,313,138 B1 | 11/2001 | Fraley et al. |
| 6,479,512 B1 | 11/2002 | Fraley et al. |

FOREIGN PATENT DOCUMENTS

| WO | WO 01/02369 | 1/2001 |
| WO | WO 03/037252 | 5/2003 |

OTHER PUBLICATIONS

See Satoh et al. Arthritis Rheum. 44(2): 260-265, 2001.*
J. Rak et al. Cancer Research, 55:4575-4580, 1995.
G. Gasparini and A.L. Harris, J. Clin. Oncol., 1995, 13:765-782.
M. Toi et al., Japan. J. Cancer Res., 1994, 85:1045-1049.
A.J. Dickinson et al., Br. J. Urol., 1994, 74:762-766.
L.M. Ellis et al., Surgery, 1996, 120(5):871-878.
J.K. Williams et al., Am. J. Surg., 1994, 168:373-380.
A. Amirkhosravi et al., Platelets, 10:285-292 (1999).
S.P. Gunningham, et al., Can. Research, 61: 3206-3211 (2001).
A. Giatromanolaki et al., J. Pathol. 2001: 194:101-108.
Michael Detmar, J. Dermatological Sci., 24 Suppl. 1, S78-S84 (2000).
Hasegawa et al., Skeletal Radiol., vol. 28, pp. 41-45, 1999.
Brockelsby et al., Laboratory Investigation 79:1101-1111 (Sep. 1999).
Paul et al., Nature Med 7:222-227 (2001).
Matsuyama et al., J. Neurol. Sci. 186:75-79 (2001).
van der Flier et al., J. Infectious Diseases, 183:149-153 (2001).
Stephen K. Smith, Trends in Endocrinology & Metabolism, vol. 12, No. 4, pp. 147-151, May/Jun. 2001.
Levis et al., Blood, vol. 98, No. 3, pp. 885-887 (2001).
Rajesh K. Jain, Nature Medicine, vol. 7. No. 9, pp. 987-989 (Sep. 2001).
Giulio Jori, Lasers Med. Sci., 1990; 5: 115-120.
Chuannong Zhou, J. Photochem. and Photobiol. 1989; 3: 299-318.
Hendrich et al., Knee Surg Sports Traumatol Arthroscopy 5: 58-63 (1997).
Hall et al., Am J Hum Genet 61:785-789, 1997.
Li et al., Gene Therapy, 1998; 5:1105-13.
Fathallah-Shaykh et al., J Immunol 2000; 164:217-222.
Dougherty et al., J. Natl. Cancer Inst., 1998, 90(12): 889-905.
Van Bruggen et al., J. Clin. Invest,. 104:1613-1620 (1999).
Gerber et al., Nature Medicine, vol. 5, No. 6, pp. 623-628, 1999.
David A. Greenberg, Drug News Perspect 11(5):265-270 (1998).
Nakagawa et al., FEBS Let. 473:161-164 (2000).
Peter Traxler, Exp. Opin. Ther. Patents 8 (12) 1599-1625(1998).
Peter M. Traxler, Exp. Opin. Ther. Patents 7(6) 571-588 (1997).
Joseph V. Simone, Cecil Textbook of Medicine 20th Edition, vol. 1, pp. 1004-1010 (1996).
Lawrence et al., Pub Med Abstract, vol. 77(2), pp. 81-114 (1998).
Rocca, et al., Tetrahedron, 49:49-64 (1993).
O'Neil, et al., J. Med. Chem., 40:437 (1997).
Villemin, D. and Goussu, D., Heterocycles 29:1255 (1989).

* cited by examiner

*Primary Examiner*—Venkataraman Balasubramanian
(74) *Attorney, Agent, or Firm*—Dianne Brown; Matthew A. Leff; Mark R. Daniel

(57) ABSTRACT

The present invention relates to compounds which inhibit, regulate and/or modulate tyrosine kinase signal transduction, compositions which contain these compounds, and methods of using them to treat tyrosine kinase-dependent diseases and conditions, such as angiogenesis, cancer, tumor growth, atherosclerosis, age related macular degeneration, diabetic retinopathy, inflammatory diseases, and the like in mammals.

12 Claims, No Drawings

TYROSINE KINASE INHIBITORS

DOMESTIC PRIORITY CLAIM

This application is the National Stage of International Application No. PCT/US02/28779 filed on Sep. 10, 2002, which claims the benefit of U.S. Provisional Application No. 60/322,075, filed on Sep. 14, 2001.

BACKGROUND OF THE INVENTION

The present invention relates to compounds which inhibit, regulate and/or modulate tyrosine kinase signal transduction, compositions which contain these compounds, and methods of using them to treat tyrosine kinase-dependent diseases and conditions, such as angiogenesis, cancer, tumor growth, atherosclerosis, age related macular degeneration, diabetic retinopathy, inflammatory diseases, and the like in mammals.

Tyrosine kinases are a class of enzymes that catalyze the transfer of the terminal phosphate of adenosine triphosphate to tyrosine residues in protein substrates, as described in U.S. Pat. No. 6,245,759 B1 (hereby incorporated by reference).

Angiogenesis is characterized by excessive activity of vascular endothelial growth factor (VEGF) (as described in U.S. Pat. No. 6,245,759 B1). KDR mediates the mitogenic function of VEGF whereas Flt-1 appears to modulate non-mitogenic functions such as those associated with cellular adhesion. Inhibiting KDR thus modulates the level of mitogenic VEGF activity. In fact, tumor growth has been shown to be susceptible to the antiangiogenic effects of VEGF receptor antagonists. (Kim et al., Nature 362, pp. 841–844, 1993).

Solid tumors can therefore be treated by tyrosine kinase inhibitors since these tumors depend on angiogenesis for the formation of the blood vessels necessary to support their growth. These solid tumors include histiocytic lymphoma, cancers of the brain, genitourinary tract, lymphatic system, stomach, larynx and lung, including lung adenocarcinoma and small cell lung cancer. Additional examples include cancers in which overexpression or activation of Raf-activating oncogenes (e.g., K-ras, erb-B) is observed. Such cancers include pancreatic and breast carcinoma. Accordingly, inhibitors of these tyrosine kinases are useful for the prevention and treatment of proliferative diseases dependent on these enzymes.

The angiogenic activity of VEGF is not limited to tumors. VEGF accounts for most of the angiogenic activity produced in or near the retina in diabetic retinopathy. This vascular growth in the retina leads to visual degeneration culminating in blindness. Ocular VEGF mRNA and protein are elevated by conditions such as retinal vein occlusion in primates and decreased $pO_2$ levels in mice that lead to neovascularization. Intraocular injections of anti-VEGF monoclonal antibodies or VEGF receptor immunofusions inhibit ocular neovascularization in both primate and rodent models. Regardless of the cause of induction of VEGF in human diabetic retinopathy, inhibition of ocular VEGF is useful in treating the disease.

Expression of VEGF is also significantly increased in hypoxic regions of animal and human tumors adjacent to areas of necrosis. VEGF is also upregulated by the expression of the oncogenes ras, raf, src and mutant p53 (all of which are relevant to targeting cancer). Monoclonal anti-VEGF antibodies inhibit the growth of human tumors in nude mice. Although these same tumor cells continue to express VEGF in culture, the antibodies do not diminish their mitotic rate. Thus tumor-derived VEGF does not function as an autocrine mitogenic factor. Therefore, VEGF contributes to tumor growth in vivo by promoting angiogenesis through its paracrine vascular endothelial cell chemotactic and mitogenic activities. These monoclonal antibodies also inhibit the growth of typically less well vascularized human colon cancers in athymic mice and decrease the number of tumors arising from inoculated cells.

Inhibition of KDR or Flt-1 is implicated in pathological angiogenesis, and these receptors are useful in the treatment of diseases in which angiogenesis is part of the overall pathology, e.g., inflammation, diabetic retinal vascularization, as well as various forms of cancer since tumor growth is known to be dependent on angiogenesis. (Weidner et al., N. Engl. J. Med., 324, pp. 1–8, 1991).

SUMMARY OF THE INVENTION

The present invention relates to indolylindazole compounds that are capable of inhibiting, modulating and/or regulating signal transduction of both receptor-type and non-receptor type tyrosine kinases.

DETAILED DESCRIPTION OF THE INVENTION

The compounds of this invention are useful in the inhibition of kinases and are illustrated by a compound of Formula I:

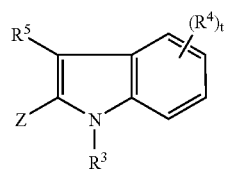

or a pharmaceutically acceptable salt or stereoisomer thereof, wherein

Z is 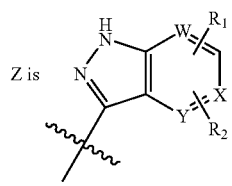

W is N or C;
X=Y is C=N, N=C, or C=C;
a is 0 or 1;
b is 0 or 1;
m is 0, 1, or 2;
t is 1, 2, or 3;
$R^1$, $R^2$ and $R^5$ are independently selected from:
1) H,
2) $(C=O)_aO_bC_1–C_{10}$ alkyl,
3) $(C=O)_aO_b$aryl,
4) $(C=O)_aO_bC_2–C_{10}$ alkenyl,
5) $(C=O)_aO_bC_2–C_{10}$ alkynyl,
6) $CO_2H$,
7) halo, 8) OH,
9) $O_bC_1$–$C_6$ perfluoroalkyl,
10) $(C=O)_aNR^7R^8$,
11) CN,
12) $(C=O)_aO_bC_3$–$C_8$ cycloalkyl,
13) $(C=O)_aO_b$heterocyclyl,
14) $SO_2NR^7R^8$, and
15) $SO_2C_1$–$C_{10}$ alkyl, said alkyl, aryl, alkenyl, alkynyl, cycloalkyl, and heterocyclyl is optionally substituted with one or more substituents selected from $R^6$;

$R^3$ is selected from:
1) H,
2) $(C=O)O_aC_1$–$C_6$ alkyl,
3) $(C=O)O_a$aryl,
4) $C_1$–$C_6$ alkyl,
5) $SO_2R^a$, and
6) aryl;

$R^4$ is selected from:
1) $(C=O)_aO_bC_1$–$C_{10}$ alkyl,
2) $(C=O)_aO_b$aryl,
3) $(C=O)_aO_bC_2$–$C_{10}$ alkenyl,
4) $(C=O)_aO_bC_2$–$C_{10}$ alkynyl,
5) $CO_2H$,
6) halo,
7) OH,
8) $O_bC_1$–$C_6$ perfluoroalkyl,
9) $(C=O)_aNR^7R^8$,
10) CN,
11) $(C=O)_aO_bC_3$–$C_8$ cycloalkyl,
12) $(C=O)_aO_b$heterocyclyl,
13) $SO_2NR^7R^8$, and
14) $SO_2C_1$–$C_{10}$ alkyl, said alkyl, aryl, alkenyl, alkynyl, cycloalkyl, and heterocyclyl is optionally substituted with one or more substituents selected from $R^6$;

$R^6$ is:
1) $(C=O)_aO_bC_1$–$C_{10}$ alkyl,
2) $(C=O)_aO_b$aryl,
3) $C_2$–$C_{10}$ alkenyl,
4) $C_2$–$C_{10}$ alkynyl,
5) $(C=O)_aO_b$ heterocyclyl,
6) $CO_2H$,
7) halo,
8) CN,
9) OH,
10) $O_bC_1$–$C_6$ perfluoroalkyl,
11) $O_a(C=O)_bNR^7R^8$,
12) oxo,
13) CHO,
14) $(N=O)R^7R^8$, or
15) $(C=O)_aO_bC_3$–$C_8$ cycloalkyl, said alkyl, aryl, alkenyl, alkynyl, heterocyclyl, and cycloalkyl optionally substituted with one or more substituents selected from $R^{6a}$;

$R^{6a}$ is selected from:
1) $(C=O)_rO_s(C_1$–$C_{10})$alkyl, wherein r and s are independently 0 or 1,
2) $O_r(C_1$–$C_3)$perfluoroalkyl, wherein r is 0 or 1,
3) $(C_0$–$C_6)$alkylene-$S(O)_mR^a$, wherein m is 0, 1, or 2,
4) oxo,
5) OH,
6) halo,
7) CN,
8) $(C_2$–$C_{10})$alkenyl,
9) $(C_2$–$C_{10})$alkynyl,
10) $(C_3$–$C_6)$cycloalkyl,
11) $(C_0$–$C_6)$alkylene-aryl,
12) $(C_0$–$C_6)$alkylene-heterocyclyl,
13) $(C_0$–$C_6)$alkylene-$N(R^b)_2$,
14) $C(O)R^a$,
15) $(C_0$–$C_6)$alkylene-$CO_2R^a$,
16) $C(O)H$,
17) $(C_0$–$C_6)$alkylene-$CO_2H$, and
18) $C(O)N(R^b)_2$, said alkyl, alkenyl, alkynyl, cycloalkyl, aryl, and heterocyclyl is optionally substituted with up to three substituents selected from $R^b$, OH, $(C_1$–$C_6)$alkoxy, halogen, $CO_2H$, CN, $O(C=O)C_1$–$C_6$ alkyl, oxo, and $N(R^b)_2$;

$R^7$ and $R^8$ are independently selected from:
1) H,
2) $(C=O)O_bC_1$–$C_{10}$ alkyl,
3) $(C=O)O_bC_3$–$C_8$ cycloalkyl,
4) $(C=O)O_b$aryl,
5) $(C=O)O_b$heterocyclyl,
6) $C_1$–$C_{10}$ alkyl,
7) aryl,
8) $C_2$–$C_{10}$ alkenyl,
9) $C_2$–$C_{10}$ alkynyl,
10) heterocyclyl,
11) $C_3$–$C_8$ cycloalkyl,
12) $SO_2R^a$, and
13) $(C=O)NR^b_2$, said alkyl, cycloalkyl, aryl, heterocylyl, alkenyl, and alkynyl is optionally substituted with one or more substituents selected from $R^{6a}$, or $R^7$ and $R^8$ can be taken together with the nitrogen to which they are attached to form a monocyclic or bicyclic heterocycle with 5–7 members in each ring and optionally containing, in addition to the nitrogen, one or two additional heteroatoms selected from N, O and S, said monocylcic or bicyclic heterocycle optionally substituted with one or more substituents selected from $R^{6a}$;

$R^a$ is $(C_1$–$C_6)$alkyl, $(C_3$–$C_6)$cycloalkyl, aryl, or heterocyclyl; and $R^b$ is H, $(C_1$–$C_6)$alkyl, aryl, heterocyclyl, $(C_3$–$C_6)$cycloalkyl, $(C=O)OC_1$–$C_6$ alkyl, $(C=O)C_1$–$C_6$ alkyl or $S(O)_2R^a$.

A second embodiment of the invention is a compound of Formula I, or a pharmaceutically acceptable salt or stereoisomer thereof, wherein Z is 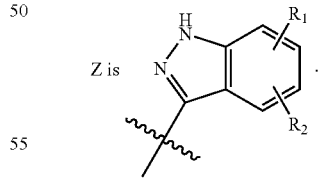.

A further embodiment of the present invention is illustrated by a compound of Formula I, or a pharmaceutically acceptable salt or stereoisomer thereof, with Z as defined immediately above, wherein a is 0 or 1;
b is 0 or 1; and
t is 1 or 2;

$R^1$, $R^2$ and $R^5$ are independently selected from:
1) H,
2) $(C=O)_aO_bC_1$–$C_6$ alkyl, 3) $(C=O)_aO_b$aryl,
4) $(C=O)_aO_bC_2$–$C_6$ alkenyl,
5) $(C=O)_aO_bC_2$–$C_6$ alkynyl,
6) $CO_2H$,
7) halo,
8) OH,
9) $O_bC_1$–$C_3$ perfluoroalkyl,
10) $(C=O)_aNR^7R^8$,
11) CN,
12) $(C=O)_aO_bC_3$–$C_6$ cycloalkyl,
13) $(C=O)_aO_b$heterocyclyl,
14) $SO_2NR^7R^8$, and
15) $SO_2C_1$–$C_6$ alkyl, said alkyl, aryl, alkenyl, alkynyl, cycloalkyl, and heterocyclyl is optionally substituted with one or more substituents selected from $R^6$;

$R^4$ is selected from:
1) $(C=O)_aO_bC_1$–$C_6$ alkyl,
2) $(C=O)_aO_b$aryl,
3) $(C=O)_aO_bC_2$–$C_6$ alkenyl,
4) $(C=O)_aO_bC_2$–$C_6$ alkynyl,
5) $CO_2H$,
6) halo,
7) OH,
8) $O_bC_1$–$C_3$ perfluoroalkyl,
9) $(C=O)_aNR^7R^8$,
10) CN,
11) $(C=O)_aO_bC_3$–$C_6$ cycloalkyl,
12) $(C=O)_aO_b$heterocyclyl,
13) $SO_2NR^7R^8$, and
14) $SO_2C_1$–$C_6$ alkyl, said alkyl, aryl, alkenyl, alkynyl, cycloalkyl, and heterocyclyl is optionally substituted with one or more substituents selected from $R^6$;

$R^6$ is:
1) $(C=O)_aO_bC_1$–$C_6$ alkyl,
2) $(C=O)_aO_b$aryl,
3) $C_2$–$C_6$ alkenyl,
4) $C_2$–$C_6$ alkynyl,
5) $(C=O)_aO_b$ heterocyclyl,
6) $CO_2H$,
7) halo,
8) CN,
9) OH,
10) $O_bC_1$–$C_3$ perfluoroalkyl,
11) $O_a(C=O)_bNR^7R^8$,
12) oxo,
13) CHO,
14) $(N=O)R^7R^8$, or
15) $(C=O)_aO_bC_3$–$C_6$ cycloalkyl, said alkyl, aryl, alkenyl, alkynyl, heterocyclyl, and cycloalkyl is optionally substituted with one or more substituents selcted from $R^{6a}$;

$R^{6a}$ is selected from:
1) $(C=O)_rO_s(C_1$–$C_6)$alkyl, wherein r and s are independently 0 or 1,
2) $O_r(C_1$–$C_3)$perfluoroalkyl, wherein r is 0 or 1,
3) $(C_0$–$C_6)$alkylene-$S(O)_mR^a$, wherein m is 0, 1, or 2,
4) oxo,
5) OH,
6) halo,
7) CN,
8) $(C_2$–$C_6)$alkenyl,
9) $(C_2$–$C_6)$alkynyl,
10) $(C_3$–$C_6)$cycloalkyl,
11) $(C_0$–$C_6)$alkylene-aryl,
12) $(C_0$–$C_6)$alkylene-heterocyclyl,
13) $(C_0$–$C_6)$alkylene-$N(R^b)_2$,
14) $C(O)R^a$,
15) $(C_0$–$C_6)$alkylene-$CO_2R^a$,
16) $C(O)H$, and
17) $(C_0$–$C_6)$alkylene-$CO_2H$, said alkyl, alkenyl, alkynyl, cycloalkyl, aryl, and heterocylyl is optionally substituted with up to three substituents selected from $R^b$, OH, $(C_1$–$C_6)$alkoxy, halogen, $CO_2H$, CN, $O(C=O)C_1$–$C_6$ alkyl, oxo, and $N(R^b)_2$; and $R^7$ and $R^8$ are independently selected from:
1) H,
2) $(C=O)O_bC_1$–$C_6$ alkyl,
3) $(C=O)O_bC_3$–$C_6$ cycloalkyl,
4) $(C=O)O_b$aryl,
5) $(C=O)O_b$heterocyclyl,
6) $C_1$–$C_6$ alkyl,
7) aryl,
8) $C_2$–$C_6$ alkenyl,
9) $C_2$–$C_6$ alkynyl,
10) heterocyclyl,
11) $C_3$–$C_6$ cycloalkyl,
12) $SO_2R^a$, and
13) $(C=O)NR^b{}_2$, said alkyl, cycloalkyl, aryl, heterocylyl, alkenyl, and alkynyl is optionally substituted with one or more substituents selected from $R6^a$, or $R^7$ and $R^8$ can be taken together with the nitrogen to which they are attached to form a monocyclic or bicyclic heterocycle with 5–7 members in each ring and optionally containing, in addition to the nitrogen, one or two additional heteroatoms selected from N, O and S, said monocylcic or bicyclic heterocycle optionally substituted with one or more substituents selected from $R^{6a}$;

$R^a$ is $(C_1$–$C_6)$alkyl, $(C_3$–$C_6)$cycloalkyl, aryl, or heterocyclyl; and $R^b$ is H, $(C_1$–$C_6)$alkyl, aryl, heterocyclyl, $(C_3$–$C_6)$cycloalkyl, $(C=O)OC_1$–$C_6$ alkyl, $(C=O)C_1$–$C_6$ alkyl or $S(O)_2R^a$.

Another embodiment is the compound described immediately above wherein $R^3$ and $R^5$ are further defined as H.

And yet another embodiment is wherein t is further defined as 1 and $R^1$ is selected from: H, halo, $(C_1$–$C_6)$alkyl, aryl, heterocyclyl, CN, $NH_2$, OH and $CO_2H$.

Also encompassed by the present invention is the compound of Formula I as further defined immediately above, or a pharmaceutically acceptable salt or stereoisomer thereof, and wherein $R^4$ is selected from:
1) $OC_1$–$C_6$ alkyleneNR$^7$R$^8$,
2) $(C=O)_aC_0$–$C_6$ alkylene-Q, wherein Q is H, OH, $CO_2H$, or $OC_1$–$C_6$ alkyl,
3) $OC_0$–$C_6$ alkylene-heterocyclyl, optionally substituted with one to three substituents selected from $R^{6a}$,
4) $C_0$–$C_6$ alkyleneNR$^7$R$^8$,
5) $(C=O)NR^7R^8$, and
6) $OC_1$–$C_3$ alkylene-$(C=O)NR^7R^8$, and
7) $SO_2NR^7R^8$.

Specific example of the compounds of the instant invention include:

6-Chloro-3-(1H-indol-2-yl)-1H-indazole
3-(1H-Indol-2-yl)-1H-indazole
3-(1H-Indol-2-yl)-1H-indazol-5-ylamine
3-(1H-Indol-2-yl)-6-methyl-1H-indazole
3-(1H-Indol-2-yl)4-chloro-1H-indazole
3-(1H-Indol-2-yl)-7-chloro-1H-indazole 3-(1H-Indol-2-yl)-4-fluoro-1H-indazole
3-(1H-Indol-2-yl)-5-fluoro-1H-indazole
3-(1H-Indol-2-yl)-5-methyl-1H-indazole
3-(1H-Indol-2-yl)-6-trifluoromethyl-1H-indazole
3-(1H-Indol-2-yl)-5,6-dimethyl-1H-indazole
3-(1H-Indol-2-yl)-1H-indazole-6-sulfonic acid amide
3-(1H-indol-2-yl)-1H-indazole-5-sulfonamide
3-(1H-Indol-2-yl)-6-bromo-1H-indazole
3-(1H-Indol-2-yl)-1H-indazole-6-carbonitrile
3-[5-(piperazin-1-ylsulfonyl)-1H-indol-2-yl]-1H-indazole
6-(2-Fluoro-pyridin-4-yl)-3(1H-indol-2-yl)-1H-indazole
4-[3-(1H-Indol-2-yl)-1H-indazol-6-yl]-1H-pyridin-2-one
3-(1H-Indol-2-yl)-6-(1-oxy-pyridin-3-yl)-1H-indazole
3-(1H-Indol-2-yl)-6-(1H-pyrrol-2-yl)-1H-indazole
3-(1H-Indol-2-yl)-6-(1H-pyrrol-3-yl)-1H-indazole
5-[3-(1H-Indol-2-yl)-1H-indazol-6-yl]-1H-pyridin-2-one
3-(1H-Indol-2-yl)-6-(1-oxy-pyridin-4-yl)-1H-indazole
3-(1H-Indol-2-yl)-6-(1H-tetrazol-5-yl)-1H-indazole
3-{5-[(4-methylpiperazin-1-yl)carbonyl]-1H-indol-2-yl}-1H-indazole
1-[2-(1H-Indazol-3-yl)-1H-indol-5-yl]-1-(4-methyl-piperazin-1-yl)-methanone
1-[2-(6-Chloro-1H-indazol-3-yl)-1H-indol-5-yl]-1-piperazin-1-yl-methanone
1-[2-(1H-Indazol-3-yl)-1H-indol-5-yl]-1-piperazin-1-yl-methanone
2-(6-Chloro-1H-indazol-3-yl)-1H-indole-5-sulfonic acid amide
Methyl [2-(6-chloro-1H-indazol-3-yl)-1H-indole-5-yl]sulfone
2-(6-Chloro-1H-indazol-3-yl)-7-fluoro-1H-indole-5-sulfonic acid amide
2-(6-Chloro-1H-indazol-3-yl)-6-fluoro-1H-indole-5-sulfonic acid amide
2-(6-Chloro-1H-indazol-3-yl)-4-fluoro-1H-indole-5-sulfonic acid amide
7-Chloro-2-(6-chloro-1H-indazol-3-yl)-1H-indole-5-sulfonic acid amide
2-(6-Chloro-5-fluoro-1H-indazol-3-yl)-1H-indole-5-sulfonic acid amide
2-(6-Chloro-1H-indazol-3-yl)-1H-indole-5-carboxylic acid methyl ester
2-(6-chloro-1H-indazol-3-yl)-1H-indole-5-carboxylic acid
6-Chloro-3-(5-fluoro-1H-indol-2-yl)-1H-indazole
6-Chloro-3-(5-methyl-1H-indol-2-yl)-1H-indazole
3-[5-(4-Methyl-piperazin-1-ylmethyl)-1H-indol-2-yl]-1H-indazole
3-[5-(4-Methanesulfonyl-piperazin-1-ylmethyl)-1H-indol-2-yl]-1H-indazole
6-Chloro-3-[5-(4-methanesulfonyl-piperazin-1-ylmethyl)-1H-indol-2-yl]-1H-indazole
6-Chloro-3-[5-(4-acetyl-piperazin-1-ylmethyl)-1H-indol-2-yl]-1H-indazole
1-[2-(6-Chloro-1H-indazol-3-yl)-1H-indol-5-ylmethyl]-4-methyl-[1,4]diazepan-5-one
1-{4-[2-(6-Chloro-1H-indazol-3-yl)-1H-indol-5-ylmethyl]-piperazin-1-yl}-2-hydroxy-ethanone
3-{4-[2-(6-Chloro-1H-indazol-3-yl)-1H-indol-5-ylmethyl]-piperazin-1-yl}-butyric acid
6-Chloro-3-[4-(4-methanesulfonyl-piperazin-1-ylmethyl)-1H-indol-2-yl]-1H-indazole
3-{4-[2-(6-Chloro-1H-indazol-3-yl)-1H-indol-4-ylmethyl]-piperazin-1-yl}-butyric acid and the pharmaceutically acceptable salts and optical isomers thereof.

A preferred embodiment is a compound selected from 2-(6-Chloro-1H-indazol-3-yl)-1H-indole-5-sulfonic acid amide (5-5)

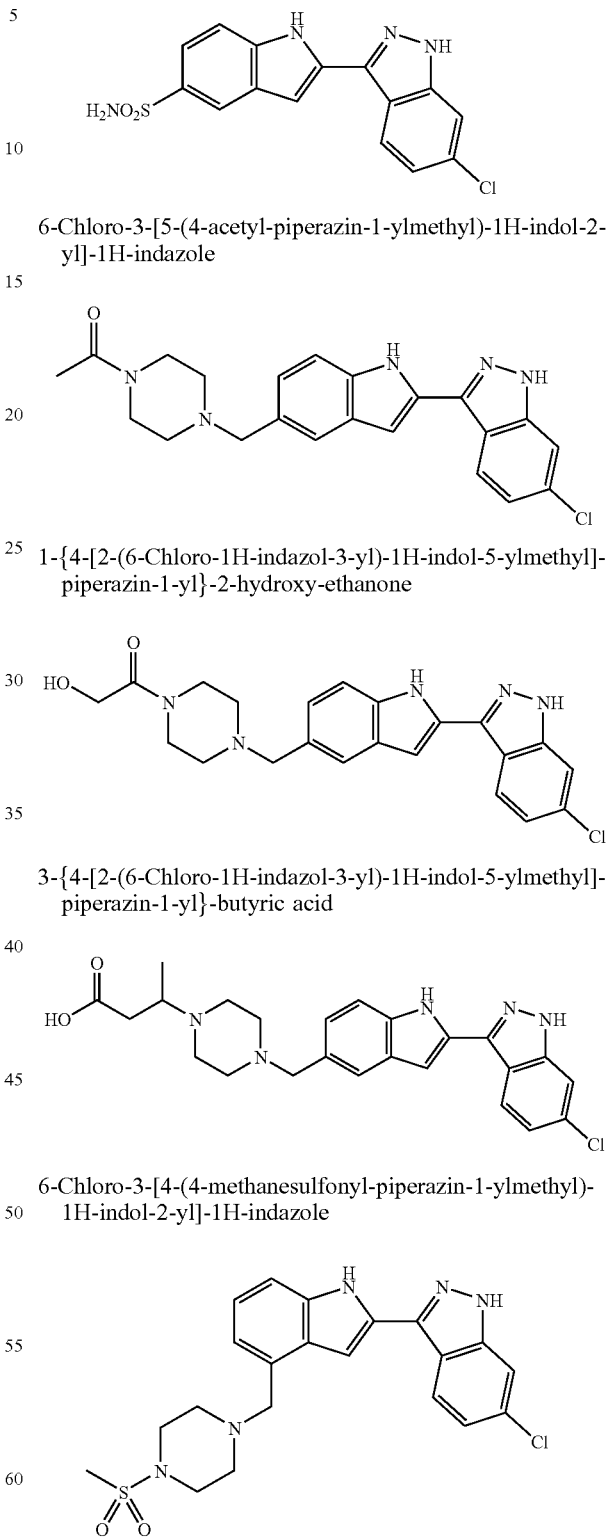

6-Chloro-3-[5-(4-acetyl-piperazin-1-ylmethyl)-1H-indol-2-yl]-1H-indazole

1-{4-[2-(6-Chloro-1H-indazol-3-yl)-1H-indol-5-ylmethyl]-piperazin-1-yl}-2-hydroxy-ethanone 3-{4-[2-(6-Chloro-1H-indazol-3-yl)-1H-indol-5-ylmethyl]-piperazin-1-yl}-butyric acid 6-Chloro-3-[4-(4-methanesulfonyl-piperazin-1-ylmethyl)-1H-indol-2-yl]-1H-indazole or a pharmaceutically acceptable salt or stereoisomer thereof.

The compounds of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119–1190), and occur as racemates, racemic mixtures, and as individual diastereomers, with all possible isomers and mixtures thereof, including optical isomers, being included in the present invention. In addition, the compounds disclosed herein may exist as tautomers and both tautomeric forms are intended to be encompassed by the scope of the invention, even though only one tautomeric structure is depicted. For example, any claim to compound A below is understood to include tautomeric structure B, and vice versa, as well as mixtures thereof.

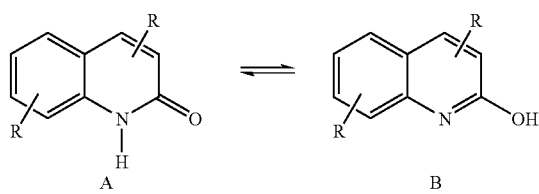

When any variable (e.g. $R^4$, $R^6$, $R^{6a}$, etc.) occurs more than one time in any constituent, its definition on each occurrence is independent at every other occurrence. Also, combinations of substituents and variables are permissible only if such combinations result in stable compounds. Lines drawn into the ring systems from substituents indicate that the indicated bond may be attached to any of the substitutable ring atoms. If the ring system is polycyclic, it is intended that the bond be attached to any of the suitable carbon atoms on the proximal ring only.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be taken to be equivalent to the phrase "optionally substituted with at least one substituent" and in such cases the preferred embodiment will have from zero to three substituents.

As used herein, "alkyl" is intended to include both branched and straight-chain saturated aliphatic hydrocarbon groups having the specified number of carbon atoms. For example, $C_1$–$C_{10}$, as in "$C_1$–$C_{10}$ alkyl" is defined to include groups having 1, 2, 3, 4, 5, 6, 7, 8, 9 or 10 carbons in a linear or branched arrangement. For example, "$C_1$–$C_{10}$ alkyl" specifically includes methyl, ethyl, n-propyl, i-propyl, n-butyl, t-butyl, i-butyl, pentyl, hexyl, heptyl, octyl, nonyl, decyl, and so on. The term "cycloalkyl" means a monocyclic saturated aliphatic hydrocarbon group having the specified number of carbon atoms. For example, "cycloalkyl" inlcudes cyclopropyl, methyl-cyclopropyl, 2,2-dimethyl-cyclobutyl, 2-ethyl-cyclopentyl, cyclohexyl, and so on.

"Alkoxy" represents either a cyclic or non-cyclic alkyl group of indicated number of carbon atoms attached through an oxygen bridge. "Alkoxy" therefore encompasses the definitions of alkyl and cycloalkyl above.

If no number of carbon atoms is specified, the term "alkenyl" refers to a non-aromatic hydrocarbon radical, straight, branched or cyclic, containing from 2 to 10 carbon atoms and at least one carbon to carbon double bond. Preferably one carbon to carbon double bond is present, and up to four non-aromatic carbon-carbon double bonds may be present. Thus, "$C_2$–$C_6$ alkenyl" means an alkenyl radical having from 2 to 6 carbon atoms. Alkenyl groups include ethenyl, propenyl, butenyl, 2-methylbutenyl and cyclohexenyl. The straight, branched or cyclic portion of the alkenyl group may contain double bonds and may be substituted if a substituted alkenyl group is indicated.

The term "alkynyl" refers to a hydrocarbon radical straight, branched or cyclic, containing from 2 to 10 carbon atoms and at least one carbon to carbon triple bond. Up to three carbon-carbon triple bonds may be present. Thus, "$C_2$–$C_6$ alkynyl" means an alkynyl radical having from 2 to 6 carbon atoms. Alkynyl groups include ethynyl, propynyl, butynyl, 3-methylbutynyl and so on. The straight, branched or cyclic portion of the alkynyl group may contain triple bonds and may be substituted if a substituted alkynyl group is indicated.

In certain instances, substituents may be defined with a range of carbons that includes zero, such as ($C_0$–$C_6$)alkylene-aryl. If aryl is taken to be phenyl, this definition would include phenyl itself as well as —$CH_2Ph$, —$CH_2CH_2Ph$, $CH(CH_3)CH_2CH(CH_3)Ph$, and so on.

As used herein, "aryl" is intended to mean any stable monocyclic or bicyclic carbon ring of up to 7 atoms in each ring, wherein at least one ring is aromatic. Examples of such aryl elements include phenyl, naphthyl, tetrahydronaphthyl, indanyl, biphenyl, phenanthryl, anthryl or acenaphthyl. In cases where the aryl substituent is bicyclic and one ring is non-aromatic, it is understood that attachment is via the aromatic ring.

The term heteroaryl, as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively.

As appreciated by those of skill in the art, "halo" or "halogen" as used herein is intended to include chloro, fluoro, bromo and iodo. The term "heterocycle" or "heterocyclyl" as used herein is intended to mean a 5- to 10-membered aromatic or nonaromatic heterocycle containing from 1 to 4 heteroatoms selected from the group consisting of O, N and S, and includes bicyclic groups. "Heterocyclyl" therefore includes the above mentioned heteroaryls, as well as dihydro and tetrathydro analogs thereof. Further examples of "heterocyclyl" include, but are not limited to the following: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. Attachment of a heterocyclyl substituent can occur via a carbon atom or via a heteroatom.

Preferably, heterocycle is selected from 2-azepinone, benzimidazolyl, 2-diazapinone, imidazolyl, 2-imidazolidinone, indolyl, isoquinolinyl, morpholinyl, piperidyl, piperazinyl, pyridyl, pyrrolidinyl, 2-piperidinone, 2-pyrimidinone, 2-pyrollidinone, quinolinyl, tetrahydrofuryl, tetrahydroisoquinolinyl, and thienyl.

The alkyl, alkenyl, alkynyl, cycloalkyl, aryl, heteroaryl and heterocyclyl substituents may be unsubstituted or unsubstituted, unless specifically defined otherwise. For example, a $(C_1-C_6)$alkyl may be substituted with one, two or three substituents selected from OH, oxo, halogen, alkoxy, dialkylamino, or heterocyclyl, such as morpholinyl, piperidinyl, and so on. In this case, if one substituent is oxo and the other is OH, the following are included in the definition: $—C=O)CH_2CH(OH)CH_3$, $—(C=O)OH$, $—CH_2(OH)CH_2CH(O)$, and so on.

In certain instances, $R^7$ and $R^8$ are defined such that they can be taken together with the nitrogen to which they are attached to form a monocyclic or bicyclic heterocycle with 5–7 members in each ring and optionally containing, in addition to the nitrogen, one or two additional heteroatoms selected from N, O and S, said heterocycle optionally substituted with one or more substituents selected from $R^{6a}$. Examples of the heterocycles that can thus be formed include, but are not limited to the following, keeping in mind that the heterocycle is optionally substituted with one or more substituents chosen from $R^{6a}$:

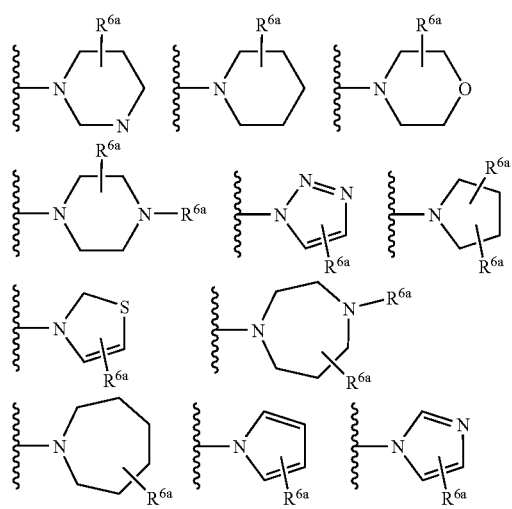

-continued

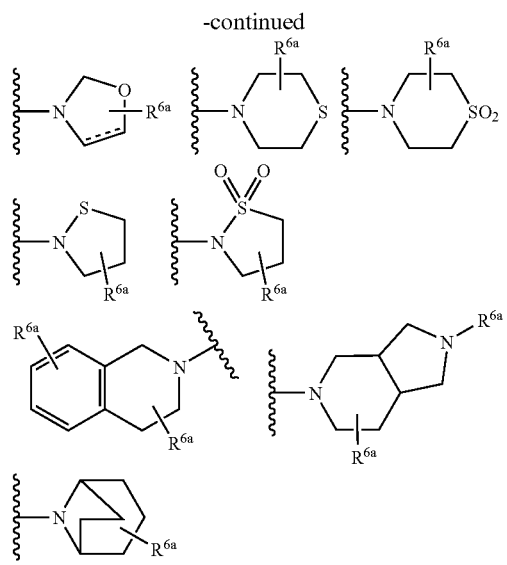

Preferably $R^1$ is selected from: H, halo, $(C_1-C_6)$alkyl, aryl, heterocyclyl, CN, $NH_2$, OH and $CO_2H$.

Also prefered is the definition of $R^2$ and $R^3$ as H. Preferably $R^5$ is H.

Preferably t is 1 and $R^4$ is displaced at the 5-position of the indole, according to the following numbering scheme:

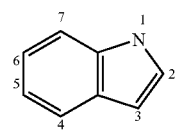

Preferably $R^4$ is defined as H, halo, $OC_1-C_6$ alkyleneNR$^7$R$^8$, $(C=O)_aC_0-C_6$ alkylene-Q, (wherein Q is H, OH, $CO_2H$, or $OC_1-C_6$ alkyl), $SO_2NH_2$, $C_1-C_6$ alkyleneNR$^7$R$^8$ or $OC_0-C_6$ alkylene-heterocyclyl, optionally substituted with one to three substituents selected from $R^{6a}$, $C_0-C_6$ alkyleneNR$^7$R$^8$, $(C=O)NR^7R^8$, or $OC_1-C_3$ alkylene-$(C=O)NR^7R^8$. Most preferably $R^4$ is H or $C_1-C_3$ alkyleneNR$^7$R$^8$.

Preferably $R^7$ and $R^8$ are defined such that they are taken together with the nitrogen to which they are attached to form a monocyclic 5–7 membered heterocycle and optionally containing, in addition to the nitrogen, one or two additional heteroatoms selected from N, O and S, and said heterocycle optionally substituted with one or more substituents selected from $R^{6a}$.

The pharmaceutically acceptable salts of the instant compounds can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the compounds of this invention include the conventional non-toxic salts of the compounds of this invention as formed by reacting a basic instant compound with an inorganic or organic acid. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

When the compound of the present invention is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, N,N$^1$-dibenzylethylenediamine, diethylamin, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

The compounds of this invention may be prepared by employing reactions as shown in the following schemes, in addition to other standard manipulations that are known in the literature or exemplified in the experimental procedures. These schemes, therefore, are not limited by the compounds listed or by any particular substituents employed for illustrative purposes. Substituent numbering as shown in the schemes does not necessarily correlate to that used in the claims.

Schemes

As shown in Scheme A, the indazoline reagent A-2 can be synthesized, by the general procedures taught by P. M. O'Neill et al. (*J. Med. Chem.* (1997) 40:437. Derivatives with varying substitution can be made by modifying this procedure and use of standard synthetic protocols known in the art. Also shown in Scheme 1 is the preparation of the indole intermediate A-6 (*Tetrahedron* 49:49–64 (1993)).

Scheme B illustrates one possible protocol for the coupling of the indole and indazoline intermediates to produce the compounds of the instant invention. Scheme C illustrates one possible synthetic route to the synthesis of an indazoline intermediate having a nitrogen atom in the six-membered ring. The synthesis of a corresponding regioisomer of that intermediate is illustrated in Scheme D.

Scheme E illustrates preparation of suitably substituted indole intermediates that can be used in coupling to the azaindazoline intermediate described in Scheme D. Scheme E also illustrates manipulation of the indole substituent subsequent to the coupling.

Scheme F illustrates the incorporation of an aryl moiety (optionallly substituted) on the indazole ring, via a palladium mediated tin coupling.

Scheme G illustrates an alternative method of forming the indole ring of the instant compounds which uses an anilinoacetylene as an intermediate (Villemin, D.; Goussu, D.; *Heterocycles* 1989, 29, 1255).

Scheme H illustrates additional manipulations of the indole substituent subsequent to the coupling.

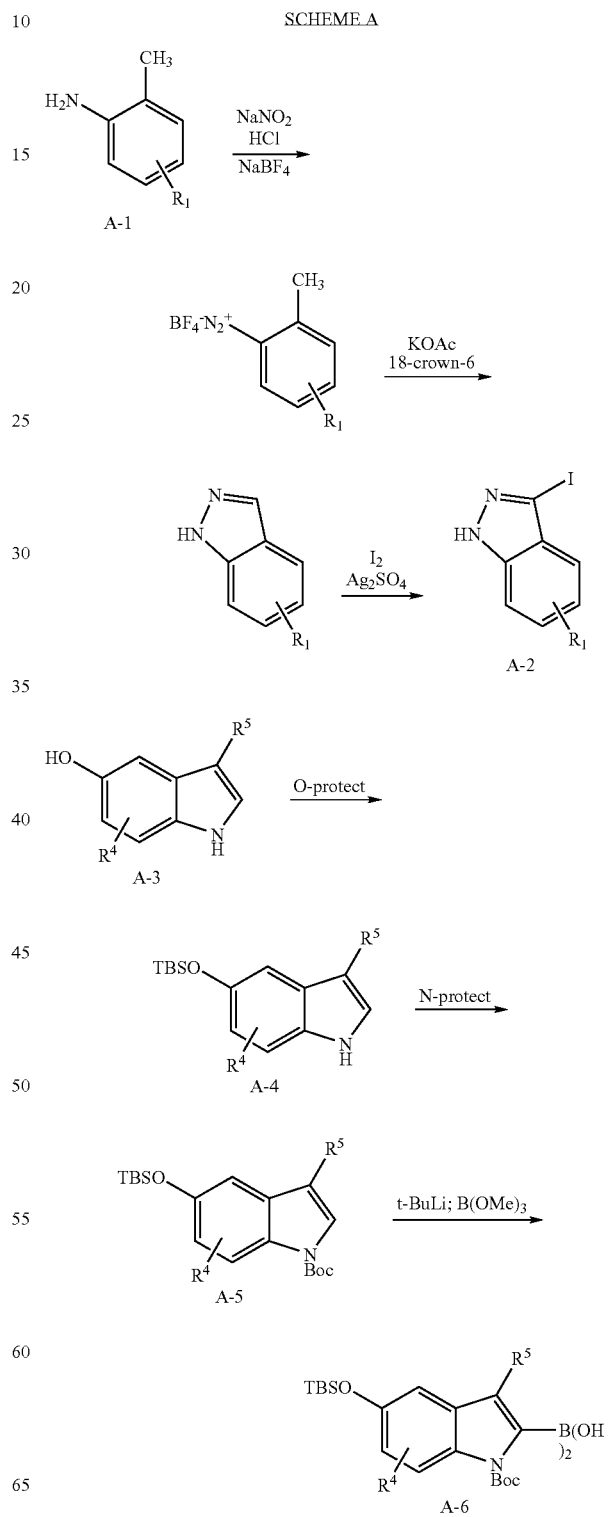

SCHEME B
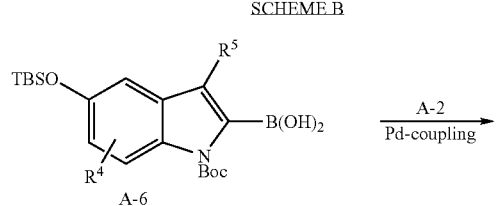
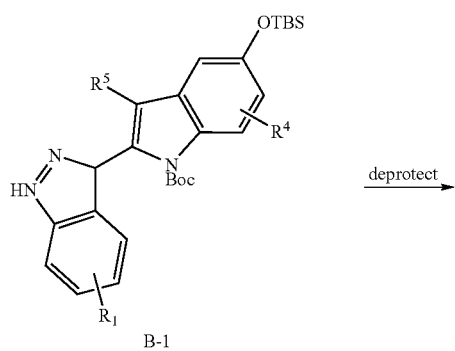
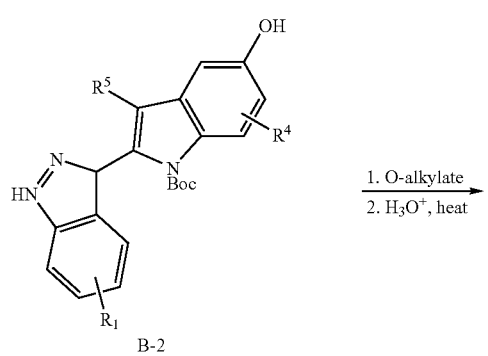
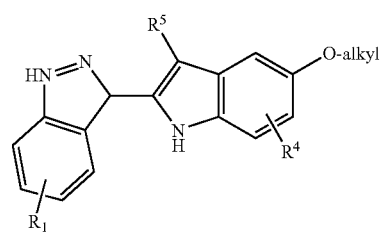
SCHEME C
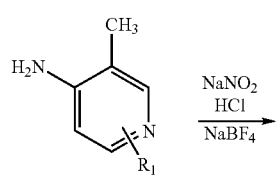
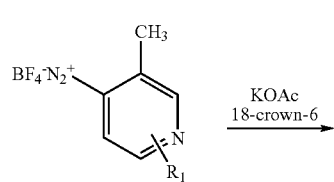
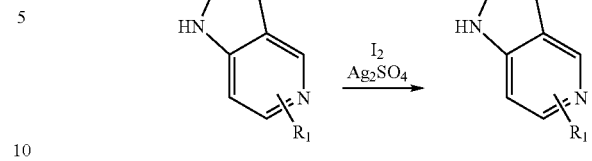
SCHEME D
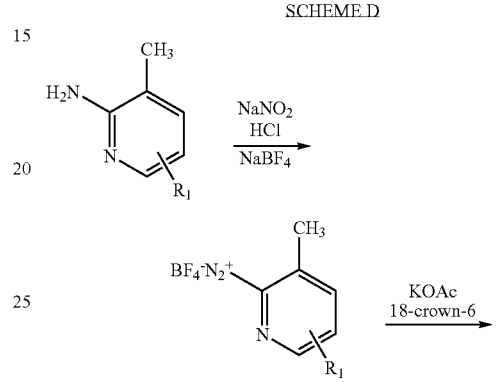
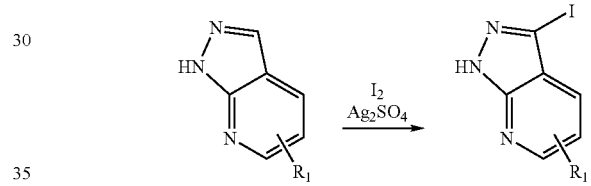
SCHEME E
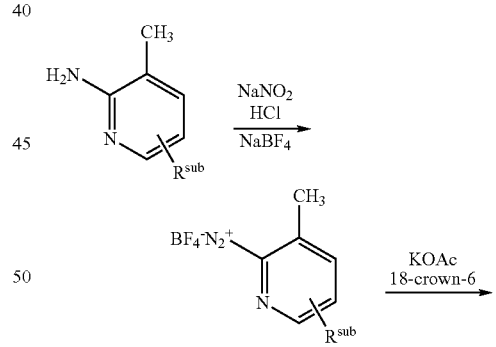
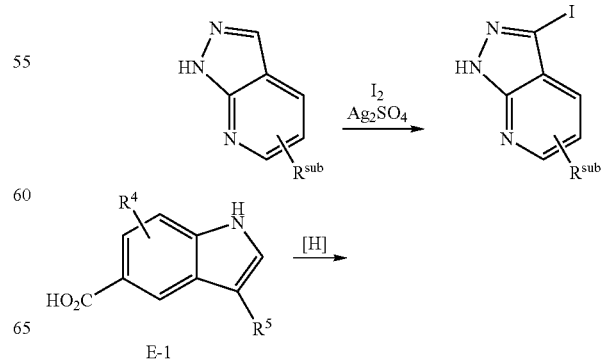

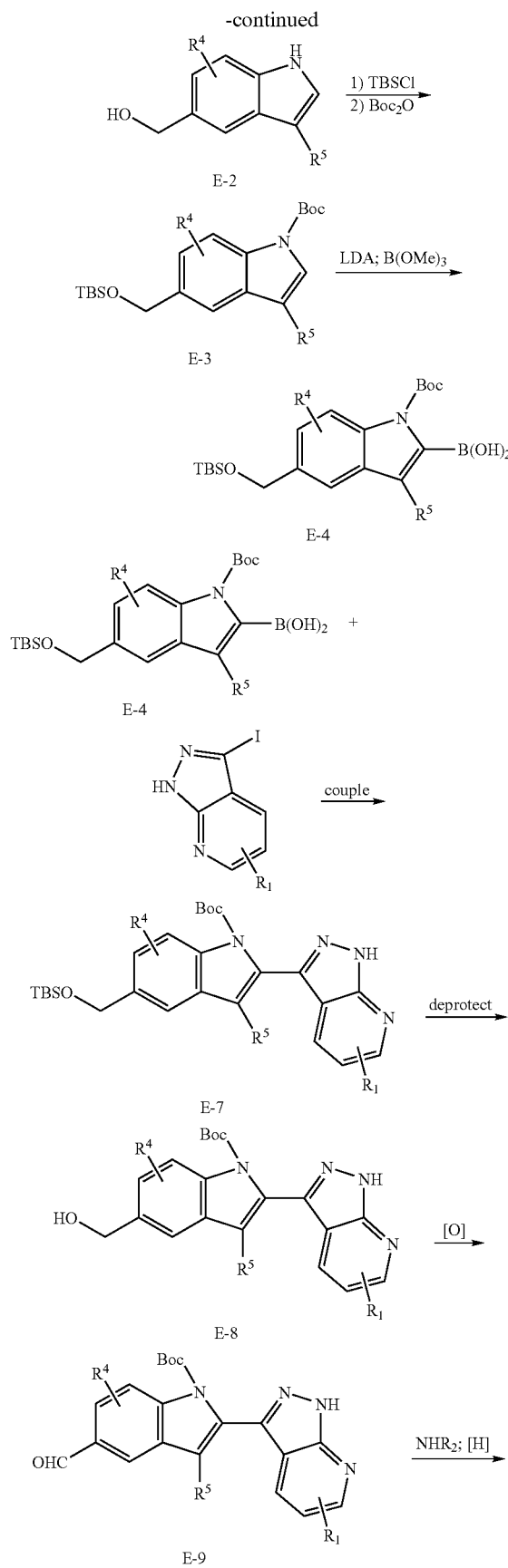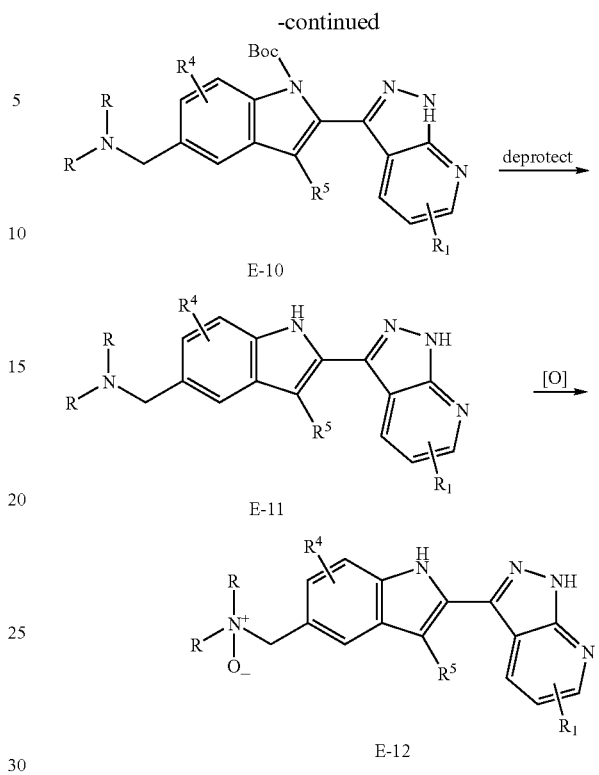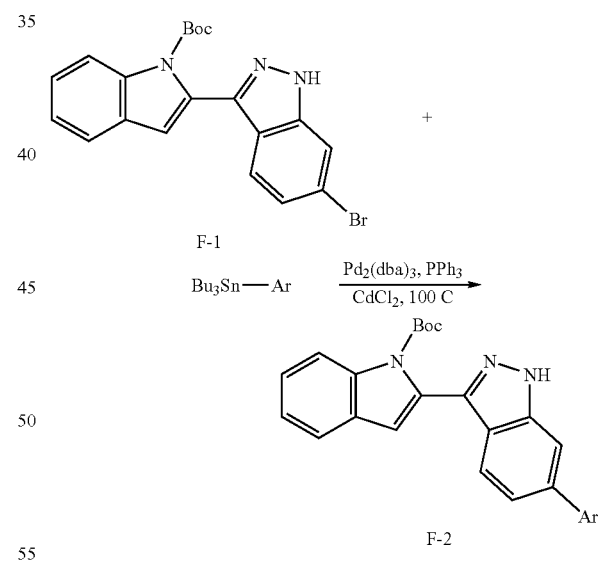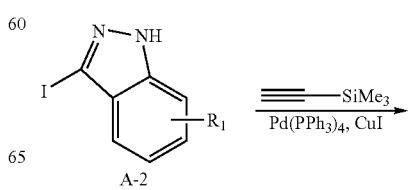

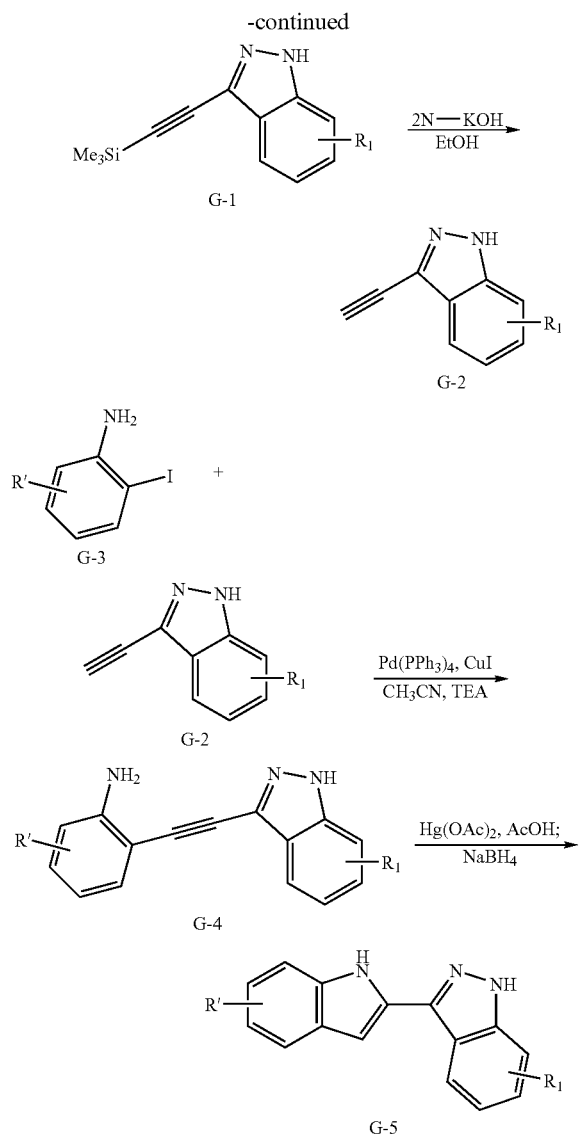

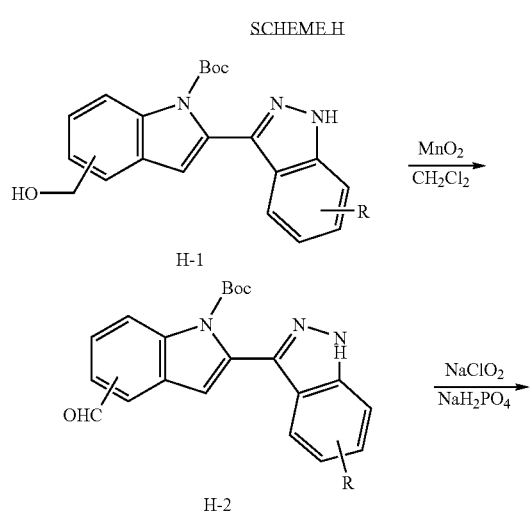

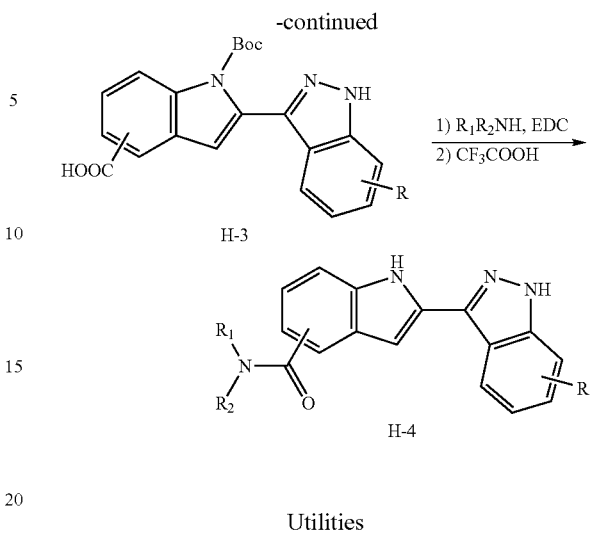

Utilities

Utilities

The compounds of the present invention are inhibitors of tyrosine kinase and are therefore useful to treat or prevent tyrosine kinase-dependent diseases or conditions in mammals.

"Tyrosine kinase-dependent diseases or conditions" refers to pathologic conditions that depend on the activity of one or more tyrosine kinases. Tyrosine kinases either directly or indirectly participate in the signal transduction pathways of a variety of cellular activities including proliferation, adhesion and migration, and differentiation. Diseases associated with tyrosine kinase activities include the proliferation of tumor cells, the pathologic neovascularization that supports solid tumor growth, ocular neovascularization (diabetic retinopathy, age-related macular degeneration, and the like) and inflammation (psoriasis, rheumatoid artritis, and the like). In treating such conditions with the instantly claimed compounds, the required therapeutic amount will vary according to the specific disease and is readily ascertainable by those skilled in the art. Although both treatment and prevention are contemplated by the scope of the invention, the treatment of these conditions is the preferred use.

The present invention encompasses a method of treating or preventing cancer in a mammal in need of such treatment which is comprised of administering to said mammal a therapeutically effective amount of a claimed compound. Preferred cancers for treatment are selected from cancers of the brain, genitourinary tract, lymphatic system, stomach, larynx and lung. Another set of preferred forms of cancer are histiocytic lymphoma, lung adenocarcinoma, small cell lung cancers, pancreatic cancer, glioblastomas and breast carcinoma. The utility of angiogenesis inhibitors in the treatment of cancer is known in the literature, see J. Rak et al. *Cancer Research*, 55:4575–4580, 1995, for example. The role of angiogenesis in cancer has been shown in numerous types of cancer and tissues: breast carcinoma (G. Gasparini and A. L. harris, *J. Clin. Oncol.*, 1995, 13:765–782; M. Toi et al., *Japan. J. Cancer Res.*, 1994, 85:1045–1049); bladder carcinomas (A. J. Dickinson et al., *Br. J. Urol.*, 1994, 74:762–766); colon carcinomas (L. M. Ellis et al., *Surgery*, 1996, 120(5):871–878); and oral cavity tumors (J. K. Williams et al., *Am. J. Surg.*, 1994, 168:373–380).

Tumors which have undergone neovascularization show an increased potential for metastasis VEGF released from cancer cells enhances metastasis possibly by increasing extravasation at points of adhesion to vascular endothelium. (A. Amirkhosravi et al., *Platelets*, 10:285–292 (1999)). In fact, angiogenesis is essential for tumor growth and metastasis. (S. P. Cunningham, et al., *Can. Research*, 61: 3206–3211 (2001)). The angiogenesis inhibitors disclosed in the present application are therefore also useful to prevent or decrease tumor cell metastasis. Such a use is also contemplated to be within the scope of the present invention.

Further included within the scope of the invention is a method of treating or preventing a disease in which angiogenesis is implicated, which is comprised of administering to a mammal in need of such treatment a therapeutically effective amount of a compound of the present invention. Ocular neovascular diseases are an example of conditions where much of the resulting tissue damage can be attributed to aberrant infiltration of blood vessels in the eye (see WO 00/30651, published 2 Jun. 2000). The undesireable infiltration can be triggered by ischemic retinopathy, such as that resulting from diabetic retinopathy, retinopathy of prematurity, retinal vein occlusions, etc., or by degenerative diseases, such as the choroidal neovascularization obeserved in age-related macular degeneration. Inhibiting the growth of blood vessels by administration of the present compounds would therefore prevent the infiltration of blood vessels and prevent or treat diseases where angiogenesis is implicated, such as ocular diseases like retinal vascularization, diabetic retinopathy, age-related macular degeneration, and the like.

Also included within the scope of the present invention is a method of treating or preventing inflammatory diseases which comprises administering to a mammal in need of such treatment a therapeutically effective amount of a compound of Formual I. Examples of such inflammatory diseases are rheumatoid arthritis, psoriasis, contact dermatitis, delayed hypersensitivity reactions, and the like. (A. Giatromanolaki et al., *J. Pathol.* 2001; 194:101–108.) For the role of VEGF in skin angiogenesis, see Michael Detmar, *J. Dermatological Sci.*, 24 Suppl. 1, S78–S84 (2000).

Also included within the scope of the present invention is a method of treating or preventing bone associated pathologies selected from osteosarcoma, osteoarthritis, and rickets, also known as oncogenic osteomalacia. (Hasegawa et al., *Skeletal Radiol.*, 28, pp. 41–45, 1999; Gerber et al., *Nature Medicine*, Vol. 5, No. 6, pp. 623–628, June 1999.) And since VEGF directly promotes osteoclastic bone resorption through KDR/Flk-1 expressed in mature osteoclasts (FEBS Let. 473:161–164 (2000); *Endocrinology*, 141:1667 (2000)), the instant compounds are also useful to treat and prevent conditions related to bone resorption, such as osteoporosis and Paget's disease.

A method of treating or preventing preeclampsia is also within the which comprises administering a therapeutically effective amount of a compound of the present invention. Studies have shown that the action of VEGF on the Flt-1 receptor is pivotal in the pathogenesis of preeclampsia. (*Laboratory Investigation* 79:1101–1111 (September 1999).) Vessels of pregnant women incubated with VEGF exhibit a reduction in endothelium-dependent relaxation similar to that induced by plasma from women with preeclampsia. In the presence of an anti-Flt-1 receptor antibody, however, neither VEGF or plasma from women with preeclampsia reduced the endothelium-dependent relaxation. Therefore the claimed compounds serve to treat preeclampsia via their action on the tyrosine kinase domain of the Flt-1 receptor.

Also within the scope of the invention is a method of reducing or preventing tissue damage following a cerebral ischemic event which comprises administering a therapeutically effective amount of a compound of the present invention. The claimed compounds can also be used to reduce or prevent tissue damage which occurs after cerebral ischemic events, such as stroke, by reducing cerebral edema, tissue damage, and reperfusion injury following ischemia. (*Drug News Perspect* 11:265–270 (1998); *J. Clin. Invest.* 104:1613–1620 (1999); *Nature Med* 7:222–227 (2001)).

The instant compounds can also be used to prevent or treat tissue damage during bacterial meningitis, such as tuberculous meningitis. Matsuyama et al., *J. Neurol. Sci.* 186:75–79 (2001)). The instant invention therefore encompasses a method of treating or preventing tissue damage due to bacterial meningitis which comprises administering a therapeutically effective amount of a claimed compound. Studies have shown that VEGF is secreted by inflammatory cells during bacterial meningitis and that VEGF contributes to blood-brain barrier disruption. (van der Flier et al., *J. Infectious Diseases*, 183:149–153 (2001)). The claimed compounds can inhibit VEGF-induced vascular permeability and therefore serve to prevent or treat blood-brain barrier disruption associated with bacterial meningitis.

The present invention further encompasses a method to treat or prevent endometrioses comprised of administering a therapeutically effective amount of a claimed compound. An increase in VEGF expression and angiogenesis is associated with the progression of endometriosis (Stephen K. Smith, *Trends in Endocrinology &Metabolism*, Vol. 12, No. 4, May/June 2001). Inhibition of VEGF by the current compounds would therefore inhibit angiogenesis and treat endometriosis.

A further embodiment of the present invention is a method of treating acute myeloid leukemia (AML) which comprises administering a therapeutically effective amount of a claimed compound. Activation of FLT3 on leukemic cells by FLT3 ligand leads to receptor dimerization and signal transduction in pathways that promote cell growth and inhibit apoptosis (*Blood*, Vol. 98, No. 3, pp. 885–887 (2001)). The present compounds are therefore useful to treat AML via inhibition of the tyrosine kinase domain of Flt-3.

The instant compounds can also be used to prevent or treat tissue damage during bacterial meningitis, such as tuberculous meningitis. Matsuyama et al., *J. Neurol Sci.* 186:75–79 (2001)). The instant invention therefore encompasses a method of treating or preventing tissue damage due to bacterial meningitis which comprises administering a therapeutically effective amount of a compound of Formula 1. Studies have shown that VEGF is secreted by inflammatory cells during bacterial meningitis and that VEGF contributes to blood-brain barrier disruption. (van der Flier et al., *J. Infectious Diseases*, 183:149–153 (2001)). The claimed compounds can inhibit VEGF-induced vascular permeability and therefore serve to prevent or treat blood-brain barrier disruption associated with bacterial meningitis.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

For oral use of a chemotherapeutic compound according to this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The instant compounds are also useful in combination with known therapeutic agents and anti-cancer agents, as described in U.S. Pat. No. 6,245,759 B1 (columns 14–19) and PCT Publ. No. WO 01/29025 (pages 33–41) (both of which are incorporated by reference).

The instant compounds are also useful in combination with known anti-cancer agents. Such known anti-cancer agents include the following: estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, and other angiogenesis inhibitors. The instant compounds are particularly useful when coadminsitered with radiation therapy. The synergistic effects of inhibiting VEGF in combination with radiation therapy have been described in the art (see WO 00/61186).

"Estrogen receptor modulators" refers to compounds which interfere or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenylhydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl)retinamide, and N-4-carboxyphenyl retinamide.

"Cytotoxic agents" refer to compounds which cause cell death primarily by interfering directly with the cell's functioning or inhibit or interfere with cell myosis, including alkylating agents, tumor necrosis factors, intercalators, microtubulin inhibitors, and topoisomerase inhibitors.

Examples of cytotoxic agents include, but are not limited to, tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine(chloro)platinum(II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, ME10755, and 4-demethoxy-3-deamino-3-aziridinyl-4-methylsulphonyl-daunorubicin (see WO 00/50032).

Examples of microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, and BMS188797.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H, 12H-benzo[de]pyrano[3',4':b,7] indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a, 5aB, 8aa,9b)-9-[2-[N-[2-(dimethylamino)ethyl]-N-methylamino]ethyl]-5-[4-hydroxy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxy-benzo[c]-phenanthridinium, 6,9-bis[(2-aminoethyl)amino] benzo[g]isoguinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino) ethylamino]-7-methoxy-9-oxo-9H-thioxanthen-4-ylmethyl] formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydro-benzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-flurouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, and 3-aminopyridine-2-carboxaldehyde thiosemicarbazone. "Antiproliferative agents" also includes monoclonal antibodies to growth factors, other than those listed under "angiogenesis inhibitors", such as trastuzumab, and tumor suppressor genes, such as p53, which can be delivered via recombinant virus-mediated gene transfer (see U.S. Pat. No. 6,069,134, for example).

"HMG-CoA reductase inhibitors" refers to inhibitors of 3-hydroxy-3-methylglutaryl-CoA reductase. Compounds which have inhibitory activity for HMG-CoA reductase can be readily identified by using assays well-known in the art. For example, see the assays described or cited in U.S. Pat. No. 4,231,938 at col. 6, and WO 84/02131 at pp. 30–33. The terms "HMG-CoA reductase inhibitor" and "inhibitor of HMG-CoA reductase" have the same meaning when used herein.

Examples of HMG-CoA reductase inhibitors that may be used include but are not limited to lovastatin (MEVACOR®; see U.S. Pat. Nos. 4,231,938; 4,294,926; 4,319,039), simvastatin (ZOCOR®; see U.S. Pat. Nos. 4,444,784; 4,820,850; 4,916,239), pravastatin (PRAVACHOL®; see U.S. Pat. Nos. 4,346,227; 4,537,859; 4,410,629; 5,030,447 and 5,180,589), fluvastatin (LESCOL®; see U.S. Pat. Nos. 5,354,772; 4,911,165; 4,929,437; 5,189,164; 5,118,853; 5,290,946; 5,356,896), atorvastatin (LIPITOR®; see U.S. Pat. Nos. 5,273,995; 4,681,893; 5,489,691; 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", *Chemistry & Industry*, pp. 85–89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention. An illustration of the lactone portion and its corresponding open-acid form is shown below as structures I and II.

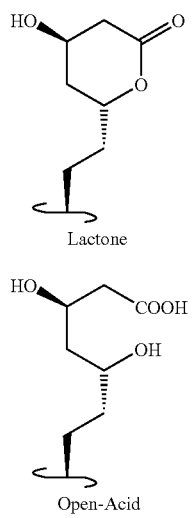

In HMG-CoA reductase inhibitors where an open-acid form can exist, salt and ester forms may preferably be formed from the open-acid, and all such forms are included within the meaning of the term "HMG-CoA reductase inhibitor" as used herein. Preferably, the HMG-CoA reductase inhibitor is selected from lovastatin and simvastatin, and most preferably simvastatin. Herein, the term "pharmaceutically acceptable salts" with respect to the HMG-COA reductase inhibitor shall mean non-toxic salts of the compounds employed in this invention which are generally prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrrolidine-1'-yl-methylbenz-imidazole, diethylamine, piperazine, and tris(hydroxymethyl)aminomethane. Further examples of salt forms of HMG-CoA reductase inhibitors may include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, and valerate.

Ester derivatives of the described HMG-CoA reductase inhibitor compounds may act as prodrugs which, when absorbed into the bloodstream of a warm-blooded animal, may cleave in such a manner as to release the drug form and permit the drug to afford improved therapeutic efficacy.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase). Examples of prenyl-protein transferase inhibiting compounds include (±)-6-[amino(4-chlorophenyl)(1-methyl-1H-imidazol-5-yl) methyl]-4-(3-chlorophenyl)-1-methyl-2(1H)-quinolinone, (−)-6-[amino(4-chlorophenyl)(1-methyl-1H-imidazol-5-yl) methyl]-4-(3-chlorophenyl)-1-methyl-2(1H)quinolinone, (+)-6-[amino(4-chlorophenyl)(1-methyl-1H-imidazol-5-yl) methyl]-4-(3-chlorophenyl)-1-methyl-2(1H)-quinolinone, 5(S)-n-butyl-1-(2,3-dimethylphenyl)-4-[1-(4-cyanobenzyl)-5-imidazolylmethyl]-2-piperazinone, (S)-1-(3-chlorophenyl)-4-[1-(4-cyanobenzyl)-5-imidazolylmethyl]-5-[2-(ethanesulfonyl)methyl)-2-piperazinone, 5(S)-n-Butyl-1-(2-methylphenyl)-4-[1-(4-cyanobenzyl)-5-imidazolylmethyl]-2-piperazinone, 1-(3-chlorophenyl)-4-[1-(4-cyanobenzyl)-2-methyl-5-imidazolylmethyl]-2-piperazinone, 1-(2,2-diphenylethyl)-3-[N-(1-(4-cyanobenzyl)-1H-imidazol-5-ylethyl)carbamoyl]piperidine, 4-{5-[4-hydroxymethyl-4-(4-chloropyridin-2-ylmethyl)-piperidine-1-ylmethyl]-2-methylimidazol-1-ylmethyl}benzonitrile, 4-{5-[4-hydroxymethyl-4-(3-chlorobenzyl)-piperidine-1-ylmethyl]-2-methylimidazol-1-ylmethyl}benzonitrile, 4-{3-[4-(2-oxo-2H-pyridin-1-yl)benzyl]-3H-imidazol-4-ylmethyl}benzonitrile, 4-{3-[4-(5-chloro-2-oxo-2H-[1,2'] bipyridin-5'-ylmethyl]-3H-imidazol-4-ylmethyl}benzonitrile, 4-{3-[4-(2-oxo-2H-[1,2']bipyridin-5'-ylmethyl]-3H-imidazol-4-ylmethyl}benzonitrile, 4-[3-(2-oxo-1-phenyl-1,2-dihydropyridin-4-ylmethyl)-3H- imidazol-4-ylmethyl}benzonitrile, 18,19-dihydro-19-oxo-5H,17H-6,10:12,16-dimetheno-1H-imidazo[4,3-c][1,11,4]dioxaazacyclo-nonadecine-9-carbonitrile, (±)-19,20-dihydro-19-oxo-5H-18,21-ethano-12,14-etheno-6,10-metheno-22H-benzo[d]imidazo[4,3-k][1,6,9,12]oxatriaza-cyclooctadecine-9-carbonitrile, 19,20-dihydro-19-oxo-5H,17H-18,21-ethano-6,10:12,16-dimetheno-22H-imidazo[3,4-h][1,8,11,14]oxatriazacycloeicosine-9-carbonitrile, and (±)-19,20-dihydro-3-methyl-19-oxo-5H-18,21-ethano-12,14-etheno-6,10-metheno-22H-benzo[d]imidazo[4,3-k][1,6,9,12]oxa-triazacyclooctadecine-9-carbonitrile.

Other examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see European J. of Cancer, Vol. 35, No. 9, pp. 1394–1401 (1999).

Examples of HIV protease inhibitors include amprenavir, abacavir, CGP-73547, CGP-61755, DMP-450, indinavir, nelfinavir, tipranavir, ritonavir, saquinavir, ABT-378, AG 1776, and BMS-232,632. Examples of reverse transcriptase inhibitors include delaviridine, efavirenz, GS-840, HB Y097, lamivudine, nevirapine, AZT, 3TC, ddC, and ddI.

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR20), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxygenase-2 inhibitors like celecoxib and rofecoxib (PNAS, Vol. 89, p. 7384 (1992); JNCI, Vol. 69, p. 475 (1982); Arch. Opthalmol., Vol. 108, p. 573 (1990); Anat. Rec., Vol. 238, p. 68 (1994); FEBS Letters, Vol. 372, p. 83 (1995); Clin, Orthop. Vol. 313, p. 76 (1995); J. Mol. Endocrinol., Vol. 16, p. 107. (1996); Jpn. J. Pharmacol., Vol. 75, p. 105 (1997); Cancer Res., Vol. 57, p. 1625 (1997); Cell, Vol. 93, p. 705 (1998); Intl. J. Mol., Med., Vol. 2, p. 715 (1998); J. Biol. Chem., Vol. 274, p. 9116 (1999)), carboxyamidotriazole, combretastatin A-4, squalamine, 6-O-chloro-acetyl-carbonyl)-fumagillol, thalidomide, angiostatin, troponin-1, angiotensin II antagonists (see Fernandez et al., J. Lab. Clin. Med. 105:141–145 (1985)), and antibodies to VEGF (see; Nature Biotechnology, Vol. 17, pp. 963 968 (October 1999); Kim et al., Nature, 362, 841–844 (1993); WO 00/44777; and WO 00/61186).

As described above, the combinations with NSAID's are directed to the use of NSAID's which are potent COX-2 inhibiting agents. For purposes of this specification an NSAID is potent if it possess an $IC_{50}$ for the inhibition of COX-2 of 1 μM or less as measured by the cell or microsomal assay disclosed herein.

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by the cell or micromsal assay disclosed hereinunder. Such compounds include, but are not limited to those disclosed in U.S. Pat. No. 5,474,995, issued Dec. 12, 1995, U.S. Pat. No. 5,861,419, issued Jan. 19, 1999, U.S. Pat. No. 6,001,843, issued Dec. 14, 1999, U.S. Pat. No. 6,020,343, issued Feb. 1, 2000, U.S. Pat. No. 5,409,944, issued Apr. 25, 1995, U.S. Pat. No. 5,436,265, issued Jul. 25, 1995, U.S. Pat. No. 5,536,752, issued Jul. 16, 1996, U.S. Pat. No. 5,550,142, issued Aug. 27, 1996, U.S. Pat. No. 5,604,260, issued Feb. 18, 1997, U.S. Pat. No. 5,698,584, issued Dec. 16, 1997, U.S. Pat. No. 5,710,140, issued Jan. 20, 1998, WO 94/15932, published Jul. 21, 1994, U.S. Pat. No. 5,344,991, issued Jun. 6, 1994, U.S. Pat. No. 5,134,142, issued Jul. 28, 1992, U.S. Pat. No. 5,380,738, issued Jan. 10, 1995, U.S. Pat. No. 5,393,790, issued Feb. 20, 1995, U.S. Pat. No. 5,466,823, issued Nov. 14, 1995, U.S. Pat. No. 5,633,272, issued May 27, 1997, and U.S. Pat. No. 5,932,598, issued Aug. 3, 1999, all of which are hereby incorporated by reference.

Other examples of specific inhibitors of COX-2 include the following:

3-(3-fluorophenyl)-4-(4(methylsulfonyl)phenyl)-2-(5H)-furanone;

3-(3,4-difluorophenyl)-4-(4-(methylsulfonyl)phenyl)-2-(5H)-furanone;

3-(3,4-dichlorophenyl)-4-(4-(methylsulfonyl)phenyl)-2-(5H)-furanone;

3-phenyl-4-(4-(methylsulfonyl)phenyl)-2-(5H)-furanone;

5,5-dimethyl-3-(3-fluorophenyl)-4-(methylsulfonyl)phenyl)-2-(5H)-furanone;

3-(4-methylsulfonyl)phenyl-2-phenyl-5-trifluoromethylpyridine;

2-(3-chlorophenyl)-3-(4-methylsulfonyl)phenyl-5-trifluoromethyl-pyridine;

2-(4-chlorophenyl)-3-(4-methylsulfonyl)phenyl-5-trifluoromethyl-pyridine;

2-(4-fluorophenyl)-3-(4-methylsulfonyl)phenyl-5-trifluoromethyl-pyridine;

3-(4-methylsulfonyl)phenyl-2-(3-pyridinyl)-5-trifluoromethylpyridine;

5-methyl-3-(4-methylsulfonyl)phenyl-2-phenylpyridine;

2-(4-chlorophenyl)-5-methyl-3-(4-methylsulfonyl)phenylpyridine;

5-methyl-3-(4-methylsulfonyl)phenyl-2-(3-pyridinyl)pyridine;

5-chloro-2-(4-chlorophenyl)-3-(4-methylsulfonyl)phenylpyridine;

5-chloro-3-(4-methylsulfonyl)phenyl-2-(2-pyridinyl)pyridine;

5-chloro-3-(4-methylsulfonyl)phenyl-2-(3-pyridinyl)pyridine;

5-chloro-3-(4-methylsulfonyl)phenyl-2-(4-pyridinyl)pyridine;

5-chloro-3-(4-methylsulfonyl)phenyl-2-(2-methyl-5-pyridinyl)pyridine;

2-(4-chlorophenyl)-3-(4-methylsulfonyl)phenylpyridinyl-5-carboxylic acid methyl ester;

2-(4-chlorophenyl)-3-(4-methylsulfonyl)phenylpyridinyl-5-carboxylic acid;

5-cyano-2-(4-chlorophenyl)-3-(4-methylsulfonyl)phenylpyridine;

5-chloro-3-(4-methylsulfonyl)phenyl-2-(3-pyridyl)pyridine hydromethanesulfonate;

5-chloro-3-(4-methylsulfonyl)phenyl-2-(3-pyridyl)pyridine hydrochloride;

5-chloro-3-(4-methylsulfonyl)phenyl-2-(2-methyl-5-pyridinyl)pyridine hydrochloride;

5-chloro-3-(4-methylsulfonyl)phenyl-2-(2-ethyl-5-pyridinyl)pyridine;

5-chloro-3-(4-methylsulfonyl)phenyl-2-(2ethyl-5-pyridinyl)pyridine hydromethanesulfonate;

3-(3,4-difluorophenoxy)-5,5-dimethyl-4-(4-(methylsulfonyl)phenyl)-5H-furan-2-one;

3-(3-fluorophenoxy)-5,5-dimethyl-4-(4-(methylsulfonyl)phenyl)-5H-furan-2-one;

3-(3,5-difluorophenoxy)-5,5-dimethyl-4-(methylsulfonyl)phenyl)-5H-furan-2-one;

3-phenoxy-5,5-dimethyl-4-(4-(methylsulfonyl)phenyl)-5H-furan-2-one;

3-(2,4-difluorophenoxy)-5,5-dimethyl-4-(4-(methylsulfonyl)phenyl)-5H-furan-2-one;

3-(4-chlorophenoxy)-5,5-dimethyl-4-(4-(methylsulfonyl)phenyl)-5H-furan-2-one;

3-(3,4-dichlorophenoxy)-5,5-dimethyl-4-(methylsulfonyl)phenyl)-5H-furan-2-one;

3-(4-fluorophenoxy)-5,5-dimethyl-4-(4-(methylsulfonyl)phenyl)-5H-furan-2-one;

3-(4-fluorophenylthio)-5,5-dimethyl-4-(4-(methylsulfonyl)phenyl)-5H-furan-2-one;

3-(3,5-difluorophenylthio)-5,5-dimethyl-4-(4-(methylsulfonyl)phenyl)-5H-furan-2-one;

3-phenylthio-5,5-dimethyl-4-(4-(methylsulfonyl)phenyl)-5H-furan-2-one;

3-(N-phenylamino)-5,5-dimethyl-4-(4-(methylsulfonyl)phenyl)-5H-furan-2-one;

3-(N-methyl-N-phenylamino)-5,5-dimethyl-4-(4-(methylsulfonyl)phenyl)-5H-furan-2-one;

3-cyclohexyloxy-5,5-dimethyl-4-(4-(methylsulfonyl)phenyl)-5H-furan-2-one;

3-phenylthio-4-(4-(methylsulfonyl)phenyl)-5H-furan-2-one;

3-benzyl-5,5-dimethyl-4-(4-(methylsulfonyl)phenyl)-5H-furan-2-one;

3-(3,4-difluorophenylhydroxymethyl)-5,5-dimethyl-4-(4-(methylsulfonyl)phenyl)-5H-furan-2-one;

3-(3,4-difluorobenzoyl)-5,5-dimethyl-4-(4-(methylsulfonyl)phenyl)-5H-furan-2-one;

3-benzoyl-5,5-dimethyl-4-(4-(methylsulfonyl)phenyl)-5H-furan-2-one;

4-(4-(methylsulfonyl)phenyl)-3-phenoxy-1-oxaspiro[4.4]non-3-en-2-one;

4-(4-(methylsulfonyl)phenyl)-3-phenylthio-1-oxaspiro[4.4]non-3-en-2-one;

4-(2-oxo-3-phenylthio-1-oxa-spiro[4,4]non-3-en-4-yl)benzenesulfonamide;

3-(4-fluorobenzyl)-5,5-dimethyl-4-(4-(methylsulfonyl)phenyl)-5H-furan-2-one;

3-(3,4-difluorophenoxy)-5-methoxy-5-methyl-4-(4-(methylsulfonyl)phenyl)-5H-furan-2-one;

3-(5-chloro-2-pyridyloxy)-5,5-dimethyl-4-(4-(methylsulfonyl)phenyl)-5H-furan-2-one;

3-(2-pyridyloxy)-5,5-dimethyl-4-(4-(methylsulfonyl)phenyl)-5H-furan-2-one;

3-(6-methyl-2-pyridyloxy)-5,5-dimethyl-4-(4-(methylsulfonyl)phenyl)-5H-furan-2-one;

3-(3-isoquinolinoxy)-5,5-dimethyl-4-(4-(methylsulfonyl)phenyl)-5H-furan-2-one;

3-(4-(methylsulfonyl)phenyl)-2-phenoxycyclopent-2-enone;

3-(4-(methylsulfonyl)phenyl)-2-(3,4-fluorophenoxy)cyclopent-2-enone;

5,5-dimethyl-4-(4-methylsulfonylphenyl)-3-(5-bromopyridin-2-yloxy)-5H-furan-2-one;

5,5-dimethyl-4-(4-methylsulfonylphenyl)-3-(2-propoxy)-5H-furan-2-one;

2-(3,4-difluorophenoxy)-3-(4-methylsulfonylphenyl)cyclopent-2-enone;

3-(5-benzothiophenyloxy)-5,5-dimethyl-4-(4-(methylsulfonyl)phenyl)-5H-furan-2-one;

5,5-dimethyl-4-(4methylsulfonyl-phenyl)-3-(pyridyl-4-oxy)-5H-furan-2-one;

5,5-dimethyl-4-(4-methylsulfonyl-phenyl)-3-(pyridyl-3-oxy)-5H-furan-2-one;

3-(2-methyl-5-pyridyloxy)-5,5-dimethyl-4-(methylsulfonyl)phenyl)-5H-furan-2-one;

3-(2-fluoro-4-trifluoromethyl)phenoxy-4-(4-methylsulfonyl)phenyl)-5,5-dimethyl-5H-furan-2-one;

3-(5-chloro-2-pyridylthio)-5,5-dimethyl-4-(4-methylsulfonyl)phenyl-5H-furan-2-one;

2-(3,5-difluorophenoxy)-3-(4-methylsulfonylphenyl)-cyclopent-2-enone;

3-(2-pyrimidinoxy)-5,5-dimethyl-4-(4-methylsulfonyl)phenyl-5H-furan-2-one;

3-(3-methyl-2-pyridyloxy)-5,5-dimethyl-4-(4-methylsulfonyl)phenyl-5H-furan-2-one;

3-(3-chloro-5-pyridyloxy)-5,5-dimethyl-4-(4-(methylsulfonyl)phenyl)-5H-furan-2-one;

3-(3-(1,2,5-thiadiazolyl)oxy)-4-(4-(methylsulfonyl)phenyl)-5,5-dimethyl-5H-furan-2-one;

3-(5-isoquinolinoxy)-5,5-dimethyl-4-(4-methylsulfonyl)phenyl-5H-furan-2-one;

3-(6-amino-2-pyridyloxy)-5,5-dimethyl-4-(4-(methylsulfonyl)phenyl)-5H-furan-2-one;

3-(3-chloro-4-fluoro)phenoxy-4-(methylsulfonyl)phenyl)-5,5-dimethyl-5H-furan-2-one;

3-(6-quinolinoxy)-5,5-dimethyl-4-(4-(methylsulfonyl)phenyl)-5H-furan-2-one;

3-(5-nitro-2-pyridyloxy)-5,5-dimethyl-4-(4-methylsulfonyl)phenyl-5H-furan-2-one;

3-(2-thiazolylthio)-5,5-dimethyl-4-(4-(methylsulfonyl)phenyl)-5H-furan-2-one;

3-(3-chloro-5-pyridyloxy)-5,5-dimethyl-4-(4-(methylsulfonyl)phenyl)-5H-furan-2-one;

5,5-dimethyl-4-(4-methylsulfonylphenyl)-3-(2-propoxy)-5H-furan-2-one;

3-(3-trifluoromethyl)phenoxy-4-(4-methylsulfonyl)phenyl)-5,5-dimethyl-5H-furan-2-one;

5,5-dimethyl-(4-(4-methylsulfonyl)phenyl)-3-(piperidine-1-carbonyl)-5-H-furan-2-one;

5,5-dimethyl-3-(2-Butoxy)-4-(4-methylsulfonylphenyl)-5H-furan-2-one;

5,5-dimethyl-4-(4-methylsulfonylphenyl)-3-(3-pentoxy)-5H-furan-2-one;

2-(5-chloro-2-pyridyloxy)-3-(4-methylsulfonyl)phenylcyclopent-2-enone;

3-(4-methyl-2-pyridyloxy)-5,5-dimethyl-4-(4-methylsulfonyl)phenyl-5H-furan-2-one;

(5R)-3-(3,4-difluorophenoxy)-5-ethyl-5-methyl-4-(4-methylsulfonyl)phenyl-5H-furan-2-one;

(5R)-3-(4-chlorophenoxy)-5-ethyl-5-methyl-4-(4-methylsulfonyl)phenyl-5H-furan-2-one;

3-(2-methyl-3-pyridyloxy)-5,5-dimethyl-4-(4-methylsulfonyl)phenyl-5H-furan-2-one;

3-(4-methyl-5-nitro-2-pyridyloxy)-5,5-dimethyl-4-(4-methylsulfonyl)phenyl-5H-furan-2-one;

3-(5-chloro-4-methyl-2-pyridyloxy)-5,5-dimethyl-4-(4-methylsulfonyl)phenyl-5H-furan-2-one;

3-(5-fluoro-4-methyl-2-pyridyloxy)-5,5-dimethyl-4-(4-methylsulfonyl)phenyl-5H-furan-2-one;

3-(3-chloro-2-pyridyloxy)-5,5-dimethyl-4-methylsulfonyl)phenyl-5H-furan-2-one;

3-(4-fluorophenoxy)-5-methyl-4-(4-methylsulfonyl)phenyl-5-propyl-5H-furan-2-one;

3-(N,N-diethylamino)-5,5-dimethyl-4-(4-(methylsulfonyl)phenyl)-5H-furan-2-one;

5,5-dimethyl-4-(4-methylsulfonyl-phenyl)-3-(3,5-dichloro-2-pyridyloxy)-5H-furan-2-one;

(5R)-3-(4-bromophenoxy)-5-ethyl-5-methyl-4-(4-methylsulfonyl)phenyl-5H-furan-2-one;

(5R)-3-(4-methoxyphenoxy)-5yl-5-methyl-4-(4-methylsulfonyl)phenyl-5H-furan-2-one;

(5R)-3-(5-chloro-2-pyridyloxy)-5-methyl-4-(4-methylsulfonyl)phenyl-5-(2,2,2-trifluoroethyl)-5H-furan-2-one;

3-(5-chloro-2-pyridyloxy)-5-methyl-4-(4-methylsulfonyl)phenyl-5-propyl-5H-furan-2-one;

3-(1-cyclopropyl-ethoxy)-5,5-dimethyl-4-(4-methyl sulfonyl)phenyl)-5H-furan-2-one;

5-methyl-4-(4-(methylsulfonyl)phenyl)-3-(2-(propoxy)-5-(2-trifluoroethyl)-5H-furan-2-one;

5(R)-5-ethyl-5-methyl-4-(4-(methylsulfonyl)phenyl)-3-(2-propoxy)-5H-furan-2-one;

5,5-dimethyl-3-(2,2-dimethylpropyloxy)-4-(4-(methylsulfonyl)phenyl)-5H-furan-2-one;

5(R)-3-(1-cyclopropyl-ethoxy)-5-ethyl-5-methyl-4-(4-(methyl sulfonyl)phenyl-5H-furan-2-one;

5(S)-5-ethyl-5-methyl-4-(4-(methylsulfonyl)phenyl)-3-(2-propoxy)-5H-furan-2-one;

3-(1-cyclopropyl-ethoxy)-5,5-dimethyl-4-(4-(methylsulfonyl)phenyl)-5H-furan-2-one;

3-(1-cyclopropylethoxy)-5,5-dimethyl-4-(4-(methylsulfonyl)phenyl)-5H-furan-2-one;

5,5-dimethyl-3-(isobutoxy)-4-(4-(methylsulfonyl)phenyl)-5H-furan-2-one;

3-(4-bromophenoxy)-5,5-dimethyl-4-(4-(methylsulfonyl)phenyl)-5H-furan-2-one;

3-(2-quinolinoxy)-5,5-dimethyl-4-(4-(methylsulfonyl)phenyl)-5H-furan-2-one;

3-(2-chloro-5-pyridyloxy)-5,5-dimethyl-4-(4-(methylsulfonyl)phenyl)-5H-furan-2-one;

3-(6-benzothiazolyloxy)-5,5-dimethyl-4-(4-(methylsulfonyl)phenyl)-5H-furan-2-one;

3-(6-chloro-2-pyridyloxy)-5,5-dimethyl-4-(4-(methylsulfonyl)phenyl)-5H-furan-2-one;

3-(4-quinazolyloxy)-5,5-dimethyl-4-(4-(methylsulfonyl)phenyl)-5H-furan-2-one;

(5R)-3-(5-fluoro-2-pyridyloxy)-5-ethyl-5-methyl-4-(4-methylsulfonyl)phenyl-5H-furan-2-one;

(5R)-3-(4-fluorophenoxy)-5-ethyl-5-methyl-4-(4-methylsulfonyl)phenyl-5H-furan-2-one;

(5R)-3-(5-fluoro-2-pyridyloxy)-5-methyl-4-(4-methylsulfonyl)phenyl-5-(2,2,2-trifluoroethyl)-5H-furan-2-one;

3-(1-isoquinolinyloxy)-5,5-dimethyl-4-(methylsulfonyl)phenyl-5H-furan-2-one;

(5R)-3-(4-fluorophenoxy)-5-methyl-4-(4-methylsulfonyl)phenyl-5-(2,2,2-trifluoroethyl)-5H-furan-2-one;

3-(3-fluoro-2-pyridyloxy)-5,5-dimethyl-4-(4-methylsulfonyl)phenyl-5H-furan-2-one;

(5R)-3-(3,4-difluorophenoxy)-5-methyl-4-(4-methylsulfonyl)phenyl-5-(2,2,2-trifluoroethyl)-5H-furan-2-one;

(5R)-3-(5-chloro-2-pyridyloxy)-5-ethyl-5-methyl-4-(4-methylsulfonyl)phenyl-5H-furan-2-one;

3-(3,4-difluorophenoxy)-5-methyl-5-trifluoromethyl-4-(4-methylsulfonyl)phenyl-5H-furan-2-one;

3-(3,4-difluorophenoxy)-5-methyl-4-(4-(methylsulfonyl)phenyl)-5-propyl-5H-furan-2-one;

3-cyclobutyloxy-5,5-dimethyl-4-(4-methylsulfonylphenyl-5H-furan-2-one;

3-(1-indanyloxy)-5,5-dimethyl-4-(4-(methylsulfonyl)phenyl)-5H-furan-2-one;

3-(2-indanyloxy)-5,5-dimethyl-4-(4-methylsulfonyl)phenyl)-5H-furan-2-one;

3-cyclopentyloxy-5,5-dimethyl-4-(4-methylsulfonylphenyl)-5H-furan-2-one;

3-(3,3-dimethylcyclopentyloxy)-5,5-dimethyl-4-(4-methylsulfonyl-phenyl)-5H-furan-2-one;

3-isopropoxy-5-methyl-4-(4-methylsulfonylphenyl)-5-propyl-5H-furan-2-one;

3-(2-methoxy-5-pyridyloxy)-5,5-dimethyl-4-(4-methylsulfonyl)phenyl-5H-furan-2-one;

3-(5-methyl-2-pyridyloxy)-5,5-dimethyl-4-(4-methylsulfonyl)phenyl-5H-furan-2-one;

(5RS)-3-(3,4-difluorophenoxy)-5-methyl-4-(4-methylsulfonyl)phenyl-5-(2,2,2-trifluoroethyl)-5H-furan-2-one;

3-(3-chloro-4-methoxyphenoxy)-5,5-dimethyl-4-(4-methylsulfonyl)phenyl-5H-furan-2-one;

(5R)-3-(3-chloro-4-methoxyphenoxy)-5-ethyl-5-methyl-4-(4-methylsulfonyl)phenyl-5H-furan-2-one;

(5R)-3-(4-chlorophenoxy)-5-trifluoroethyl-5-methyl-4-(4-methylsulfonyl)phenyl-5H-furan-2-one;

(5R)-3-(4-bromophenoxy)-5-trifluoroethyl-5-methyl-4-(4-methylsulfonyl)phenyl-5H-furan-2-one;

5-cyclopropylmethyl-3-(3,4-difluorophenoxy)-5-methyl-(4-methylsulfonyl)phenyl-5H-furan-2-one;

(5R)-3-(3-fluorophenoxy)-5-ethyl-5-methyl-4-(4-methylsulfonyl)phenyl-5H-furan-2-one;

(5R)-3-(4-chloro-3-fluorophenoxy)-5-ethyl-5-methyl-4-(4-methylsulfonyl)phenyl-5H-furan-2-one;

(5R)-3-phenoxy-5-ethyl-5-methyl-4-(4-methylsulfonyl)phenyl-5H-furan-2-one;

(5R)-3-(4-chloro-3-methylphenoxy)-5-ethyl-5-methyl-4-(4-methylsulfonyl)phenyl-5H-furan-2-one;

3-(4-chloro-3-methylphenoxy)-5-5-dimethyl-4-(4-methylsulfonyl)phenyl-5H-furan-2-one;

(5R)-3-(5-bromo-2-pyridyloxy)-4-(4-methylsulfonylphenyl)-5-methyl-5-(2,2,2-trifluoroethyl)-5H-furan-2-one;

(5R)-3-(5-bromo-2-pyridyloxy)-4-(4-methylsulfonylphenyl)-5-ethyl-5-methyl-5H-furan-2-one;

3-(5-chloro-6-methyl-2-pyridyloxy)-5,5-dimethyl-4-(4-methylsulfonyl)phenyl-5H-furan-2-one;

3-(5-cyclopropyl-2-pyridyloxy)-5,5-dimethyl-4-(4-methylsulfonyl)phenyl-5H-furan-2-one;

3-(1-cyclopropylethoxy)-4-(4-methylsulfonyl)phenyl-5H-furan-2-one; and 3-(cyclopropylmethoxy)-4-(4-methylsulfonyl)phenyl-5H-furan-2-one;

or a pharmaceutically acceptable salt or stereoisomer thereof.

Inhibitors of COX-2 that are particularly useful in the instant method of treatment are:
3-phenyl-4-(4-(methylsulfonyl)phenyl)-2-(5H)-furanone; and

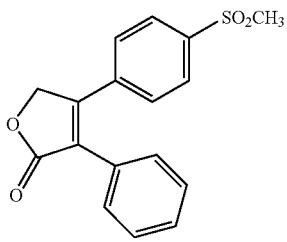

5-chloro-3-(4-methylsulfonyl)phenyl-2-(2-methyl-5-pyridinyl)pyridine;

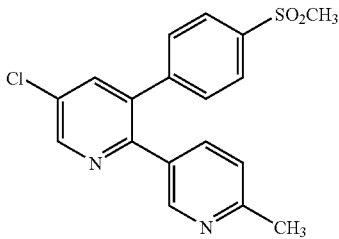

or a pharmaceutically acceptable salt thereof.

General and specific synthetic procedures for the preparation of the COX-2 inhibitor compounds described above are found in U.S. Pat. No. 5,474,995, issued Dec. 12, 1995, U.S. Pat. No. 5,861,419, issued Jan. 19, 1999, and U.S. Pat. No. 6,001,843, issued Dec. 14, 1999, all of which are herein incorporated by reference.

Compounds that have been described as specific inhibitors of COX-2 and are therefore useful in the present invention include, but are not limited to, the following:

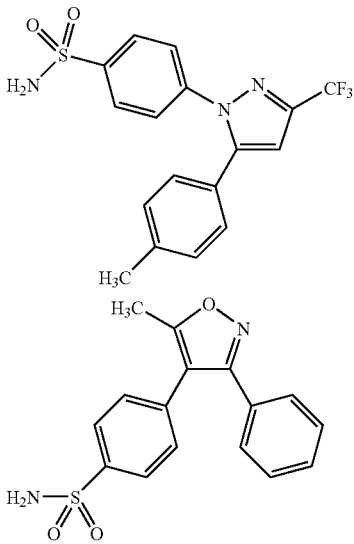

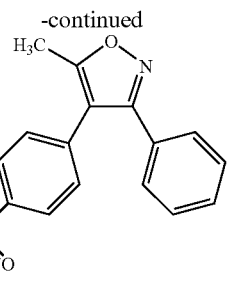

or a pharmaceutically acceptable salt thereof.

Compounds which are described as specific inhibitors of COX-2 and are therefore useful in the present invention, and methods of synthesis thereof, can be found in the following patents, pending applications and publications, which are herein incorporated by reference: WO 94/15932, published Jul. 21, 1994, U.S. Pat. No. 5,344,991, issued Jun. 6, 1994, U.S. Pat. No. 5,134,142, issued Jul. 28, 1992, U.S. Pat. No. 5,380,738, issued Jan. 10, 1995, U.S. Pat. No. 5,393,790, issued Feb. 20, 1995, U.S. Pat. No. 5,466,823, issued Nov. 14, 1995, U.S. Pat. No. 5,633,272, issued May 27, 1997, and U.S. Pat. No. 5,932,598, issued Aug. 3, 1999.

Compounds which are specific inhibitors of COX-2 and are therefore useful in the present invention, and methods of synthesis thereof, can be found in the following patents, pending applications and publications, which are herein incorporated by reference: U.S. Pat. No. 5,474,995, issued Dec. 12, 1995, U.S. Pat. No. 5,861,419, issued Jan. 19, 1999, U.S. Pat. No. 6,001,843, issued Dec. 14, 1999, U.S. Pat. No. 6,020,343, issued Feb. 1, 2000, U.S. Pat. No. 5,409,944, issued Apr. 25, 1995, U.S. Pat. No. 5,436,265, issued Jul. 25, 1995, U.S. Pat. No. 5,536,752, issued Jul. 16, 1996, U.S. Pat. No. 5,550,142, issued Aug. 27, 1996, U.S. Pat. No. 5,604,260, issued Feb. 18, 1997, U.S. Pat. No. 5,698,584, issued Dec. 16, 1997, and U.S. Pat. No. 5,710,140, issued Jan. 20, 1998.

Other examples of angiogenesis inhibitors include, but are not limited to, endostation, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonyl-imino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha_v\beta_5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

The instant compounds are also useful, alone or in combination with platelet fibrinogen receptor (GP IIb/IIIa) antagonists, such as tirofiban, to inhibit metastasis of cancerous cells. Tumor cells can activate platelets largely via thrombin generation. This activation is associated with the release of VEGF. The release of VEGF enhances metastasis by increasing extravasation at points of adhesion to vascular endothelium (Amirkhosravi, *Platelets* 10, 285–292, 1999). Therefore, the present compounds can serve to inhibit metastasis, alone or in combination with GP IIb/IIIa antagonists. Examples of other fibrinogen receptor antagonists include abciximab, eptifibatide, sibrafiban, lamifiban, lotrafiban, cromofiban, and CT50352.

If formulated as a fixed dose, such combination products employ the compounds of this invention within the dosage range described below and the other pharmaceutically active agent(s) within its approved dosage range. Compounds of the instant invention may alternatively be used sequentially with known pharmaceutically acceptable agent(s) when a combination formulation is inappropriate.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's bloodstream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

The scope of the invetion therefore encompasses the use of the instantly claimed compounds in combination with a second compound selected from:
1) an estrogen receptor modulator,
2) an androgen receptor modulator,
3) retinoid receptor modulator,
4) a cytotoxic agent,
5) an antiproliferative agent,
6) a prenyl-protein transferase inhibitor,
7) an HMG-CoA reductase inhibitor,
8) an HIV protease inhibitor,
9) a reverse transcriptase inhibitor, and
10) another angiogenesis inhibitor.

Preferred angiogenesis inhibitors to be useed as the second compound are a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interferon-α, interleukin-12, pentosan polysulfate, a cyclooxygenase inhibitor, carboxyamido-triazole, combretastatin A-4, squalamine, 6-O-chloroacetyl-carbonyl)-fumagillol, thalidomide, angiostatin, troponin-1, or an antibody to VEGF. Preferred estrogen receptor modulators are tamoxifen and raloxifene.

Also included in the scope of the claims is a method of treating cancer that comprises administering a therapeutically effective amount of a compound of Formula I in combination with radiation therapy and/or in combination with a compound selected from:
1) an estrogen receptor modulator,
2) an androgen receptor modulator,
3) retinoid receptor modulator,
4) a cytotoxic agent,
5) an antiproliferative agent,
6) a prenyl-protein transferase inhibitor,
7) an HMG-CoA reductase inhibitor,
8) an MV protease inhibitor,
9) a reverse transcriptase inhibitor, and
10) another angiogenesis inhibitor.

And yet another embodiment of the invention is a method of treating cancer that comprises administering a therapeutically effective amount of a compound of Formula I in combination with paclitaxel or trastuzumab.

The invention further encompasses a method of treating or preventing cancer that comprises administering a therapeutically effective amount of a compound of Formula I in combination with a COX-2 inhibitor.

These and other aspects of the invention will be apparent from the teachings contained herein.

Assays

The compounds of the instant invention described in the Examples were tested by the assays described below and were found to have kinase inhibitory activity. Other assays are known in the literature and could be readily performed by those of skill in the art (see, for example, Dhanabal et al., Cancer Res. 59:189–197; Xin et al., J. Biol. Chem. 274: 9116–9121; Sheu et al., Anticancer Res. 18:4435–4441; Ausprunk et al., Dev. Biol. 38:237–248; Gimbrone et al., J. Natl. Cancer Inst. 52:413–427; Nicosia et al., In Vitro 18:538–549).

I. VEGF Receptor Kinase Assay

VEGF receptor kinase activity is measured by incorporation of radio-labeled phosphate into polyglutamic acid, tyrosine, 4:1 (pEY) substrate. The phosphorylated pEY product is trapped onto a filter membrane and the incorporation of radio-labeled phosphate quantified by scintillation counting.

Materials

VEGF Receptor Kinase

The intracellular tyrosine kinase domains of human KDR (Terman, B. I. et al. Oncogene (1991) vol. 6, pp. 1677–1683.) and Flt-1 (Shibuya, M. et al. Oncogene (1990) vol. 5, pp. 519–524) were cloned as glutathione S-transferase (GST) gene fusion proteins. This was accomplished by cloning the cytoplasmic domain of the KDR kinase as an in frame fusion at the carboxy terminus of the GST gene. Soluble recombinant GST-kinase domain fusion proteins were expressed in *Spodoptera frugiperda* (Sf21) insect cells (Invitrogen) using a baculovirus expression vector (pAcG2T, Pharmingen).

The other materials used and their compositions were as follows:

Lysis buffer: 50 mM Tris pH 7.4, 0.5 M NaCl, 5 mM DTT, 1 mM EDTA, 0.5% triton X-100, 10% glycerol, 10 mg/mL of each leupeptin, pepstatin and aprotinin and 1 mM phenylmethylsulfonyl fluoride (all Sigma).

Wash buffer: 50 mM Tris pH 7.4, 0.5 M NaCl, 5 mM DTT, 1 mM EDTA, 0.05% triton X-100, 10% glycerol, 10 mg/mL of each leupeptin, pepstatin and aprotinin and 1 mM phenylmethylsulfonyl fluoride.

Dialysis buffer: 50 mM Tris pH 7.4, 0.5 M NaCl, 5 mM DTT, 1 mM EDTA, 0.05% triton X-100, 50% glycerol, 10 mg/mL of each leupeptin, pepstatin and aprotinin and 1 mM phenylmethylsuflonyl fluoride.

10× reaction buffer: 200 mM Tris, pH 7.4, 1.0 M NaCl, 50 mM $MnCl_2$, 10 mM DTT and 5 mg/mL bovine serum albumin (Sigma).

Enzyme dilution buffer: 50 mM Tris, pH 7.4, 0.1 M NaCl, 1 mM DTT, 10% glycerol, 100 mg/mL BSA.

10× Substrate: 750 μg/mL poly (glutamic acid, tyrosine; 4:1) (Sigma).

Stop solution: 30% trichloroacetic acid, 0.2 M sodium pyrophosphate (both Fisher).

Wash solution: 15% trichloroacetic acid, 0.2 M sodium pyrophosphate.

Filter plates: Millipore #MAFC NOB, GF/C glass fiber 96 well plate.

Method

A. Protein Purification

1. Sf21 cells were infected with recombinant virus at a multiplicity of infection of 5 virus particles/cell and grown at 27° C. for 48 hours.

2. All steps were performed at 4° C. Infected cells were harvested by centrifugation at 1000×g and lysed at 4° C. for 30 minutes with 1/10 volume of lysis buffer followed by centrifugation at 100,000×g for 1 hour. The supernatant was then passed over a glutathione Sepharose column (Pharmacia) equilibrated in lysis buffer and washed with 5 volumes of the same buffer followed by 5 volumes of wash buffer. Recombinant GST-KDR protein was eluted with wash buffer/10 mM reduced glutathione (Sigma) and dialyzed against dialysis buffer.

B. VEGF Receptor Kinase Assay

1. Add 5 μl of inhibitor or control to the assay in 50% DMSO.

2. Add 35 μl of reaction mix containing 5 μl of 10× reaction buffer, 5 μl 25 mM ATP/10 μCi [$^{33}$P]ATP (Amersham), and 5 μl 10× substrate.

3. Start the reaction by the addition of 10 μl of KDR (25 nM) in enzyme dilution buffer.

4. Mix and incubate at room temperature for 15 minutes.

5. Stop by the addition of 50 μl stop solution.

6. Incubate for 15 minutes at 4° C.

7. Transfer a 90 μl aliquot to filter plate.

8. Aspirate and wash 3 times with wash solution.

9. Add 30 μl of scintillation cocktail, seal plate and count in a Wallac Microbeta scintillation counter.

II. Human Umbilical Vein Endothelial Cell Mitogenesis Assay

Human umbilical vein endothelial cells (HUVECs) in culture proliferate in response to VEGF treatment and can be used as an assay system to quantify the effects of KDR kinase inhibitors on VEGF stimulation. In the assay described, quiescent HUVEC monolayers are treated with vehicle or test compound 2 hours prior to addition of VEGF or basic fibroblast growth factor (bFGF). The mitogenic response to VEGF or bFGF is determined by measuring the incorporation of [$^3$H]thymidine into cellular DNA.

Materials

HUVECs: HUVECs frozen as primary culture isolates are obtained from Clonetics Corp. Cells are maintained in Endothelial Growth Medium (EGM; Clonetics) and are used for mitogenic assays described in passages 3–7 below.

Culture Plates: NUNCLON 96-well polystyrene tissue culture plates (NUNC #167008).

Assay Medium: Dulbecco's modification of Eagle's medium containing 1 g/mL glucose (low-glucose DMEM; Mediatech) plus 10% (v/v) fetal bovine serum (Clonetics).

Test Compounds: Working stocks of test compounds are diluted serially in 100% dimethylsulfoxide (DMSO) to 400-fold greater than their desired final concentrations. Final dilutions to 1× concentration are made directly into Assay Medium immediately prior to addition to cells.

10× Growth Factors: Solutions of human $VEGF_{165}$ (500 ng/mL; R&D Systems) and bFGF (10 ng/mL; R&D Systems) are prepared in Assay Medium.

10× [$^3$H]Thymidine: [Methyl-$^3$H]thymidine (20 Ci/mmol; Dupont-NEN) is diluted to 80 μCi/mL in low-glucose DMEM.

Cell Wash Medium: Hank's balanced salt solution (Mediatech) containing 1 mg/mL bovine serum albumin (Boehringer-Mannheim).

Cell Lysis Solution: 1 N NaOH, 2% (w/v) $Na_2CO_3$.

Method

1. HUVEC monolayers maintained in EGM are harvested by trypsinization and plated at a density of 4000 cells per 100 µL Assay Medium per well in 96-well plates. Cells are growth-arrested for 24 hours at 37° C. in a humidified atmosphere containing 5% $CO_2$.

2. Growth-arrest medium is replaced by 100 µL Assay Medium containing either vehicle (0.25% [v/v] DMSO) or the desired final concentration of test compound. All determinations are performed in triplicate. Cells are then incubated at 37° C. with 5% $CO_2$ for 2 hours to allow test compounds to enter cells.

3. After the 2-hour pretreatment period, cells are stimulated by addition of 10 µL/well of either Assay Medium, 10×VEGF solution or 10×bFGF solution. Cells are then incubated at 37° C. and 5% $CO_2$.

4. After 24 hours in the presence of growth factors, 10× [$^3$H]thymidine (10 µL/well) is added.

5. Three days after addition of [$^3$H]thymidine, medium is removed by aspiration, and cells are washed twice with Cell Wash Medium (400 µL/well followed by 200 µL/well). The washed, adherent cells are then solubilized by addition of Cell Lysis Solution (100 µL/well) and warming to 37° C. for 30 minutes. Cell lysates are transferred to 7-mL glass scintillation vials containing 150 µL of water. Scintillation cocktail (5 mL/vial) is added, and cell-associated radioactivity is determined by liquid scintillation spectroscopy.

Based upon the foregoing assays the compounds of the present invention are inhibitors of VEGF and thus are useful for the inhibition of angiogenesis, such as in the treatment of ocular disease, e.g., diabetic retinopathy and in the treatment of cancers, e.g., solid tumors. The instant compounds inhibit VEGF-stimulated mitogenesis of human vascular endothelial cells in culture with $IC_{50}$ values between 0.01–5.0 µM. These compounds may also show selectivity over related tyrosine kinases (e.g., FGFR1 and the Src family; for relationship between Src kinases and VEGFR kinases, see Eliceiri et al., Molecular Cell, Vol. 4, pp. 915–924, December 1999).

III. FLT-1 Kinase Assay

Flt-1 was expressed as a GST fusion to the Flt-1 kinase domain and was expressed in baculovirus/insect cells. The following protocol was employed to assay compounds for Flt-1 kinase inhibitory activity:

1. Inhibitors were diluted to account for the final dilution in the assay, 1:20.
2. The appropriate amount of reaction mix was prepared at room temperature:
   10× Buffer (20 mM Tris pH 7.4/0.1 M NaCl/1 mM DTT final)
   0.1M $MnCl_2$ (5 mM final)
   pEY substrate (75 µg/mL)
   ATP/[$^{33}$P]ATP (2.5 µM/1 µCi final)
   BSA (500 µg/mL final).
3. 5 µL of the diluted inhibitor was added to the reaction mix. (Final volume of 5 µL in 50% DMSO). To the positive control wells, blank DMSO (50%) was added.
4. 35 µL of the reaction mix was added to each well of a 96 well plate.
5. Enzyme was diluted into enzyme dilution buffer (kept at 4° C.).
6. 10 µL of the diluted enzyme was added to each well and mix (5 nM final).
To the negative control wells, 10 µL 0.5 M EDTA was added per well instead (final 100 mM).

7. Incubation was then carried out at room temperature for 30 minutes.
8. Stopped by the addition of an equal volume (50 µL) of 30% TCA/0.1M Na pyrophosphate.
9. Incubation was then carried out for 15 minutes to allow precipitation.
10. Transfered to Millipore filter plate.
11. Washed 3× with 15% TCA/0.1M Na pyrophosphate (125 µL per wash).
12. Allowed to dry under vacuum for 2–3 minutes.
13. Dried in hood for ~20 minutes.
14. Assembled Wallac Millipore adapter and added 50 µL of scintillant to each well and counted.

IV. FLT-3 Kinase Assay

Flt-3 was expressed as a GST fusion to the Flt-3 kinase domain, and was expressed in baculovirus/insect cells. The following protocol was employed to assay compounds for Flt-3 kinase inhibitory activity:

1. Dilute inhibitors (account for the final dilution into the assay, 1:20)
2. Prepare the appropriate amount of reaction mix at room temperature.
   10× Buffer (20 mM Tris pH 7.4/0.1 M NaCl/1 mM DTT final)
   0.1M $MnCl_2$ (5 mM final)
   pEY substrate (75 µg/mL)
   ATP/[$^{33}$P]ATP (0.5 µM/L µCi final)
   BSA (500 µg/mL final)
3. Add 5 µL of the diluted inhibitor to the reaction mix. (Final volume of 5 µL in 50% DMSO). Positive control wells—add blank DMSO (50%).
4. Add 35 µL of the reaction mix to each well of a 96 well plate.
5. Dilute enzyme into enzyme dilution buffer (keep at 4° C.).
6. Add 10 µL of the diluted enzyme to each well and mix (5–10 nM final).
Negative control wells—add 10 µL 0.5 M EDTA per well instead (final 100 mM)
7. Incubate at room temperature for 60 min.
8. Stop by the addition of an equal volume (50 µL) of 30% TCA/0.1M Na pyrophosphate.
9. Incubate for 15 min to allow precipitation.
10. Transfer to Millipore filter plate.
11. Wash 3× with 15% TCA/0.1M Na pyrophosphate (125 µL per wash).
12. Allow to dry under vacuum for 2–3 min.
13. Dry in hood for ~20 min.
14. Assemble Wallac Millipore adapter and add 50 µL of scintillant to each well and count.

EXAMPLES

Examples provided are intended to assist in a further understanding of the invention. Particular materials employed, species and conditions are intended to be illustrative of the invention and not limiting of the reasonable scope thereof.

Example 1

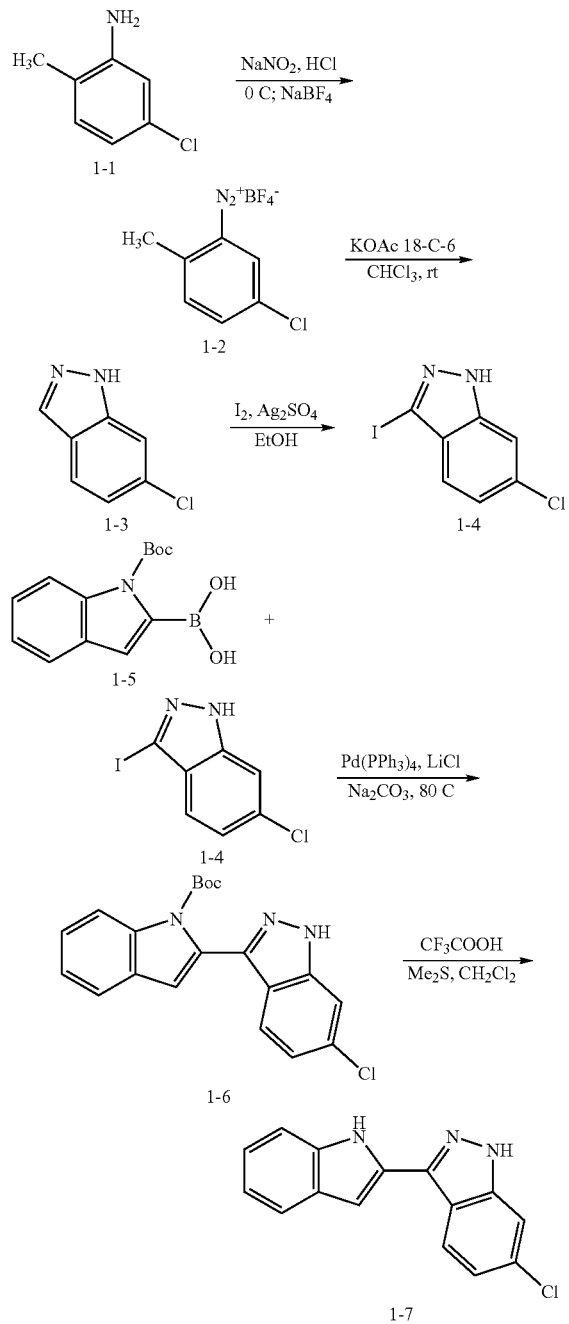

Step 1: 6-chloroindazole (1-3b)

A slurry of 5-chloro-2-methylaniline (1-1, 30 g, 0.21 mol) in water (200 mL) was treated with HCl (12N, 53 mL, 0.64 mol). The resulting solution was cooled to 0° C. and reacted with aqueous solution of sodium nitrite (14.6 g, 0.21 mol). After 30 min. stirring, any insoluble particles were removed by filtration and the filtrate solution was treated at 0° C. with sodium tetrafluoroborate dissolved in water (150 mL). Precipitates so formed was collected by filtration, washed with ice-cold water, cold methanol and then with ethylether. The product (1-2) was dried in vacuo and then suspended in chloroform (500 mL) in the presence of potassium acetate (34 g, 0.35 mol) and 18-crown-6 (2.29 g, 8.67 mmol). The reaction mixture was stirred at the ambient temperature for 1.5 h, partitioned between ethyl acetate and water. The organic layer was washed with brine, separated, dried (MgSO$_4$) and concentrated in vacuo. Trituation with dichloromethane and hexanes afforded the desired product as an orange powder (1-3); $^1$H NMR (400 MHz, DMSO-d$_6$) δ 13.18 (bs, 1H), 8.11 (s, 1H), 7.79 (d, 1H, J=8.7 Hz), 7.62 (s, 1H), 7.13 (dd, 1H, J=7.9, 1.9 Hz).

Step 2: 6-chloro-3-iodoindazole (1-4)

A solution of 6-chloroindazole (1-3, 5.24 g, 34.3 mmol) in ethanol (500 mL) was reacted at the ambient temperature with iodine (8.72 g, 34.3 mmol) in the presence of silver sulfate (10.7 g, 34.3 mmol). After 2 h stirring at the same temperature, all the precipitates were removed by filtration and the filtrate solution was concentrated in vacuo. Trituation with dichloromethane and hexanes gave the desired product as an orange solid (1-4); $^1$H NMR (400 MHz, DMSO-d$_6$) δ 13.62 (bs, 1H), 7.66 (d, 1H, J=1.6 Hz), 7.46 (d, 1H, J=8.5 Hz), 7.21 (dd, 1H, J=8.6, 1.6 Hz).

Step 3: N-tert-butyloxycarbonylindole-2-boronic Acid (1-5)

A stirred solution of indole (8.2 g; 70 mmol) in CH$_2$Cl$_2$ (200 mL) was reacted with di-tert-butyl dicarbonate (18.3 g; 84 mmol) in the presence of N,N-dimethylaminopyridine (430 mg; 3.5 mmol). The reaction mixture was stirred overnight, concentrated in vacuo. The resulting crude product was diluted with tetrahydrofuran (200 mL), cooled to −78° C. and treated with 3M-lithuim diisopropylamide (35 mL; 105 mmol). After 2 h stirring at the same temperature, the reaction mixture was quenched with trimethylborate (23.8 mL; 210 mmol), warmed to room temperature and partitioned between ethyl acetate and 0.3N-HCl. The organic layer was washed with brine, separated, dried (MgSO$_4$) and concentrated in vacuo. Trituation of the solid with hexanes and filtration afforded the desired product as a pale tan solid (1-5); $^1$H NMR (300 MHz, DMSO-d$_6$) δ 8.18 (bs, 2H), 8.07 (d, 1H, J=8.1 Hz), 7.54 (d, 1H, J=7.5 Hz), 7.26 (t, 1H, J=7.5 Hz), 7.17 (t, 1H, J=7.8 Hz), 6.61 (s, 1H), 1.59 (s, 9H).

Step 4: 6-Chloro-3-(1H-indol-2-yl)-1H-indazole (1-7)

A biphasic reaction mixture of the iodide (1-4, 1.2 g, 4.31 mmol), the boronic acid (1-5, 1.35 g, 5.17 mmol), tetrakis(triphenylphosphine)palladium(0) (200 mg, 0.17 mmol), lithium chloride (548 mg, 12.9 mmol), and Na$_2$CO$_3$ (2M, 3 mL) in dioxane (9 mL) was heated at 70° C. for 2 h under the nitrogen atmosphere. The reaction mixture was partitioned between ethyl acetate and water. The organic layer was washed with brine, separated, dried (MgSO$_4$) and concentrated in vacuo. Chromatography (SiO$_2$, 33% ethyl acetate in hexanes) followed by concentration afforded 1-6 as a pale brown solid. The intermediate, 1-6, was dissolved in dichloromethane (6 mL) and treated at the ambient temperature with trifluoroacetic acid (6 mL) in the presence of dimethyl sulfide (0.05 mL) and water (0.05 mL). After 3 h stirring, the reaction mixture was concentrated in vacuo and partitioned between ethyl acetate and saturated aqueous sodium bicarbonate solution. The organic layer was separated, dried (MgSO$_4$), and concentrated in vacuo. Chromatography (SiO$_2$, 33% ethyl acetate in hexanes) followed by concentration afforded 1-7 as a pale brown solid.; $^1$H NMR (400 MHz, CDCl$_3$) δ 10.34 (bs, 1H), 9.73 (bs, 1H), 8.15 (d, 1H, J=7.9 Hz), 7.71 (d, 1H, J=7.8 Hz), 7.66 (d, 1H, J=1.6 Hz), 7.46 (d, 1H, J=8.5 Hz), 7.30 (t, 1H, J=7.5 Hz), 7.21 (dd, 1H, J=8.6, 1.6 Hz), 7.24 (t, 1H, J=7.8 Hz), 7.16 (s, 1H).

3-(1H-Indol-2-yl)-1H-indazole (1-8)

Compound 1-8 was prepared by the same chemical transformations shown in Scheme 1 (1-3 to 1-7), but substituting 2-methylaniline for the 2-methyl 5-chloroaniline in Step 1; $^1$H NMR (400 MHz, CDCl$_3$) δ 10.17 (bs, 1H), 9.22 (bs, 1H), 8.15 (d, 1H, J=7.9 Hz), 7.71 (d, 1H, J=7.8 Hz), 7.50 (t, 1H, J=7.7 Hz), 7.46 (t, 1H, J=7.8 Hz), 7.42 (d, 1H, J=7.7 Hz), 7.30 (t, 1H, J=7.5 Hz), 7.24 (t, 1H, J=7.8 Hz), 7.16 (s, 1H), 7.14 (d, 1H, J=7.7 Hz).

Compounds in Table 1 were prepared as shown in Scheme 1, but substituting the appropriate substituted 2-methylaniline for the 5-chloro-2-methylaniline in Step 1:

TABLE 1

| # | Structure | Nomenclature and Spectral Data |
|---|---|---|
| 1-9 | 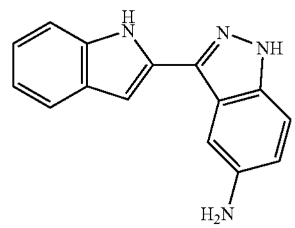 | 3-(1H-Indol-2-yl)-1H-indazol-5-ylamine<br>$^1$H NMR(400 MHz, DMSO-d$_6$)δ 13.27(s, 1H), 12.34(s, 1H), 8.24(d, 1H, J=7.8Hz), 7.76(s, 1H), 7.63(d, 1H, J=7.6Hz), 7.42(d, 1H, J=8.5 Hz), 7.33(t, 1H, J=7.8Hz), 7.25(t, 1H, J=7.7 Hz), 6.70(s, 1H), 6.39(d, 1H, J=8.6Hz). |
| 1-10 | 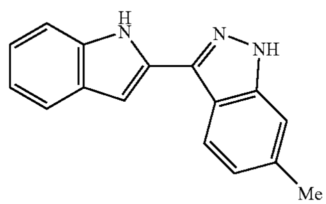 | 3-(1H-Indol-2-yl)-6-methyl-1H-indazole<br>MS(M+1)=248. $^1$H NMR(400 MHz, CDCl$_3$) δ 10.34(bs, 1H), 9.73(bs, 1H), 8.36(d, 1H, J=7.9Hz), 7.71(d, 1H, J=7.8Hz), 7.61(s, 1H), 7.46(d, 1H, J=8.5Hz), 7.33(t, 1H, J=7.5Hz), 7.24(d, 1H, J=8.6Hz), 7.24(t, 1H, J=7.8 Hz), 7.06(s, 1H), 2.57(s, 3H). |
| 1-11 | 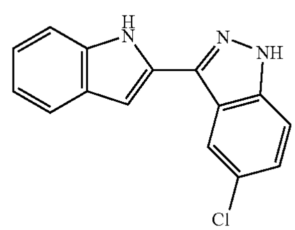 | 3-(1H-Indol-2-yl)-4-chloro-1H-indazole<br>MS(M+1)=267. $^1$H NMR(400 MHz, CDCl$_3$) δ 11.23(s, 1H), 9.06(bs, 1H), 8.11(s, 1H), 7.71 (d, 1H, J=8.0Hz), 7.46(d, 1H, J=8.2Hz), 7.47–7.41(m, 3H), 7.25(t, 1H, J=8.0Hz), 7.12(s, 1H). |
| 1-12 | 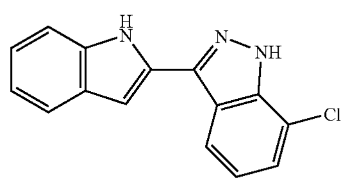 | 3-(1H-Indol-2-yl)-7-chloro-1H-indazole<br>MS(M+1)=267. $^1$H NMR(400 MHz, DMSO-d$_6$) δ 13.88(s, 1H), 11.63(s, 1H), 8.19(d, 1H, J=9.7Hz), 7.60(d, 1H, J=9.0Hz), 7.54(d, 1H, J=8.9Hz), 7.46(d, 1H, J=9.6Hz), 7.26(t, 1H, J=9.3Hz), 7.16(s, 1H), 7.12(t, 1H, J=9.2Hz), 7.02(t, 1H, J=9.2Hz). |
| 1-13 | 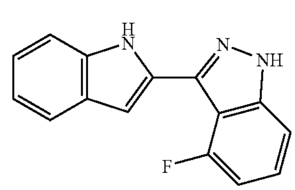 | 3-(1H-Indol-2-yl)-4-fluoro-1H-indazole<br>MS(M+1)=251. $^1$H NMR(400 MHz, DMSO-d$_6$) δ 13.60(s, 1H), 11.53(s, 1H), 7.59(d, 1H, J=6.6Hz), 7.50–7.36(m, 3H), 7.14–6.95(m, 5H). |
| 1-14 | 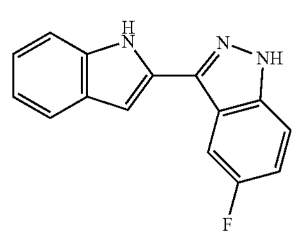 | 3-(1H-Indol-2-yl)-5-fluoro-1H-indazole<br>MS(M+1)=251. $^1$H NMR(400 MHz, DMSO-d$_6$) δ 13.41(s, 1H), 11.57(s, 1H), 7.97(d, 1H, J=9.1Hz), 7.64(dd, 1H, J=8.6, 2.4Hz), 7.58(d, 1H, J=7.7Hz), 7.45(d, 1H, J=7.7Hz), 7.34(dt, 1H, J=9.1, 1.4 Hz), 7.14(s, 1H), 7.11(t, 1H, J=7.7Hz), 7.02(t, 1H, J=7.7Hz) |

TABLE 1-continued

| # | Structure | Nomenclature and Spectral Data |
|---|---|---|
| 1-15 | 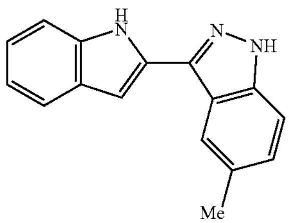 | 3-(1H-Indol-2-yl)-5-methyl-1H-indazole<br>MS(M+1)=248. $^1$H NMR(400 MHz, DMSO-d$_6$) δ 13.13(s, 1H), 11.50(s, 1H), 7.94(s, 1H), 7.58(d, 1H, J=7.5Hz), 7.49 (d, 1H, J=7.8Hz), 7.44(d, 1H, J=7.8 Hz), 7.27(d, 1H, J=7.5Hz), 7.20–7.75(m, 3H), 2.52(s, 3H). |
| 1-16 | 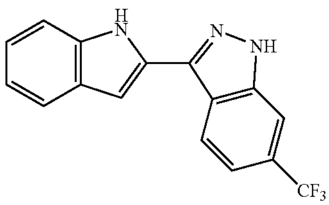 | 3-(1H-Indol-2-yl)-6-trifluoromethyl-1H-indazole<br>MS(M+1)=301. $^1$H NMR(400 MHz, DMSO-d$_6$) δ 13.77(s, 1H), 11.65(s, 1H), 7.94(s, 1H), 8.85(d, 1H, J=8.5Hz), 8.00 (s, 1H), 7.63(d, 1H, J=7.7Hz), 7.53(d, 1H, J=7.7Hz), 7.48(d, 1H, J=8.5Hz), 7.22(s, 1H), 7.16(t, 1H, J=7.0Hz), 7.04(t, 1H, J=7.0Hz). |
| 1-17 | 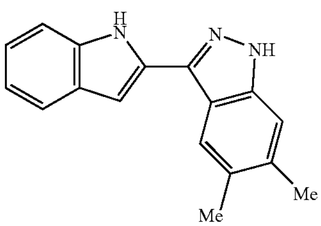 | 3-(1H-Indol-2-yl)-5,6-dimethyl-1H-indazole<br>MS(M+1)=261. $^1$NMR(400 MHz, DMSO-d$_6$) δ 13.00(s, 1H), 11.45(s, 1H), 7.94(s, 1H), 7.58(d, 1H, J=7.8Hz), 7.44 (d, 1H, J=7.8Hz), 7.37(s, 1H), 7.12–7.07 (m, 2H), 7.00(t, 1H, J=7.6Hz), 2.40(s, 3H), 2.38(s, 3H). |
| 1-18 | 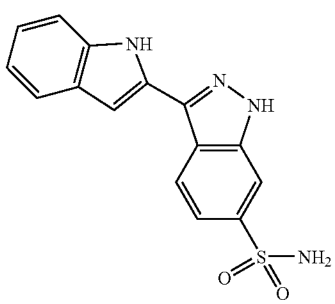 | 3-(1H-Indol-2-yl)-1H-indazole-6-sulfonic acid amide<br>$^1$H NMR(500 MHz, DMSO-d$_6$) δ 13.7(s, 1H), 11.6(s, 1H), 8.40(d, 1H, J=8.54Hz), 8.05(s, 1H), 7.68(d, 1H, J=8.5Hz), 7.61 (d, 1H, J=7.8Hz), 7.48(s, 2H), 7.46(d, 1H, J=8.3Hz), 7.20(s, 1H), 7.13(t, 1H, J=7.1Hz), 7.02(t, 1H, J=7.1Hz). |
| 1-19 | 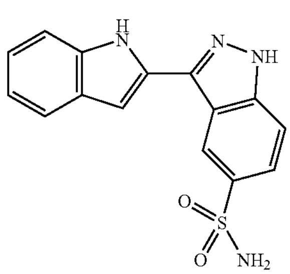 | 3-(1H-indol-2-yl)-1H-indazole-5-sulfonamide<br>$^1$H NMR(500 MHz, DMSO-d$_6$) δ 13.7(s, 1H), 11.6(s, 1H), 8.66(s, 1H), 7.87(d, 1H, J=8.8), 7.77(d, 1H, J=8.8Hz), 7.65(d, 1H, J=7.8Hz), 7.46(d, 1H, J=8.8Hz), 7.40(s, 2H), 7.14(m, 2H), 7.04(t, 1H, J=8.1Hz). |
| 1-20 | 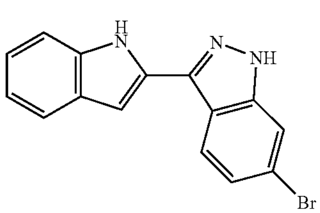 | 3-(1H-Indol-2-yl)-6-bromo-1H-indazole; NMR(300 MHz, CDCl$_3$) δ 11.20(bs, 1H), 9.47(bs, 1H), 8.31(d, 1H, J=8.1Hz), 7.64 (d, 1H, J=7.8Hz), 7.52–7.50(m, 2H), 7.42(dt, 1H, J=7.2, 1.5Hz), 7.32–7.26(m, 3H), 6.89(s, 1H), 7.14(d, 1H, J=7.7Hz). |

TABLE 1-continued

| # | Structure | Nomenclature and Spectral Data |
|---|---|---|
| 1-21 | 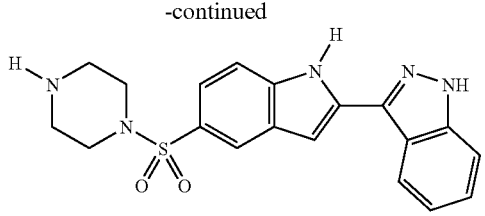 | 3-(1H-Indol-2-yl)-1H-indazole-6-carbonitrile; $^1$H NMR(300 MHz, DMSO-d$_6$) δ 13.90(s, 1H), 11.70(s, 1H), 8.42(d, 1H, J=8.1Hz), 8.25(s, 1H), 7.60(s, 1H), 7.59(t, 1H, J=8.7Hz), 7.46(d, 1H, J=8.1Hz), 7.21(d, 1H, J=1.5Hz), 7.14(dt, 1H, J=8.1, 1.0Hz), 7.03(dt, 1H, J=7.8, 1.0Hz). |

Example 2

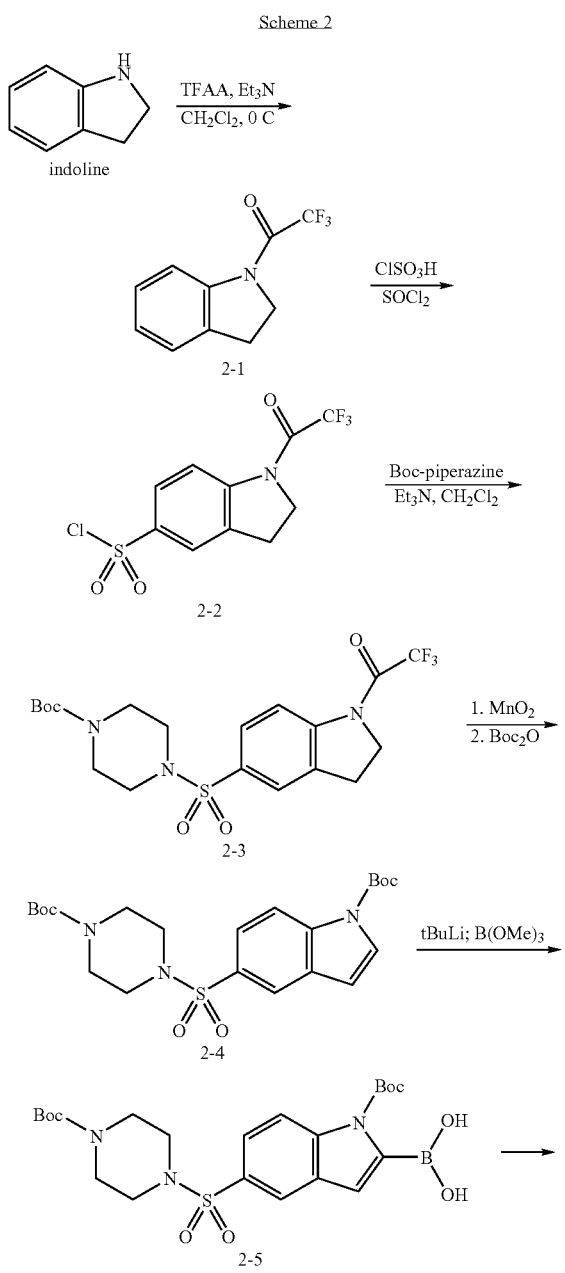

Step 1: 1-(Trifluoroacetyl)indoline (2-1)

To a solution of indoline (30 g, 251.74 mmol) and triethylamine (70.18 mL, 503.48 mmol) in methylene chloride (500 mL) cooled to 0° C. was added trifluoroacetic anhydride (53.34 mL, 377.61 mmol) dropwise over 20 minutes. The reaction mixture was warmed to room temperature and stirred for 30 minutes. The solution was washed once with saturated aqueous NaHCO$_3$ (500 mL), dried over Na$_2$SO$_4$, then concentrated in vacuo. The resulting solid was suspended in hexanes and collected by filtration. The solid was vacuum dried to afford 1-(trifluoroacetyl)indoline; $^1$H NMR (500 MHz, CDCl$_3$) δ 8.22 (d, 1H, J=8.54 Hz), 7.27 (m, 2H), 7.16 (t, 1H, J=7.5 Hz), 4.28 (t, 2H, J=8.3 Hz), 3.27 (t, 2H, J=7.3 Hz).

Step 2: 1-(Trifluoroacetyl)indoline-5-sulfonyl chloride (2-2)

A solution of the 1-(trifluoroacetyl)indoline (2-1, 21.5 g), neat in thionyl chloride (65.59 mL, 899.24 mmol), was cooled to 0° C. and treated with chlorosulfonic acid (13.28 mL, 199.83 mmol). The solution was stirred for 50 minutes, then poured directly into a beaker of ice (3 L). The precipitate was filtered and vacuum dried to afford 1-(trifluoroacetyl)indoline-5-sulfonyl chloride (2-2) as an orange solid; $^1$H NMR (500 MHz, CDCl$_3$) δ 8.42 (d, 1H, J=8.5 Hz), 8.00 (d, 1H, J=6.7 Hz), 7.92 (s, 1H), 4.43 (t, 2H, J=8.2 Hz), 3.41 (t, 2H, J=8.2 Hz).

Step 3: tert-Butyl 4-(2,3-dihydro-1H-indol-5-ylsulfonyl)piperazine-1-carboxylate (2-3)

A solution of 1-(trifluoroacetyl)indoline-5-sulfonyl chloride (2-2, 5 g) in methylene chloride (50 mL) was treated with 4-butoxycarbonylpiperazine (5.94 g, 31.88 mmol) and stirred for 45 minutes. The brown solution was concentrated to a tan-brown solid and vacuum dried. The solid (7.4 g) was then dissolved in a mixture of 1,4-Dioxane (100 mL) and Methanol (30 mL) and treated with 1N NaOH (47.9 mL, 47.90 mmol). After stirring for 1 hour, the solution was concentrated, suspended in ethylether (130 mL) and filtered. The filtered solid was then partitioned between ethyl acetate (4×85 mL) and saturated NaCl (150 mL), dried over Na$_2$SO$_4$, and concentrated to provide the tert-butyl 4-(2,3- dihydro-1H-indol-5-ylsulfonyl)piperazine-1-carboxylate (2-3) as an off-white solid; $^1$H NMR (300 MHz, CDCl$_3$) δ 7.41 (m, 2H), 6.57 (d, 1H, J=8.9 Hz), 3.69 (t, 2H, J=8.6 Hz), 3.50 (t, 2H, J=4.9 Hz), 3.09 (t, 2H, J=8.6 Hz), 2.93 (t, 2H, J=4.9 Hz), 1.42 (s, 9H).

Step 4: tert-Butyl 5-{[4(tert-butoxycarbonyl)piperazin-1-yl]sulfonyl}-1H-indole-1-carboxylate (2-4)

A solution of tert-butyl 4-(2,3dihydro-1H-indol-5-ylsulfonyl)piperazine-1-carboxylate (2-3, 750 mg) in Methylene Chloride (50 mL) was treated with manganese dioxide (887 mg, 10.21 mmol) and stirred at reflux for 1.5 hr. An additional 5 equiv (887 mg) of manganese dioxide was added and the reaction mixture was maintained at reflux for 2 h. The mixture was cooled to room temperature and filtered through celite. The filter cake was washed with methylene chloride (30 mL), ethyl acetate (30 mL), and methanol (30 mL), and the filtrate was concentrated to a tan solid. A solution of the solid in methylene chloride (50 mL) was cooled to 0° C. and treated with di-tert butyl dicarbonate (512 mg, 2.35 mmol) and dimethyl aminopyridine (37 mg, 0.31 mmol). The solution was mixed and slowly warmed to room temperature over 24 hr. The solution was partitioned between methylene chloride (2×100 mL) and water (130 mL). The combined organics were dried over Na$_2$SO$_4$, filtered and concentrated in vacuo to afford tert-butyl 5-{[4-(tert-butoxycarbonyl)piperazin-1-yl]sulfonyl}-1H-indole-1-carboxylate (2-4) as a yellow oil; $^1$H NMR (300 MHz, CDCl$_3$) δ 8.25 (d, 1H, J=8.9 MHz), 7.94 (s, 1H), 7.67 (d, 1H, J=3.7 Hz), 7.62 (dd, 1H, J=8.9 Hz), 6.63 (d, 1H, J=3.7 Hz), 3.44 (bt, 4H), 2.91 (bt, 4H), 1.62 (s, 9H), 1.32 (s, 9H).

Step 5: 1-(tert-Butoxycarbonyl)-5-{[4-(tert-butoxycarbonyl)piperazin-1-yl]sulfonyl}-1H-indol-2-ylboronic acid (2-5)

A solution of the tert-butyl 5-{[4-(tert-butoxycarbonyl)piperazin-1-yl]sulfonyl}-1H-indole-1-carboxylate (2-4, 1.06 g) in THF (55 mL) was stirred at −78° C. and treated with t-BuLi (1.7M, 2.68 mL, 4.55 mmol). After stirring for 45 minutes, the solution was treated with trimethylborate (640 μL, 5.69 mmol). The solution was warmed to 0° C. and stirred for 10 min, then partitioned between ethyl acetate (2×100 mL) and saturated NH$_4$Cl solution (100 mL). The combined organics were dried over Na2SO4, filtered and concentrated to provide 1-(tert-butoxycarbonyl)-5-{[4-(tert-butoxycarbonyl)piperazin-1-yl]sulfonyl}-1H-indol-2-ylboronic acid (2-5) as a yellow foam. LRMS m/z: Cal'd for C$_{22}$H$_{32}$BN$_3$O$_8$S (M+H) 509.39, found 510.1.

Step 6: 3-[5-(piperazin-1-ylsulfonyl)-1H-indol-2-yl]-1H-indazole (2-6)

Compound 2-6 was prepared by the same chemical transformations shown in Scheme 1 (1-5 to 1-7), but substituting the boronic acid 2-5, prepared as described in Step 5 for the boronic acid 1-5 in Example 1, Step 4; $^1$NMR (500 MHz, CD$_3$OD) δ 11.7 (s, 1H), 8.18 (s, 1H), 8.16 (d, 1H, J=8.1 Hz), 7.67 (d, 1H, J=8.5 Hz), 7.61 (m, 2H, 7.47 (t, 1H, J=6.1 Hz), 7.29 (m, 2H), 3.31 (m, 8H).

In addition to those compounds specifically exemplified in Table 1, additional compounds in Table 2 are synthesized as shown in Scheme 1 and 2.

TABLE 2

| # | Structure | Nomenclature |
|---|---|---|
| 2-6 | 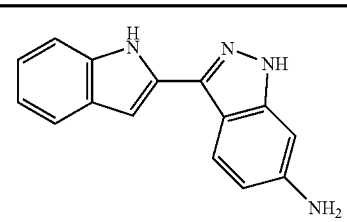 | 3-(1H-Indol-2-yl)-1H-indazol-6-ylamine |
| 2-7 | 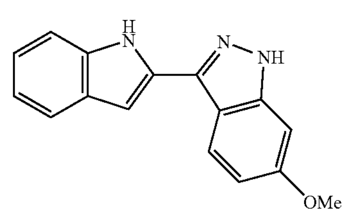 | 3-(1H-Indol-2-yl)-6-methoxy-1H-indazole |
| 2-8 | 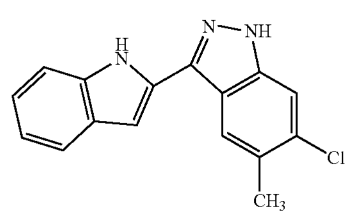 | 6-Chloro-3-(1H-indol-2-yl)-5-methyl-1H-indazole |

TABLE 2-continued

| # | Structure | Nomenclature |
|---|---|---|
| 2-9 | 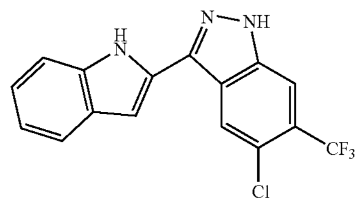 | 4-Chloro-(1H-indol-2-yl)-trifluoromethyl-1H-indazole |
| 2-10 | 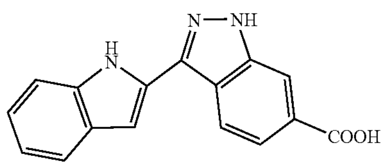 | 3-(1H-Indol-2-yl)-1H-indazole-6-carboxylic acid |
| 2-11 | 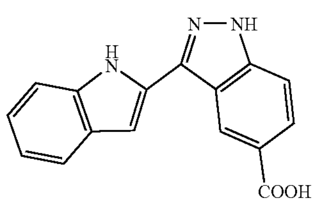 | 3-(1H-Indol-2-yl)-1H-indazole-5-carboxylic acid |
| 2-12 | 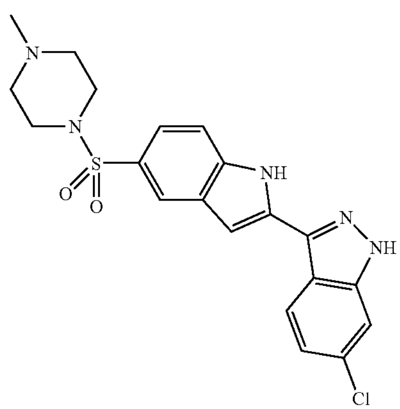 | 6-Chloro-3-[5-(4-methyl-piperazine-1-sulfonyl)-1H-indol-2-yl]-1H-indazole |
| 2-13 | 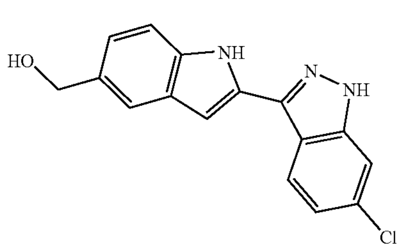 | [2-(6-Chloro-1H-indazol-3-yl)-1H-indol-5-yl]-methanol |

TABLE 2-continued

| # | Structure | Nomenclature |
|---|---|---|
| 2-14 | 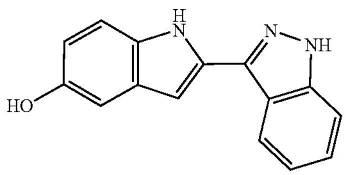 | 2-(6-Chloro-1H-indazol-3-yl)-1H-indol-5-ol |
| 2-15 | 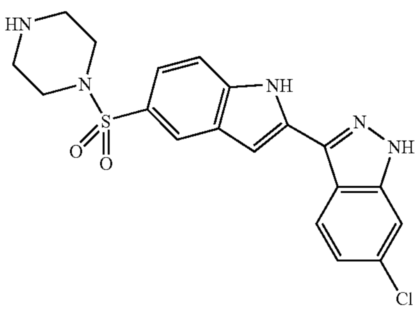 | 6-Chloro-3-[5-(piperazine-1-sulfonyl)-1H-indol-2-yl]-1H-indazole |
| 2-16 | 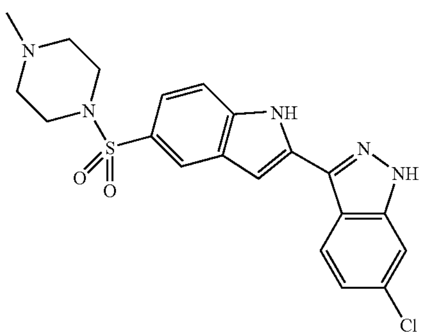 | 6-Chloro-3-[5-(4-methyl-piperazine-1-sulfonyl)-1H-indol-2-yl]-1H-indazole |
| 2-17 | 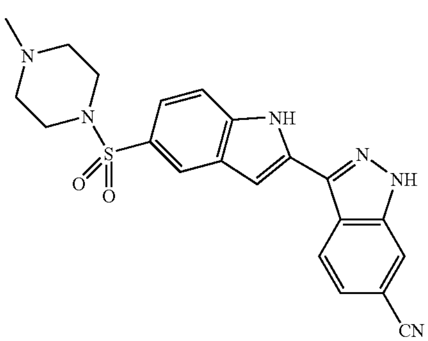 | 3-[5-(4-Methyl-piperazine-1-sulfonyl)-1H-indol-2-yl]-1H-indazole-6-carbonitrile |

Example 3

Scheme 3

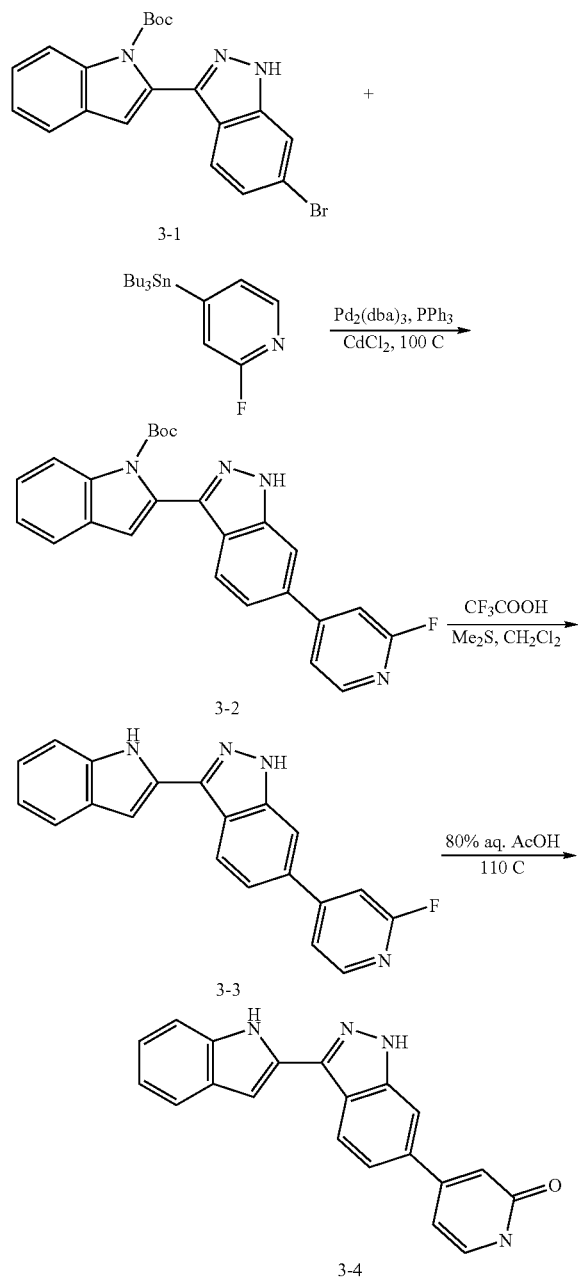

Step 1: 6-(2-Fluoro-pyridin-4-yl)-3(1H-indol-2-yl)-1H-indazole (3-3).

A solution of the 6-bromoindazole (3-1, 97 mg, 0.235 mmol), 2-fluoro-4-tributylstannanylpyridine (183 mg, 0.47 mmol), tris(dibenzylideneacetone)dipalladium(0) (8.6 mg, 0.01 mmol), triphenylphosphine (20 mg, 0.08 mmol), and cadmium chloride (22 mg, 0.12 mmol) in N-methylpyrolidinone (4 mL) was heated at 100° C. for 3 h under the nitrogen atmosphere. The reaction mixture was partitioned between ethyl acetate and water. The organic layer was washed with brine, separated, dried (MgSO₄) and concentrated in vacuo. Chromatography (SiO₂, 20% ethyl acetate in hexanes) afforded the desired intermediate (3-2). The resulting N-Boc-indole (3-2) was dissolved in dichloromethane (4 mL) and treated with trifluoroacetic acid (4 mL) in the presence of dimethylsulfide (0.05 mL) and water (0.05 ML). After 1 h stirring, the reaction mixture was concentrated in vacuo, partitioned between ethyl acetate and water. The organic layer was washed with brine, separated, dried (MgSO₄) and concentrated in vacuo. Chromatography (SiO₂, 20% ethyl acetate in hexanes) afforded the desired intermediate (3-3); $^1$H NMR (500 MHz, DMSO-$d_6$) δ 9.17 (bs, 1H), 8.31 (d, 1H, J=4.3 Hz), 8.24 (d, 1H, J=8.5 Hz), 7.72 (d, 2H, J=7.6 Hz), 7.54 (d, 1H, J=8.5 Hz), 7.45 (d, 2H, 6.4 Hz), 7.22 (m, 2H), 7.19 (t, 2H, J=7.6 Hz).

Step 2: 4-[3-(1H-Indol-2-yl)-1H-indazol-6-yl]-1H-pyridin-2-one (3-4).

A solution of the fluoropyridine (3-3, 38 mg, 0.116 mmol) in 80% acetic acid in water (13 mL) was heated at 110° C. for 10 h. The reaction mixture was concentrated in vacuo, partitioned between ethyl acetate and 0.5N-NaOH. The organic layer was washed with brine, separated, dried (MgSO₄) and concentrated in vacuo. Trituation of the crude solid with ethyl acetate afforded the desired intermediate (3-4); $^1$H NMR (500 MHz, DMSO-$d_6$) δ 13.5 (s, 1H), 11.7 (bs, 1H), 11.6 (s, 1H), 8.28 (d, 1H, J=8.6 Hz), 7.85 (s, 1H), 7.60 (d, 1H, J=7.8 Hz), 7.55 (dd, 1H, J=8.5, 1.5 Hz), 7.50 (d, 1H, J=6.8 Hz), 7.45 (d, 1H, J=8.1 Hz), 7.16 (d, 1H, J=1.9 Hz), 7.12 (dt, 1H, J=8.1, 0.98 Hz), 7.02 (t, 1H, J=1.9 Hz), 6.69 (d, 1H, J=1.9 Hz), 6.62 (dd, 1H, J=6.8, 1.7 Hz).

Example 3A

Scheme 3A

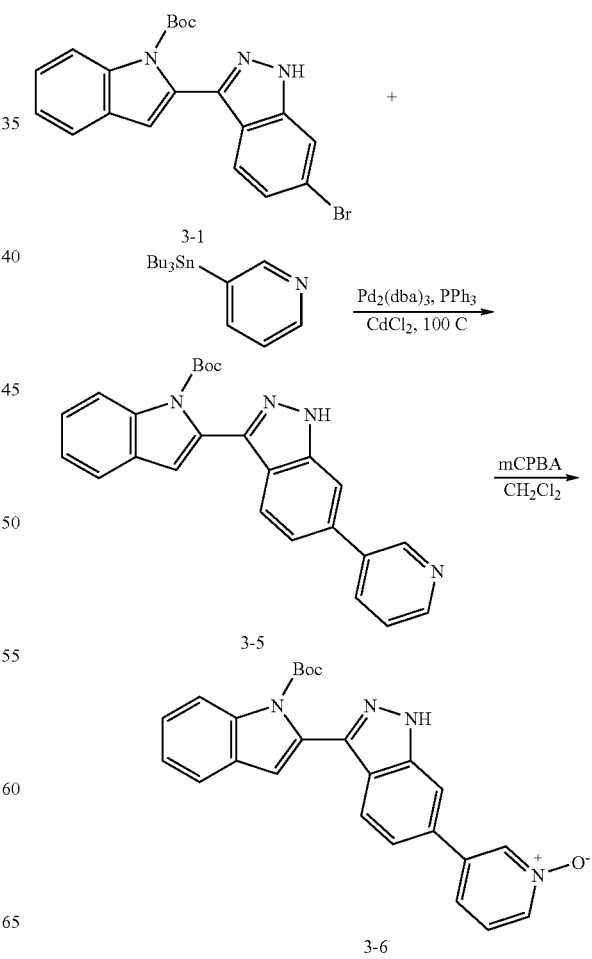

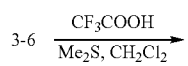

-continued

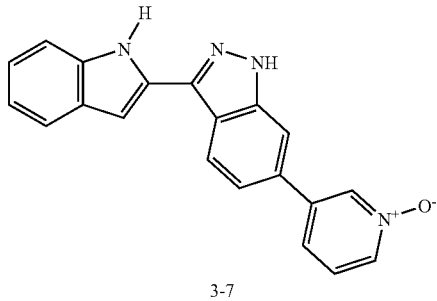

3-(1H-Indol-2-yl)-6-(1-oxy-pyridin-3-yl)-1H-indazole (3-7).

A stirred solution of the pyridine (3-5) (prepared as described in Example 3, Step 1, but replacing 2-fluoro-4-tributylstannanylpyridine with 3-tributylstannanylpyridine) in dichloromethane was treated at 0° C. with m-chlorperbenzoic acid. After 1 h stirring, the reaction mixture was concentrated in vacuo, partitioned between ethyl acetate and water. The organic layer was washed with brine, separated, dried ($MgSO_4$) and concentrated in vacuo. The crude product was treated at the ambient temperature with 50% trifluoroacetic acid in dichloromethane in the presence of dimethylsulfide and water. After 1 h stirring, the reaction mixture was concentrated in vacuo, partitioned between ethyl acetate and saturated aqueous sodium bicarbonate. The organic layer was washed with brine, separated, dried ($MgSO_4$) and concentrated in vacuo. Chromatography (preparative HPLC) afforded the desired product (3-7); $^1H$ NMR (500 MHz, DMSO-$d_6$) δ 13.60 (bs, 1H), 11.60 (s, 1H), 8.69 (s, 1H), 8.32 (d, 1H, J=8.5 Hz), 8.26 (d, 1H, J=6.3 Hz), 7.46 (s, 1H), 7.78 (d, 1H, J=8.1 Hz), 7.61–7.58 (m, 2H), 7.54 (t, 1H, J=7.8 Hz), 7.47 (d, 1H, J=7.8 Hz), 7.18 (s, 1H), 7.12 (t, 1H, J=7.3 Hz), 7.03 (t, 1H, J=7.3 Hz).

Compounds in Table 3 were synthesized as shown in Schemes 3 and 3A.

TABLE 3

| # | Structure | Nomenclature & $^1H$ NMR |
|---|---|---|
| 3-8 | 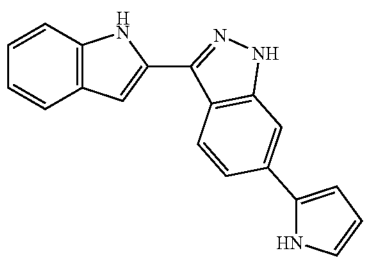 | 3-(1H-Indol-2-yl)-6-(1H-pyrrol-2-yl)-1H-indazole; $^1H$ NMR(300 MHz, DMSO-$d_6$) δ 13.26(s, 1H), 11.57(s, 1H), 11.48(s, 1H), 8.13(d, 1H, J=8.7Hz), 7.76(s, 1H), 7.58(s, 1H), 7.58(t, 1H, J=8.6Hz), 7.45 (d, 1H, J=8.1Hz), 7.15–7.07(m, 2H), 7.01(t, 1H, J=7.5Hz), 6.91(m, 1H), 6.65(m, 1H), 6.16(dd, 1H, J=5.1, 2.4Hz). |
| 3-9 | 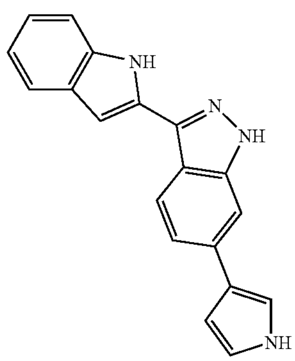 | 3-(1H-Indol-2-yl)-6-(1H-pyrrol-3-yl)-1H-indazole; $^1H$ NMR(300 MHz, DMSO-$d_6$) δ 13.10(s, 1H), 11.54(s, 1H), 11.01(s, 1H), 8.07(d, 1H, J=8.4Hz), 7.61(s, 1H), 7.59(d, 1H, J=8.7Hz), 7.49(dd, 1H, J=8.4, 1.0Hz), 7.45(d, 1H, J=8.1Hz), 7.36 (m, 1H), 7.15–7.06(m, 2H), 7.01(dt, 1H, J=7.2, 1.2Hz), 6.85(dd, 1H, J=4.5, 2.4 Hz), 6.56(dd, 1H, J=3.9, 2.1Hz). |
| 3-10 | 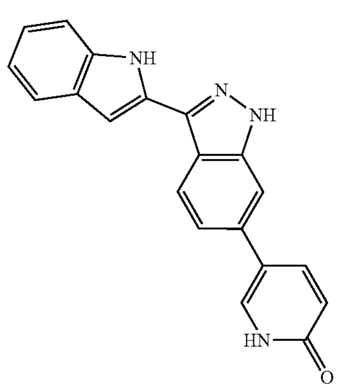 | 5-[3-(1H-Indol-2-yl)-1H-indazol-6-yl]-1H-pyridin-2-one; $^1H$ NMR(500 MHz, DMSO-$d_6$) δ 13.5(bs, 1H), 11.7(bs, 1H), 11.6(s, 1H), 8.28(d, 1H, J=8.6Hz), 7.95 (dd, 1H, J=2.7, 9.5Hz), 7.84,(d, 1H, J=2.4Hz), 7.69(s, 1H), 7.59(d, 1H, J=7.5 Hz), 7.44(m, 2H), 7.12(t, 2H, J=7.3 Hz), 7.01(t, 1H, J=7.3Hz), 6.48(d, 1H, J=9.5Hz). |

TABLE 3-continued

| # | Structure | Nomenclature & $^1$H NMR |
|---|---|---|
| 3-11 | 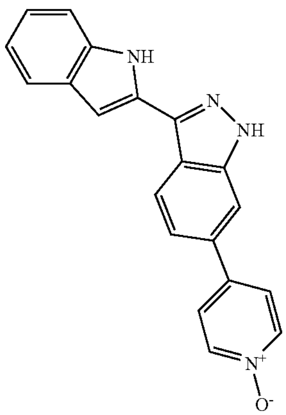 | 3-(1H-Indol-2-yl)-6-(1-oxy-pyridin-4-yl)-1H-indazole; $^1$H NMR(300 MHz, DMSO-d$_6$) δ 13.54(s, 1H), 11.63(s, 1H), 8.33(d, 1H, J=7.5Hz), 8.31(s, 2H, J=7.8Hz), 7.95(s, 1H), 7.93(d, 1H, J=7.5Hz), 7.65(dd, 1H, J=8.4, 1.5Hz), 7.61(d, 1H, J=7.8Hz), 7.46(d, 1H, J=8.1Hz), 7.18(d, 1H, J=0.9Hz), 7.13(dt, 1H, J=7.5 0.9Hz), 7.18(dt, 1H, J=7.5, 0.9Hz). |
| 3-12 | 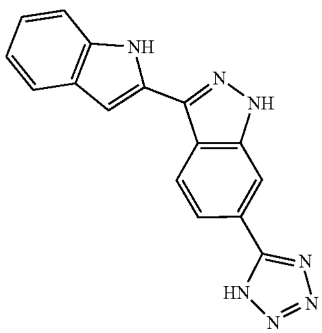 | 3-(1H-Indol-2-yl)-6-(1H-tetrazol-5-yl)-1H-indazole; $^1$H NMR(300 MHz, DMSO-d$_6$) δ 13.72(s, 1H), 11.67(s, 1H), 8.45(d, 1H, J=8.7Hz), 8.30(s, 1H), 7.93(dd, 1H, J=8.7, 1.2Hz), 1.62(d, 1H, J=7.5Hz), 7.47(d, 1H, J=8.4Hz), 7.22(s, 1H), 7.14(dt, 1H, J=8.4, 1.2Hz), 7.03(dt, 1H, J=7.4, 1.2Hz). |

In addition to compounds in Table 3, additional compounds in Table 3A are synthesized as shown in Schemes 3 and 3A.

TABLE 3A

| # | Structure | Nomenclature |
|---|---|---|
| 3-13 | 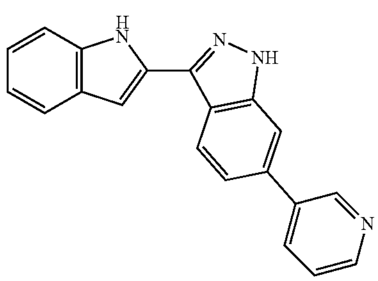 | 3-(1H-Indol-2-yl)-6-pyridin-3-yl-1H-indazole |
| 3-14 | 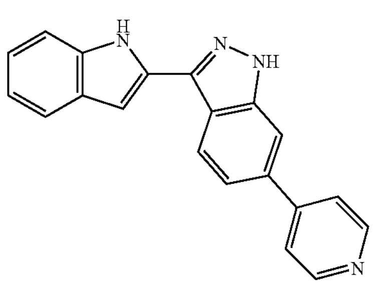 | 3-(1H-Indol-2-yl)-6-pyridin-4-yl-1H-indazole |

TABLE 3A-continued
| # | Structure | Nomenclature |
|---|---|---|
| 3-15 | 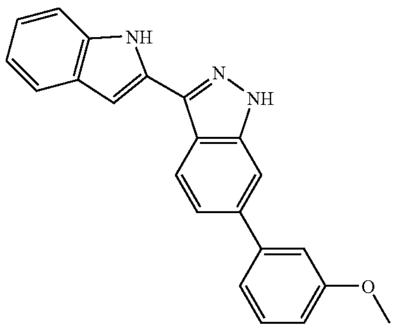 | 3-(1H-Indol-2-yl)-6-(3-methoxy-phenyl)-1H-indazole |
| 3-16 | 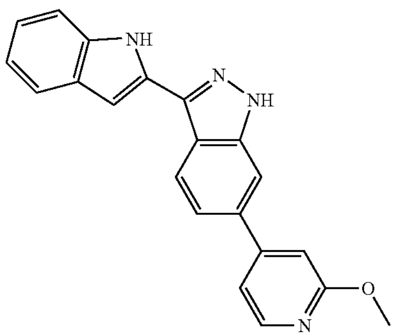 | 3-(1H-Indol-2-yl)-6-(2-methoxy-pyridin-4-yl)-1H-indazole |
| 3-17 | 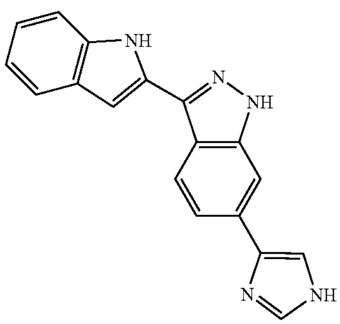 | 6-(1H-Imidazol-4-yl)-3-(1H-indol-2-yl)-1H-indazole |
| 3-18 | 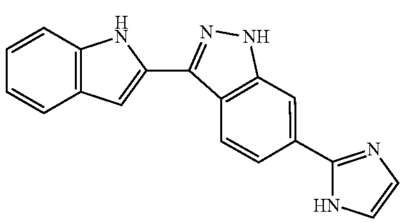 | 6-(1H-Imidazol-2-yl)-3-(1H-indol-2-yl)-1H-indazole |
Example 4
Scheme 4
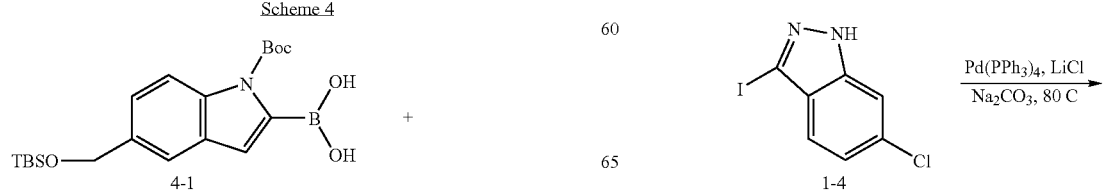

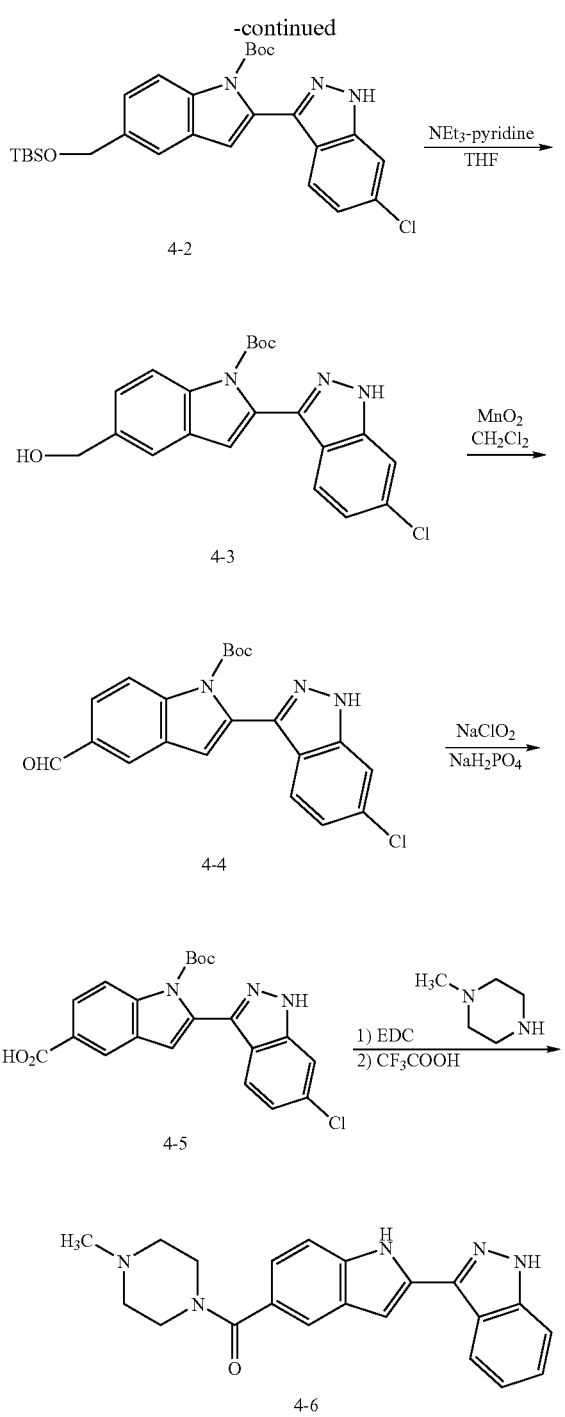

concentrated in vacuo. Chromatography (SiO$_2$, 33% ethyl acetate in hexanes) followed by concentration afforded 4-2 as a pale brown solid. The intermediate, 4-2, was dissolved in dichloromethane (6 mL) and treated at the ambient temperature with triethylammonium fluoride (1.74 g, 10.77 mmol). After 3 h stirring, the reaction mixture was concentrated in vacuo and partitioned between ethyl acetate and saturated aqueous sodium bicarbonate solution. The organic layer was separated, dried (MgSO$_4$), and concentrated in vacuo. Chromatography (SiO$_2$, 33% ethyl acetate in hexanes) followed by concentration afforded 4-3 as a pale brown solid.; MS (M+1)=398.

Step 2: 2-(6-Chloro-1H-indazol-3-yl)-indole-1,5-dicarboxylic acid 1-tert-butyl ester (4-5)

A solution of the alcohol 4-3 (210 mg, 0.528 mmol) in dichloromethane was treated with manganese dioxide (229 mg, 2.64 mmol) and heated to reflux where it remained for 1 h. Five additional equivalents of manganese dioxide were added and the reaction was maintained at reflux for 1 h. The excess manganese dioxide was filtered through Celite and the filter cake was washed with ethyl acetate (40 ml) and methanol (40 ml). The filtrate was concentrated in vacuo to a brown oil (4-4). A solution of the tert-butyl 5-formyl-2-(1H-indazol-3-yl)-1H-indole-1-carboxylate (4-4, 1.2 g, 3.3 mmol), 2-methyl-2-butene (19.9 ml, 188.2 mmol), a 1.9M solution of sodium phosphate monobasic (1.73 ml, 6.6 mmol), and sodium chlorite (597.3 mg, 6.60 mmol) were stirred in t-Butanol for 1 h. 3 additional equivalents of both solid sodium phosphate monobasic and sodium chlorite were added to the reaction over a 3 h period, and the reaction was mixed for 24 h. The t-Butanol was removed in vacuo and the residual yellow solid was dissolved in ethyl acetate (150 ml) and washed twice with a 98:2 mixture of 10% sodium bisulfite:10% potassium bisulfate (2×75 ml). The combined organics were dried over Na$_2$SO$_4$, filtered and concentrated in vacuo to afford 1-(tert-butoxycarbonyl)-2-(1H-indazol-3-yl)-1H-indole-5-carboxylic acid (4-5); $^1$H NMR(500 MHz, CDCl$_3$) δ 8.47 (s, 1H), 8.40 (d, 1H, J=8.8 Hz), 8.17 (d, 1H, J=8.8 Hz), 7.68 (d, 1H, J=8.1 Hz), 7.56 (d, 1H, J=8.3 Hz), 7.46 (t, 1H, J=8.3 Hz), 7.23 (t, 1H, J=7.8 Hz), 6.99 (s, 1H), 1.14 (s, 3H).

Step 3: 3-{5-[(4-methylpiperazin-1-yl)carbonyl]-1H-indol-2-yl}-1H-indazole (3-6a).

A solution of 1-(tert-butoxycarbonyl)-2-(1H-indazol-3-yl)-1H-indole-5-carboxylic acid (4-5, 100 mg, 0.265 mmol), N-methyl piperazine (40 µL, 0.32 mmol), EDC (61 mg, 0.32 mmol), and HOAt (43.3 mg, 0.32 mmol)in 5 ml of DMF was treated with triethylamine (90 µL, 0.66 mmol) and mixed for 24 h. The solution was partitioned between ethyl acetate (3×50 mL) and water (75 mL). The combined organics were dried over Na$_2$SO$_4$, filtered and concentrated. The residual oil was dissolved in a 1:1 mixture of dichloromethane/trifluoroacetic acid and mixed for 45 min. The solvent was removed in vacuo and the residue was purified by reverse phase liquid chromatography (H$_2$O/CH$_3$CN gradient with 0.1% 1TFA present) to provide 3-{5-[(4-methylpiperazin-1-yl)carbonyl]-1H-indol-2-yl}-1H-indazole (4-6); $^1$H NMR (500 MHz, CD$_3$OD) δ 11.36 (s, 1H), 8.14 (d, 1H, J=8.3 Hz), 7.83 (s, 1H), 7.58 (dd, 2H, J=8.5 Hz), 7.45 (t, 1H, J=8.3 Hz), 7.30 (dd, 2H, J=8.06 Hz), 7.17 (s, 1H), 4.55 (bs, 2H), 3.45 (bs, 2H), 3.25 (bs, 2H), 2.98 (s, 3H).

Step 1: 2-(6-Chloro-1H-indazol-3-yl)-5-(isopropyl-dimethyl-silanyloxymethyl)-indole-1-carboxylic acid tert-butyl ester (4-3).

A biphasic reaction mixture of the iodide (1-4b, 1 g, 3.59 mmol), the boronic acid (4-1, 2.47 g, 6.10 mmol), tetrakis(triphenylphosphine)palladium(0) (208 mg, 0.18 mmol), lithium chloride (457 mg, 10.8 mmol), and Na$_2$CO$_3$ (2M, 9 mL) in dioxane (27 mL) was heated at 80° C. for 2 h under the nitrogen atmosphere. The reaction mixture was partitioned between ethyl acetate and water. The organic layer was washed with brine, separated, dried (MgSO$_4$) and Compounds in Table 5 were synthesized as shown in Scheme 4.

TABLE 5

| # | Structure | Nomenclature & ¹H NMR |
|---|---|---|
| 4-7 | 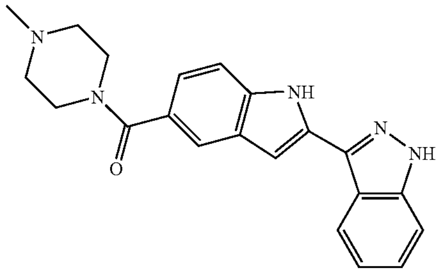 | 1-[2-(1H-Indazol-3-yl)-1H-indol-5-yl]-1-(4-methyl-piperazin-1-yl)-methanone; ¹H NMR(500 MHz, CD$_3$OD) δ 11.36 (s, 1H), 8.14(d, 1H, J=8.3Hz), 7.83 (s, 1H), 7.59(d, 1H, J=8.6Hz), 7.56 (d, 1H, J=8.6Hz), 7.46(t, 1H, J=8.3Hz), 7.31–7.27(m, 2H), 7.17(s, 1H), 4.55(bs, 2H), 3.43(bs, 4H), 3.22 (bs, 2H), 2.98(s, 3H). |
| 4-8 | 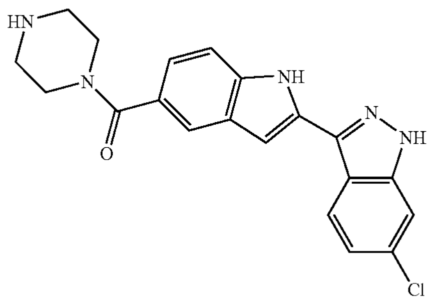 | 1-[2-(6-Chloro-1H-indazol-3-yl)-1H-indol-5-yl]-1-piperazin-1-yl-methanone; ¹H NMR(500 MHz, CD$_3$OD) δ 11.41(s, 1H), 8.12(d, 1H, J=8.5Hz), 7.83(d, 1H, J=0.74Hz), 7.61(d, 1H, J=1.2Hz), 7.56(d, 1H, J=8.3Hz), 7.30(dd, 1H, J=8.3, 1.5 Hz), 7.26(dd, 1H, J=8.5, 1.7Hz), 7.17(s, 1H), 3.93(m, 4H), 3.31(m, 4H). |
| 4-9 | 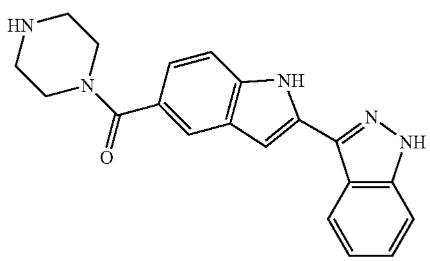 | 1-[2-(1H-Indazol-3-yl)-1H-indol-5-yl]-1-piperazin-1-yl-methanone; ¹H NMR (500 MHz, CD$_3$OD) δ 11.34(s, 1H), 8.14(d, 1H, J=8.3Hz), 7.83(d, 1H, J=0.7Hz), 7.58(d, 1H, J=8.3Hz), 7.56(d, 1H, J=8.3Hz), 7.45(dt, 1H, J=7.7, 1.1Hz), 7.31–7.26(m, 2H), 7.17(s, 1H), 3.94(m, 4 H), 3.32(m, 4H). |

In addition to compounds in Table 5, additional compounds in Table 6 are synthesized as shown in Scheme 4.

TABLE 6

| # | Structure | Nomenclature |
|---|---|---|
| 4-10 | 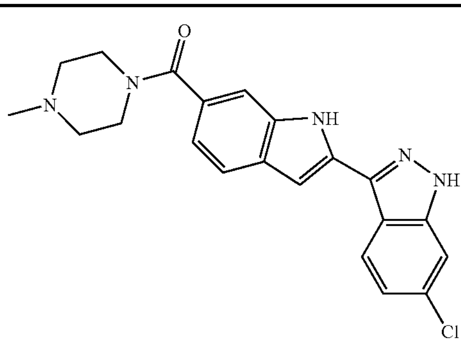 | 1-[2-(6-Chloro-1H-indazol-3-yl)-1H-indol-6-yl]-1-(4-methyl-piperazin-1-yl)-methanone |

TABLE 6-continued
| # | Structure | Nomenclature |
|---|---|---|
| 4-11 | 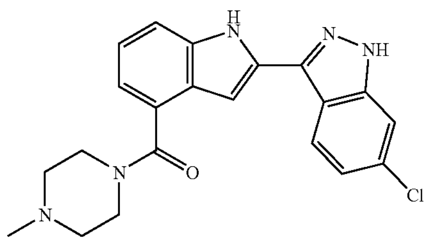 | 1-[2-(6-Chloro-1H-indazol-3-yl)-1H-indol-4-yl]-1-(4-methyl-piperazin-1-yl)-methanone |
| 4-12 | 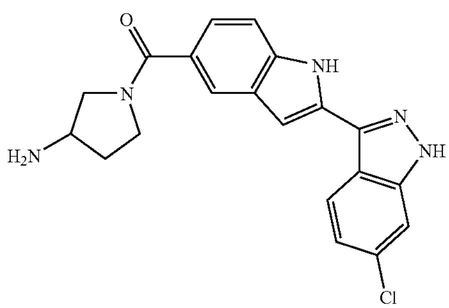 | 1-(3-Amino-pyrrolidin-1-yl)-1-[2-(6-chloro-1H-indazol-3-yl)-1H-indol-5-yl]-methanone |
| 4-13 | 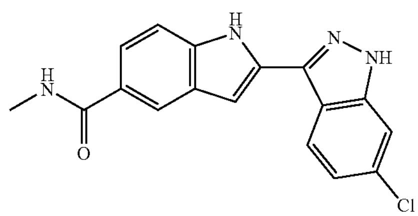 | 2-(6-Chloro-1H-indazol-3-yl)-1H-indole-5-carboxylic acid methylamide |
Example 5
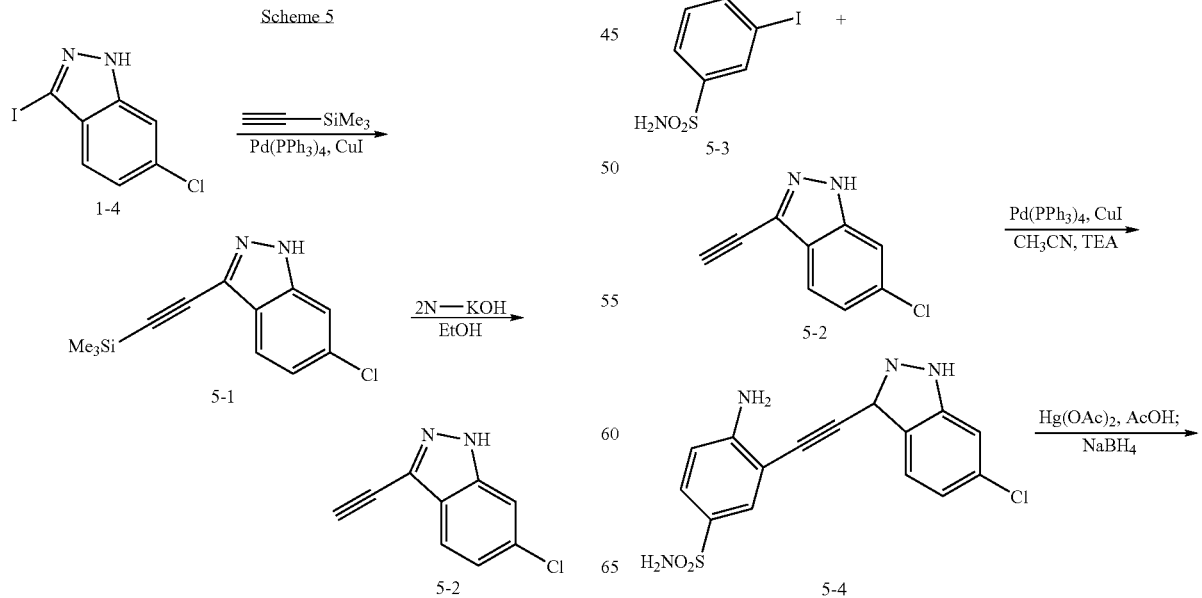

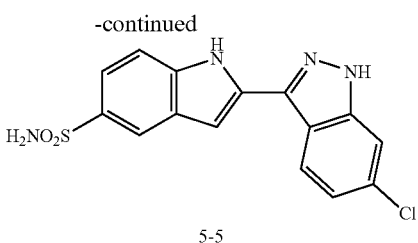

5-5

Step 1: 6-Chloro-3-ethynyl-1H-indazole (5-2)

A 12-inch pressure tube was charged with 6-Chloro-3-ethynyl-1H-indazole (1-4b, 4.0 g, 14.4 mmol), tetrakis(triphenylphosphine)palladium(0) (500 mg, 0.43 mmol), and cuprous iodide (82 mg, 0.43 mmol). The solids were dissolved/suspended in acetonitrile (10 mL) and triethylamine (10 mL, 71.8 mmol) followed by bubbling with nitrogen to degas the mixture. The trimethylsilyl acetylene (2.44 mL, 17.2 mmol) was added via pipette and the vessel was sealed before heated in an oil bath to 80° C. The reaction tube was cooled to ambient temperature after 2 h and partitioned between ethyl acetate and water. The layers were separated and the aqueous was extracted twice with ethyl acetate. The organics were combined, washed with brine, dried over magnesium sulfate, vacuum filtered, and concentrated in vacuo to afford the crude product as a black oil. The oil was dissolved in ethanol (50 mL) and 2M-KOH solution (30 mL). The deprotection was completion after 4 h at ambient temperature. The reaction mixture was concentrated in vacuo and partitioned between ethyl acetate and water. The layers were separated and the aqueous was extracted several times with ethyl acetate. The organics were combined, washed with brine, dried over sodium sulfate, vacuum filtered, and concentrated in vacuo to afford the crude product as a brown oil. This residue was purified by flash chromatography in hexanes/ethyl acetate gradients to give 5-2 as a yellow-orange powder.; $^1$H NMR (300 MHz, DMSO-$d_6$) δ 13.57 (bs, 1H), 7.74 (d, 1H, J=8.4 Hz), 7.70 (d, 1H, J=1.8 Hz), 7.24 (dd, 1H, J=8.7, 1.5 Hz), 4.57 (s, 1H).

Step 2: 4-Amino-3-(6-chloro-1H-indazol-3-ylethynyl)-benzenesulfonamide (5-4).

A mixture of the alkyne (5-2, 300 mg, 1.01 mmol), the iodide (5-3, 300 mg, 1.01 mmol), tetrakis(triphenylphosphine)palladiun(0) (35 mg, 0.03 mmol), cuprous iodide (6 mg, 0.03 mmol) in acetonitrile (1.4 mL) and triethylamine (0.7 mL) in a thick-walled tube was heated at 80° C. for 5 h. The reaction mixture was cooled to the ambient temperature and the resulting precipitates (5-4) were collected by filtration as a light tan solid; $^1$H NMR (300 MHz, DMSO-$d_6$) δ 13.64 (s, 1H), 7.94 (d, 1H, J=8.4 Hz), 7.76 (d, 1H, J=2.1 Hz), 7.71 (d, 1H, J=1.5 Hz), 7.53 (dd, 1H, J=8.7, 2.1 Hz), 7.26 (dd, 1H, J=8.4, 1.5 Hz), 7.08 (bs, 2H), 6.84 (d, 1H, J=8.4 Hz), 6.27 (bs, 2H).

Step 3: 2-(6-Chloro-1H-indazol-3-yl)-1H-indole-5-sulfonic acid amide (5-5).

The alkyne (5-4, 56 mg, 0.161 mmol) was dissolved in acetic acid (8 mL) and treated with mercuric acetate (77 mg, 0.24 mmol). After 2 h stirring, the reaction mixture was concentrated in vacuo, suspended in saturated aqueous sodium bicarbonate and treated with sodium borohydride. After 10 min stirring, the mixture was extracted with ethyl acetate. The organic layer was washed with brine, separated, dried (MgSO$_4$) and concentrated in vacuo. Chromatography (SiO$_2$, 50% ethyl acetate in hexanes) afforded the desired product (5-5); $^1$H NMR (300 MHz, DMSO-$d_6$) δ 13.58 (s, 1H), 12.09 (s, 1H), 8.26 (d, 1H, J=8.7 Hz), 8.11 (s, 1H), 7.72 (d, 1H, J=1.5 Hz), 7.61 (dd, 1H, J=8.7, 1.8 Hz), 7.55 (d, 1H, J=8.4 Hz), 7.36 (d, 1H, J=1.5 Hz), 7.30 (dd, 1H, J=8.7, 1.8 Hz), 7.16 (s, 2H).

Compounds in Table 7 were synthesized as shown in Scheme 5.

TABLE 7

| # | Structure | Nomenclature |
|---|---|---|
| 5-6 | 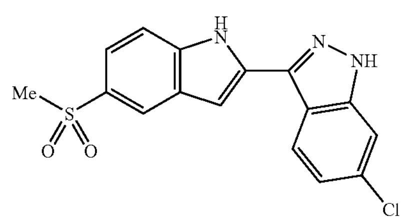 | Methyl [2-(6-chloro-1H-indazol-3-yl)-1H-indole-5-yl]sulfone; $^1$H NMR(300 MHz, DMSO-$d_6$) δ 13.63(s, 1H), 12.24(s, 1H), 8.25(d, 1H, J=8.7 Hz), 7.19(s, 1H), 7.73(d, 1H, J=1.5 Hz), 7.68–7.62(m, 2H), 7.40(d, 1H, J=1.8Hz), 7.32(dd, 1H, J=8.4, 1.8 Hz), 3.19(s, 3H) |
| 5-7 | 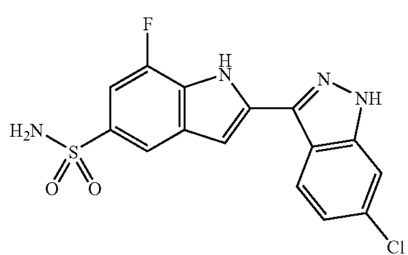 | 2-(6-Chloro-1H-indazol-3-yl)-7-fluoro-1H-indole-5-sulfonic acid amide; $^1$H NMR(300 MHz, DMSO-$d_6$) δ 13.66 (s, 1H), 12.61(d, 1H, J=1.2Hz), 8.23(d, 1H, J=8.7Hz), 7.96(d, 1H, J=1.2Hz), 7.73(d, 1H,J=1.2Hz), 7.44(dd, 1H, J=3.0, 2.1Hz), 7.39(dd, 1H, J=10.8, 1.2Hz), 7.31(dd, 1H, J=9.0, 1.8Hz), 7.30(s, 2H). |

TABLE 7-continued

| # | Structure | Nomenclature |
|---|---|---|
| 5-8 | 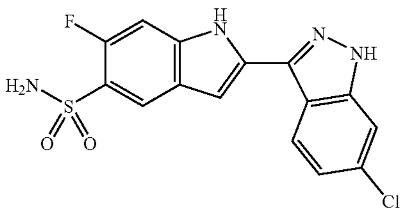 | 2-(6-Chloro-1H-indazol-3-yl)-6-fluoro-1H-indole-5-sulfonic acid amide; $^1$H NMR(300 MHz, DMSO-d$_6$) δ 13.59 (s, 1H), 12.14(s, 1H), 8.23(d, 1H, J=9.0Hz), 8.05(d, 1H, J=7.5Hz), 7.72(d, 1H, J=1.2Hz), 7.44(s, 2H), 7.37(d, 1H, J=1.2Hz), 7.32(m, 1H), 7.29(s, 1H). |
| 5-9 | 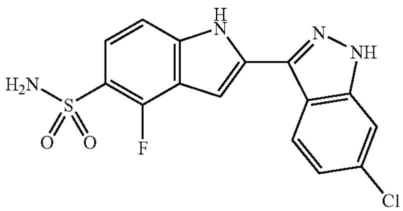 | 2-(6-Chloro-1H-indazol-3-yl)-4-fluoro-1H-indole-5-sulfonic acid amide; $^1$H NMR(300 MHZ, DMSO-d$_6$) δ 13.65(s, 1H), 12.35(s, 1H), 8.34(d, 1H, J=9.0Hz), 7.73(d, 1H, J=1.5Hz), 7.52(dd, 1H, J=8.4, 6.9 Hz), 7.46(s, 2H), 7.37(d, 1H, J=1.2 Hz), 7.29(dd, 1H, J=9.0, 1.8Hz). |
| 5-10 | 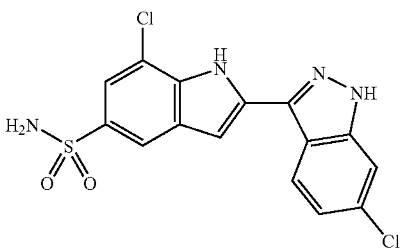 | 7-Chloro-2-(6-chloro-1H-indazol-3-yl)-1H-indole-5-sulfonic acid amide; $^1$H NMR(300 MHz, DMSO-d$_6$) δ 13.67(s, 1H), 12.32(s, 1H), 8.19(d, 1H, J=8.4Hz), 8.08(d, 1H, J=1.2 Hz), 7.74(d, 1H, J=1.5Hz), 7.65(d, 1H, J=1.5Hz), 7.44(d, 1H, J=1.8 Hz), 7.33–7.30(m, 3H). |
| 5-11 | 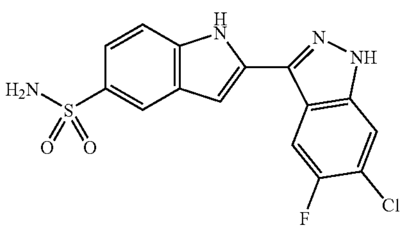 | 2-(6-Chloro-5-fluoro-1H-indazol-3-yl)-1H-indole-5-sulfonic acid amide; $^1$H NMR(500 MHz, DMSO-d$_6$) δ 13.70(s, 1H), 12.1(s, 1H), 8.29(d, 1H, J=9.5Hz), 8.09(d, 1H, J=1.5 Hz), 7.90(d, 1H, J=6.1Hz), 7.61 (dd, 1H, J=1.7, 8.5Hz), 7.55(d, 1H, J=8.5Hz), 7.41(d, 1H, J=1.5 Hz), 7.16(s, 2H). |
| 5-12 | 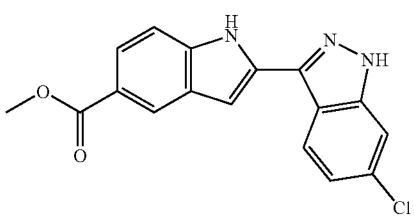 | 2-(6-Chloro-1H-indazol-3-yl)-1H-indole-5-carboxylic acid methyl ester; $^1$H NMR(300 MHz, DMSO-d$_6$) δ 13.55 (s, 1H), 12.45(s, 1H), 8.28(s, 1H), 8.25(d, 1H, J=8.4Hz), 7.86(d, 1H, J=8.7Hz), 7.72(d, 1H, J=1.8Hz), 7.49 (d, 1H, J=8.4Hz), 7.3–7.25(m, 2H), 3.75(s, 3H). |
| 5-13 | 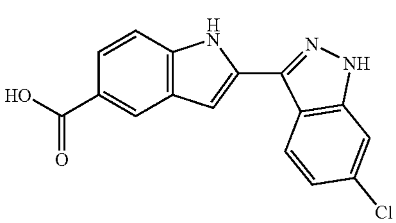 | 2-(6-chloro-1H-indazol-3-yl)-1H-indole-5-carboxylic acid; $^1$H NMR(300 MHz, DMSO-d$_6$) δ 13.55(s, 1H), 12.45(s, 1H), 12.02(s, 1H), 8.28(s, 1H), 8.25(d, 1H, J=8.4Hz), 7.75(dd, 1H, J=8.7, 1.5Hz), 7.72(d, 1H, J=1.8Hz), 7.49 (d, 1H, J=8.4Hz), 7.31(d, 1H, J=2.1 Hz), 7.29(dd, 1H, J=9.0, 1.8Hz). |
| 5-14 | 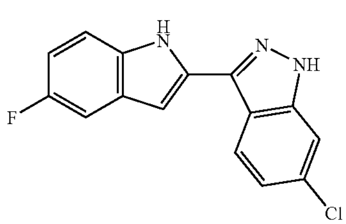 | 6-Chloro-3-(5-fluoro-1H-indol-2-yl)-1H-indazole; $^1$H NMR(400 MHz, DMSO-d$_6$) δ 13.48 (s, 1H), 11.72(s, 1H), 8.20 (d, 1H, J=8.3Hz), 7.50(s, 1H), 7.42 (dd, 1H, J=8.6, 4.3Hz), 7.33(dd, 1H, J=9.7, 2.5Hz), 7.29(d, 1H, J=8.0 Hz), 7.14(s, 1H), 6.97(dt, 1H, J=9.0, 2.5Hz). |

TABLE 7-continued

| # | Structure | Nomenclature |
|---|---|---|
| 5-15 | 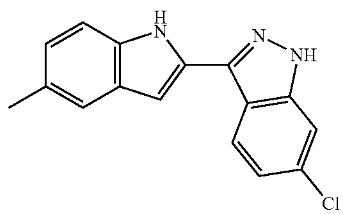 | 6-Chloro-3-(5-methyl-1H-indol-2-yl)-1H-indazole; $^1$H NMR(400 MHz, DMSO-d$_6$) δ 13.40(s, 1H), 11.43(s, 1H), 8.20(d, 1H, J=8.9Hz), 7.68(s, 1H), 7.37(s, 1H), 7.34(d, 1H, J=8.3Hz), 7.25(d, 1H, J=8.6Hz), 7.04(s, 1H), 6.95(d, 1H, J=8.3Hz), 2.39(s, 3H). |

In addition to compounds in Table 7, additional compounds in Table 8 are synthesized as shown in Scheme 5.

TABLE 8

| # | Structure | Nomenclature |
|---|---|---|
| 5-16 | 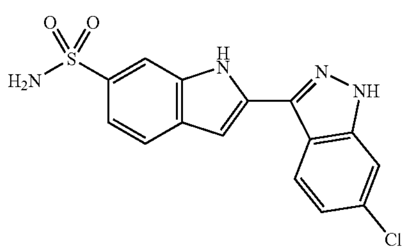 | 2-(6-Chloro-1H-indazol-3-yl)-1H-indole-6-sulfonic acid amide |
| 5-17 | 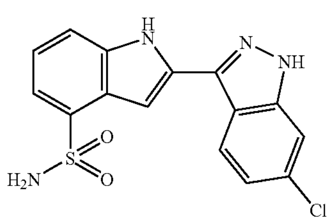 | 2-(6-Chloro-1H-indazol-3-yl)-1H-indole-4-sulfonic acid amide |
| 5-18 | 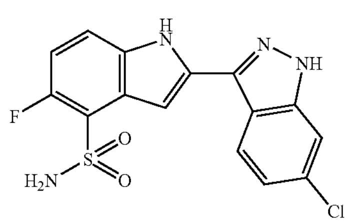 | 2-(6-Chloro-1H-indazol-3-yl)-5-fluoro-1H-indole-4-sulfonic acid amide |
| 5-19 | 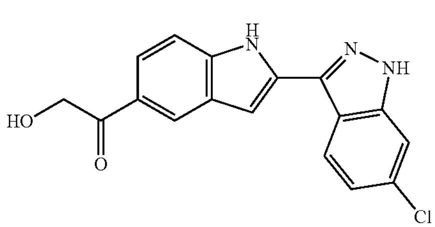 | 1-[2-(6-Chloro-1H-indazol-3-yl)-1H-indol-5-yl]-2-hyroxy-ethanone |

Example 6

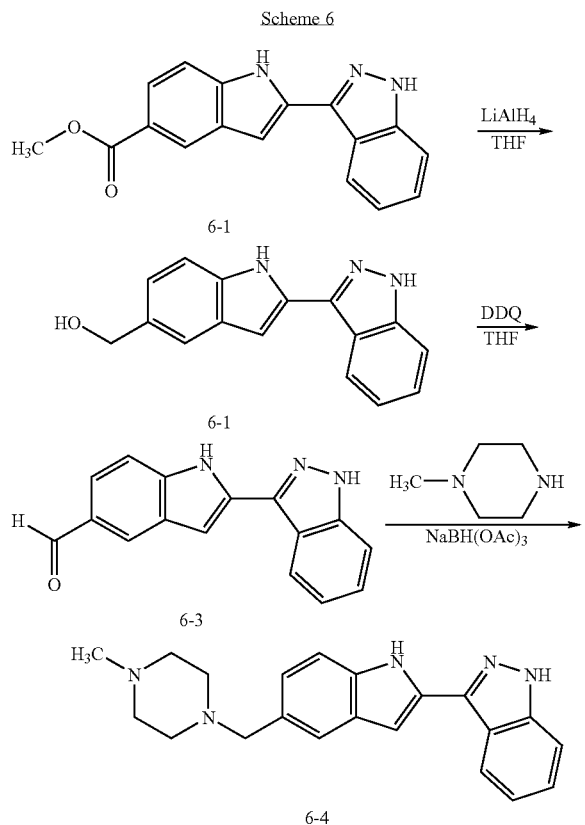

Step 1: [2-(1H-Indazol-3-yl)-1H-indol-5-yl]-methanol (6-2).

To a stirred solution of the methyl ester (6-1, 90 mg, 0.309 mmol) in tetrahydrofuran (3 mL) was added at −78° C. a solution of lithium aluminium hydride in toluene (1M, 0.62 mL, 0.62 mmol). The reaction mixture was stirred at the ambient temperature for 3 h, partitioned between ethyl acetate and 0.2N-hydrochloric acid. The organic layer was washed with brine, separated, dried ($MgSO_4$) and concentrated in vacuo. Chromatography ($SiO_2$, 60% ethyl acetate in hexanes) afforded the desired product (6-2) as a light tan solid; $^1$H NMR (400 MHz, DMSO-$d_6$) δ 13.28 (s, 1H), 11.49 (s, 1H), 8.19 (d, 1H, J=8.4 Hz), 7.60 (d, 1H, J=8.4 Hz), 7.53 (s, 1H), 7.44 (dt, 1H, J=7.6, 1.2 Hz), 7.39 (d, 1H, J=8.4 Hz), 7.25 (dt, 1H, J=8.0, 0.8 Hz), 7.10–7.08(m, 2H), 5.0 (t, 1H, J=5.6Hz), 4.56 (d, 2H, J=5.6 Hz).

Step 2: 2-(1H-Indazol-3-yl)-1H-indole-5-carbaldehyde (6-3).

To a stirred solution of the alcohol (6-2, 29 mg, 0.11 mmol) in tetrahydrofuran (2 mL) was added at the ambient temperature 2,3-dichloro-5,6-dicyano-1,4-benzoquinone (75 mg, 0.33 mmol). After 5 h stirring, the reaction mixture was partitioned between ethyl acetate and water. The organic layer was washed with brine, separated, dried ($MgSO_4$) and concentrated in vacuo. Chromatography ($SiO_2$, 50% ethyl acetate in hexanes) afforded the desired product (6-3) as a light tan solid; $^1$H NMR (400 MHz, DMSO-$d_6$) δ 13.42 (s, 1H), 11.14 (s, 1H), 9.98 (s, 1H), 8.22 (d, 1H, J=8.4 Hz), 8.20 (s, 1H), 7.70–7.56 (m, 3H), 7.46 (t, 1H, J=7.8 Hz), 7.36 (s, 1H), 7.28 (t, 1H, J=7.8 Hz).

Step 3: 3-[5-(4-Methyl-piperazin-1-ylmethyl)-1H-indol-2-yl]-1H-indazole (6-4).

A mixture of the aldehyde (6-3, 50 mg, 0.19 mmol), N-methylpiperazine (191 mg, 1.91 mmol), acetic acid (0.06 mL) and sodium triacetoxyborohydride (406 mg, 1.91 mmol) in N,N-dimethyl formamide (3 mL) was stirred at the ambient temperature for 11 h. The reaction mixture was partitioned between ethyl acetate and water. The organic layer was washed with brine, separated, dried ($MgSO_4$) and concentrated in vacuo. Chromatography ($SiO_2$, 30% methanol in ethyl acetate) afforded the desired product (6-4) as a light tan solid; $^1$H NMR (400 MHz, DMSO-$d_6$) δ 13.34 (s, 1H), 11.56 (s, 1H), 8.23 (d, 1H, J=8.0 Hz), 7.66 (d, 1H, J=8.4 Hz), 7.53 (s, 1H), 7.49 (t, 1H, J=7.6 Hz), 7.44 (d, 1H, J=8.4 Hz), 7.31 (t, 1H, J=7.6 Hz), 7.12–7.11 (m, 2H), 3.57 (s, 2H), 2.52–2.26 (m, 8H), 2.21 (s, 3H).

Compounds in Table 9 were synthesized as shown in Scheme 6.

TABLE 9

| # | Structure | Nomenclature & $^1$H-NMR |
|---|---|---|
| 6-5 | 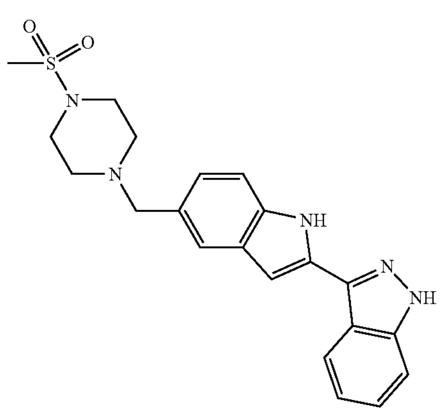 | 3-[5-(4-Methanesulfonyl-piperazin-1-ylmethyl)-1H-indol-2-yl]-1H-indazole; $^1$H NMR(300 MHz, DMSO-$d_6$) δ 13.31(s, 1H), 11.56(s, 1H), 8.18(d, 1H, J=8.1Hz), 7.61 (d, 1H, J=8.1Hz), 7.50(s, 1H), 7.45(d, 1H, J=6.9Hz), 7.40(d, 1H, 9.0Hz), 7.26(t, 1H, 7.5 Hz), 7.09(s, 1H), 7.08(m, 1H), 3.58 (s, 2H), 3.11(bs, 4H), 2.87(s, 3H), 2.50(m, 4H). |

TABLE 9-continued

| # | Structure | Nomenclature & $^1$H-NMR |
|---|---|---|
| 6-6 | 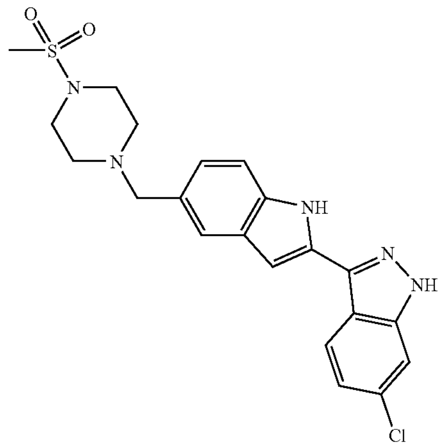 | 6-Chloro-3-[5-(4-methanesulfonyl-piperazin-1-ylmethyl)-1H-indol-2-yl]-1H-indazole; $^1$H NMR(300 MHz, DMSO-d$_6$) δ 13.45(s, 1H), 11.61(s, 1H), 8.21(d, 1H, J=8.7Hz), 7.69 (d, 1H, J=1.5Hz), 7.49(s, 1H), 7.40(d, 1H, J=8.7Hz), 7.27(dd, 1H, J=8.4, 1.8Hz), 7.11(s, 1H), 7.09 (dd, 1H, J=8.4, 1.2Hz), 3.58(s, 2H), 3.11(bs, 4H), 2.87(s, 3 H), 2.50 (m, 4H). |
| 6-7 | 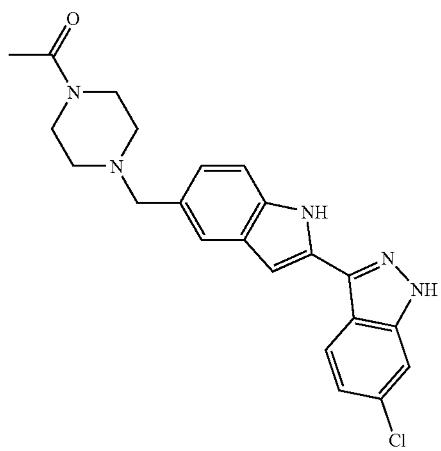 | 6-Chloro-3-[5-(4-acetyl-piperazin-1-ylmethyl)-1H-indol-2-yl]-1H-indazole; $^1$H NMR(300 MHz, DMSO-d$_6$) δ 13.45 (s, 1H), 11.60(s, 1H), 8.21(d, 1H, J= 8.7Hz), 7.69(d, 1H,J=1.2Hz), 7.49 (s, 1H), 7.40(d, 1H, J=8.1Hz), 7.26 (dd, 1H, J=8.4, 1.5Hz), 7.11(s, 1H), 7.09(m, 1H), 3.55(s, 2H), 3.42(m, 4H), 2.38(t, 2H, J=4.8Hz), 3.32(t, 2H, J=4.8Hz), 1.97(s, 3H). |
| 6-8 | 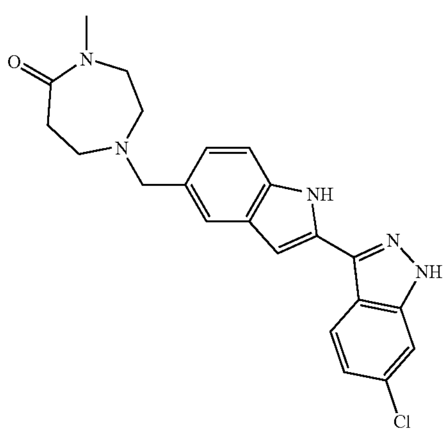 | 1-[2-(6-Chloro-1H-indazol-3-yl)-1H-indol-5-ylmethyl]-4-methyl-[1,4]diazepan-5-one; $^1$H NMR(300 MHz, DMSO-d$_6$) δ 13.45(s, 1H), 11.60 (s, 1H), 8.21(d, 1H, J=8.7Hz), 7.69 (d, 1H, J=1.2Hz), 7.48(s, 1H), 7.40 (d, 1H, J=8.1Hz), 7.26(dd, 1H, J= 8.4, 1.5Hz), 7.10(s, 1H), 7.06(m, 1H), 3.62(s, 2 H), 3.43(m, 2 H), 2.83(s, 3H), 2.60–2.44(m, 6H). |

TABLE 9-continued

| # | Structure | Nomenclature & ¹H-NMR |
|---|---|---|
| 6-9 | 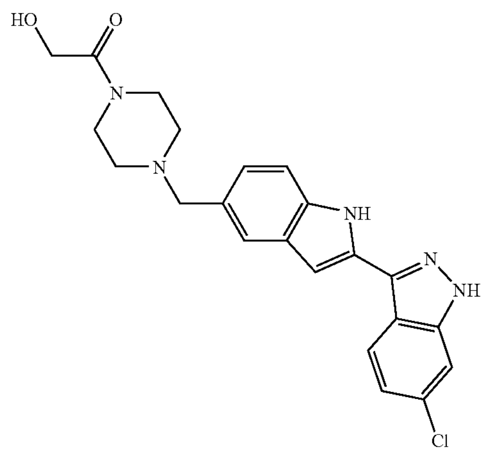 | 1-{4-[2-(6-Chloro-1H-indazol-3-yl)-1H-indol-5-ylmethyl]-pipetazin-1-yl}-2-hydroxy-ethanone; ¹H NMR(300 MHz, DMSO-d₆) δ 13.47(s, 1H), 11.60(s, 1H), 8.21(d, 1H, J=8.7Hz), 7.69(d, 1H, J=1.5Hz), 7.49(s, 1H), 7.39(d, 1H, J=8.1Hz), 7.26(dd, 1H, J=8.7, 1.8Hz), 7.11(s, 1H), 7.09(m, 1H), 4.53(t, 1H, J=5.7Hz), 4.06(d, 2H, J=5.7Hz), 3.56(s, 2H), 3.47(bs, 2H), 3.33(bs, 2H), 2.37(bs, 4H). |
| 6-10 | 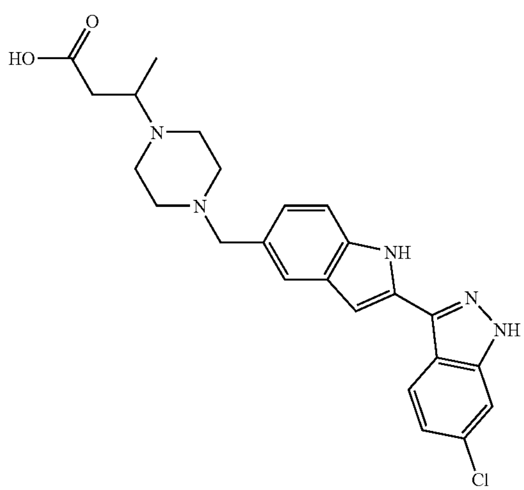 | 3-{4-[2-(6-Chloro-1H-indazol-3-yl)-1H-indol-5-ylmethyl]-piperazin-1-yl}-butyric acid; ¹H NMR(300 MHz, DMSO-d₆) δ 13.51(s, 1H), 11.69(br s, 1H), 8.22(d, 1H, J=9.0Hz), 7.70(d, 1H, J=1.8Hz), 7.58(brs, 1H), 7.43 (d, 1H, J=8.1Hz), 7.27(dd, 1H, J=8.7, 1.8Hz), 7.15(br s, 2H), 3.33(br s, 6H), 3.12(m, 1H), 2.67(brs, 4H), 2.47(m, 1H) 2.18(dd, 1H, J=15.6, 6.9Hz), 1.01(d, 3H, J=6.9Hz). |
| 6-11 | 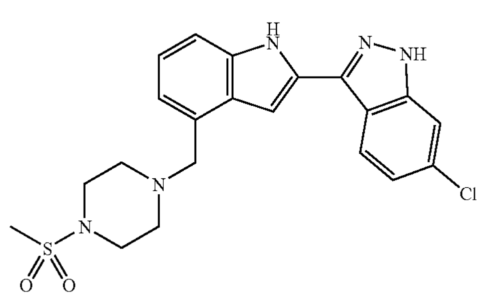 | 6-Chloro-3-[4-(4-methanesulfonyl-piperazin-1-ylmethyl)-1H-indol-2-yl]-1H-indazole; ¹H NMR(300 MHz, DMSO-d₆) δ 13.45(s, 1H), 11.64(s, 1H), 8.26(d, 1H, J=8.7Hz), 7.69(d, 1H, J=1.2Hz), 7.36(d, 1H, J=8.1 Hz), 7.29(dd, 1H, J=8.7, 1.5Hz), 7.27(s, 1H), 7.09(t, 1H, J=7.2Hz), 6.98(d, 1H, J=6.9Hz), 3.86(s, 2H), 3.13(m, 4H) 2.86(s, 3H), 2.58(m, 4H). |

TABLE 9-continued

| # | Structure | Nomenclature & $^1$H-NMR |
|---|---|---|
| 6-12 | 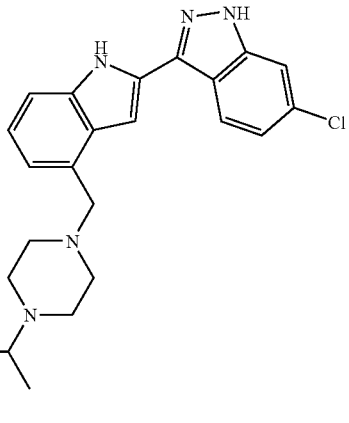 | 3-{4-[2-(6-Chloro-1H-indazol-3-yl)-1H-indol-4-ylmethyl]-piperazin-1-yl}-butyric acid; $^1$H NMR(300 MHz, DMSO-d $d_6$) δ 13.45(s, 1H), 11.64(s, 1H), 8.26(d, 1H, J=8.7) δ 13.56(s, 1H), 11.87(brs, 1H), 8.35(d, 1H, J=8.4Hz), 7.71(d, 1H, J=1.2Hz), 7.50 (br s, 2H), 7.31(dd, 1H, J=8.4, 1.2 Hz), 7.19(br s, 2H), 4.61(br s, 2H), 3.09(br s, 4H) 2.92(br s, 4H), 2.73–2.44(m, 2H), 2.21(m, 1H), 1.02(br s, 3H). |

In addition to compounds in Table 9, additional compounds in Table 10 are synthesized as shown in Scheme 6.

TABLE 10

| # | Structure | Nomenclature |
|---|---|---|
| 6-10 | 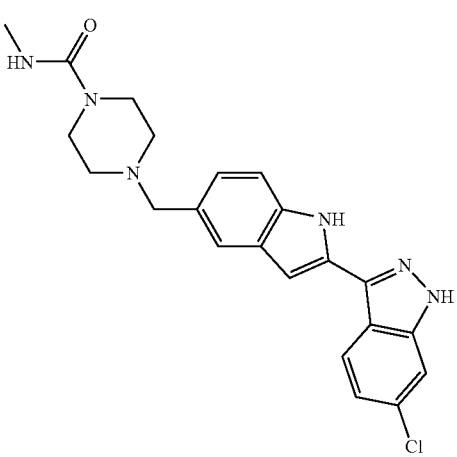 | 4-[2-(6-Chloro-1H-indazol-3-yl)-1H-indol-5-ylmethyl]-piperazine-1-carboxylic acid methylamide |
| 6-11 | 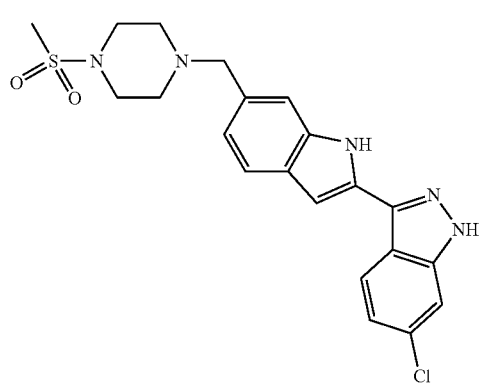 | 6-Chloro-3-[6-(4-methanesulfonyl-piperazin-1-ylmethyl)-1H-indol-2-yl]-1H-indazole |

TABLE 10-continued

| # | Structure | Nomenclature |
|---|---|---|
| 6-12 | 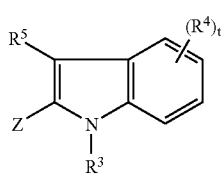 | 3-[5-(4-Methanesulfonyl-piperazin-1-ylmethyl)-1H-indol-2-yl]-1H-indazole-6-carbonitrile |
| 6-15 | 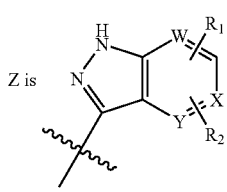 | 3-{4-[2-(6-Cyano-1H-indazol-3-yl)-1H-indol-5-ylmethyl]-piperazin-1-yl}-butyric acid |

What is claimed is:

1. A compound of Formula I

I or a pharmaceutically acceptable salt or stereoisomer thereof, wherein

Z is

W is N or C;
X=Y is C=N, N=C, or C=C;

a is 0 or 1;
b is 0 or 1;
m is 0, 1, or 2;
t is 1, 2, or 3;
$R^1$, $R^2$ and $R^5$ are independently selected from:
1) H,
2) $(C=O)_a O_b C_1$–$C_{10}$ alkyl,
3) $(C=O)_a O_b$ aryl,
4) $(C=O)_a O_b C_2$–$C_{10}$ alkenyl,
5) $(C=O)_a O_b C_2$–$C_{10}$ alkynyl,
6) $CO_2 H$,
7) halo,
8) OH,
9) $O_b C_1$–$C_6$ perfluoroalkyl,
10) $(C=O)_a NR^7 R^8$,
11) CN,
12) $(C=O)_a O_b C_3$–$C_8$ cycloalkyl,
13) $(C=O)_a O_b$ heterocyclyl,
14) $SO_2 NR^7 R^8$, and
15) $SO_2 C_1$–$C_{10}$ alkyl, said alkyl, aryl, alkenyl, alkynyl, cycloalkyl, and heterocyclyl is optionally substituted with one or more substituents selected from $R^6$;

R³ is selected from:
1) H,
2) (C=O)O_aC_1–C_6 alkyl,
3) (C=O)O_aaryl,
4) C_1–C_6 alkyl,
5) SO_2R^a, and
6) aryl;

R⁴ is selected from:
1) (C=O)_aO_bC_1–C_10 alkyl,
2) (C=O)_aO_baryl,
3) (C=O)_aO_bC_2–C_10 alkenyl,
4) (C=O)_aO_bC_2–C_10 alkynyl,
5) CO_2H,
6) halo,
7) OH,
8) O_bC_1–C_6 perfluoroalkyl,
9) (C=O)_aNR⁷R⁸,
10) CN,
11) (C=O)_aO_bC_3–C_8 cycloalkyl,
12) (C=O)_aO_bheterocyclyl,
13) SO_2NR⁷R⁸, and
14) SO_2C_1–C_10 alkyl, said alkyl, aryl, alkenyl, alkynyl, cycloalkyl, and heterocyclyl is optionally substituted with one or more substituents selected from R⁶;

R⁶ is:
1) (C=O)_aO_bC_1–C_10 alkyl,
2) (C=O)_aO_baryl,
3) C_2–C_10 alkenyl,
4) C_2–C_10 alkynyl,
5) (C=O)_aO_b heterocyclyl,
6) CO_2H,
7) halo,
8) CN,
9) OH,
10) O_bC_1–C_6 perfluoroalkyl,
11) O_a(C=O)_bNR⁷R⁸,
12) oxo,
13) CHO,
14) (N=O)R⁷R⁸, or
15) (C=O)_aO_bC_3–C_8 cycloalkyl, said alkyl, aryl, alkenyl, alkynyl, heterocyclyl, and cycloalkyl optionally substituted with one or more substituents selected from R^{6a};

R^{6a} is selected from:
1) (C=O)_rO_s(C_1–C_10)alkyl, wherein r and s are independently 0 or 1,
2) O_r(C_1–C_3)perfluoroalkyl, wherein r is 0 or 1,
3) (C_0–C_6)alkylene-S(O)_mR^a, wherein m is 0, 1, or 2,
4) oxo,
5) OH,
6) halo,
7) CN,
8) (C_2–C_10)alkenyl,
9) (C_2–C_10)alkynyl,
10) (C_3–C_6)cycloalkyl,
11) (C_0–C_6)alkylene-aryl,
12) (C_0–C_6)alkylene-heterocyclyl,
13) (C_0–C_6)alkylene-N(R^b)_2,
14) C(O)R^a,
15) (C_0–C_6)alkylene-CO_2R^a,
16) C(O)H,
17) (C_0–C_6)alkylene-CO_2H, and
18) C(O)N(R^b)_2, said alkyl, alkenyl, alkynyl, cycloalkyl, aryl, and heterocyclyl is optionally substituted with up to three substituents selected from R^b, OH, (C_1–C_6)alkoxy, halogen, CO_2H, CN, O(C=O)C_1–C_6 alkyl, oxo, and N(R^b)_2;

R⁷ and R⁸ are independently selected from:
1) H,
2) (C=O)O_bC_1–C_10 alkyl,
3) (C=O)O_bC_3–C_8 cycloalkyl,
4) (C=O)O_baryl,
5) (C=O)O_bheterocyclyl,
6) C_1–C_10 alkyl,
7) aryl,
8) C_2–C_10 alkenyl,
9) C_2–C_10 alkynyl,
10) heterocyclyl,
11) C_3–C_8 cycloalkyl,
12) SO_2R^a, and
13) (C=O)NR^b_2, said alkyl, cycloalkyl, aryl, heterocylyl, alkenyl, and alkynyl is optionally substituted with one or more substituents selected from R^{6a}, or R⁷ and R⁸ can be taken together with the nitrogen to which they are attached to form a monocyclic or bicyclic heterocycle with 5–7 members in each ring and optionally containing, in addition to the nitrogen, one or two additional heteroatoms selected from N, O and S, said monocylcic or bicyclic heterocycle optionally substituted with one or more substituents selected from R^{6a};

R^a is (C_1–C_6)alkyl, (C_3–C_6)cycloalkyl, aryl, or heterocyclyl; and

R^b is H, (C_1–C_6)alkyl, aryl, heterocyclyl, (C_3–C_6)cycloalkyl, (C=O)OC_1–C_6 alkyl, (C=O)C_1–C_6 alkyl or S(O)_2R^a.

2. The compound of claim 1, or a pharmaceutically acceptable salt or stereoisomer thereof, wherein

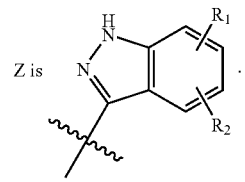

3. A compound of Formula I

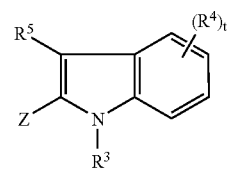

or a pharmaceutically acceptable salt or stereoisomer thereof, wherein

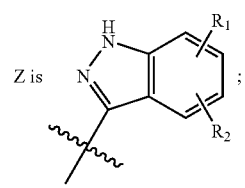

a is 0 or 1;
b is 0 or 1; and
t is 1 or 2;

R¹, R² and R⁵ are independently selected from:
1) H,
2) $(C=O)_aO_bC_1-C_6$ alkyl,
3) $(C=O)_aO_b$aryl,
4) $(C=O)_aO_bC_2-C_6$ alkenyl,
5) $(C=O)_aO_bC_2-C_6$ alkynyl,
6) $CO_2H$,
7) halo,
8) OH,
9) $O_bC_1-C_3$ perfluoroalkyl,
10) $(C=O)_aNR^7R^8$,
11) CN,
12) $(C=O)_aO_bC_3-C_6$ cycloalkyl,
13) $(C=O)_aO_b$heterocyclyl,
14) $SO_2NR^7R^8$, and
15) $SO_2C_1-C_6$ alkyl,
said alkyl, aryl, alkenyl, alkynyl, cycloalkyl, and heterocyclyl is optionally substituted with one or more substituents selected from $R^6$;

R⁴ is selected from:
1) $(C=O)_aO_bC_1-C_6$ alkyl,
2) $(C=O)_aO_b$aryl,
3) $(C=O)_aO_bC_2-C_6$ alkenyl,
4) $(C=O)_aO_bC_2-C_6$ alkynyl,
5) $CO_2H$,
6) halo,
7) OH,
8) $O_bC_1-C_3$ perfluoroalkyl,
9) $(C=O)_aNR^7R^8$,
10) CN,
11) $(C=O)_aO_bC_3-C_6$ cycloalkyl,
12) $(C=O)_aO_b$heterocyclyl,
13) $SO_2NR^7R^8$, and
14) $SO_2C_1-C_6$ alkyl,
said alkyl, aryl, alkenyl, alkynyl, cycloalkyl, and heterocyclyl is optionally substituted with one or more substituents selected from $R^6$;

$R^6$ is:
1) $(C=O)_aO_bC_1-C_6$ alkyl,
2) $(C=O)_aO_b$aryl,
3) $C_2-C_6$ alkenyl,
4) $C_2-C_6$ alkynyl,
5) $(C=O)_aO_b$ heterocyclyl,
6) $CO_2H$,
7) halo,
8) CN,
9) OH,
10) $O_bC_1-C_3$ perfluoroalkyl,
11) $O_a(C=O)_bNR^7R^8$,
12) oxo,
13) CHO,
14) $(N=O)R^7R^8$, or
15) $(C=O)_aO_bC_3-C_6$ cycloalkyl,
said alkyl, aryl, alkenyl, alkynyl, heterocyclyl, and cycloalkyl is optionally substituted with one or more substituents selected from $R^{6a}$;

$R^{6a}$ is selected from:
1) $(C=O)_rO_s(C_1-C_6)$alkyl, wherein r and s are independently 0 or 1,
2) $O_r(C_1-C_3)$perfluoroalkyl, wherein r is 0 or 1,
3) $(C_0-C_6)$alkylene-$S(O)_mR^a$, wherein m is 0, 1, or 2,
4) oxo,
5) OH,
6) halo,
7) CN,
8) $(C_2-C_6)$alkenyl,
9) $(C_2-C_6)$alkynyl,
10) $(C_3-C_6)$cycloalkyl,
11) $(C_0-C_6)$alkylene-aryl;
12) $(C_0-C_6)$alkylene-heterocyclyl,
13) $(C_0-C_6)$alkylene-$N(R^b)_2$,
14) $C(O)R^a$,
15) $(C_0-C_6)$alkylene-$CO_2R^a$,
16) $C(O)H$, and
17) $(C_0-C_6)$alkylene-$CO_2H$,
said alkyl, alkenyl, alkynyl, cycloalkyl, aryl, and heterocyclyl is optionally substituted with up to three substituents selected from $R^b$, OH, $(C_1-C_6)$alkoxy, halogen, $CO_2H$, CN, $O(C=O)C_1-C_6$ alkyl, oxo, and $N(R^b)_2$; and R⁷ and R⁸ are independently selected from:
1) H,
2) $(C=O)O_bC_1-C_6$ alkyl,
3) $(C=O)O_bC_3-C_6$ cycloalkyl,
4) $(C=O)O_b$aryl,
5) $(C=O)O_b$heterocyclyl,
6) $C_1-C_6$ alkyl,
7) aryl,
8) $C_2-C_6$ alkenyl,
9) $C_2-C_6$ alkynyl,
10) heterocyclyl,
11) $C_3-C_6$ cycloalkyl,
12) $SO_2R^a$, and
13) $(C=O)NR^b_2$,
said alkyl, cycloalkyl, aryl, heterocylyl, alkenyl, and alkynyl is optionally substituted with one or more substituents selected from R6ª, or R⁷ and R⁸ can be taken together with the nitrogen to which they are attached to form a monocyclic or bicyclic heterocycle with 5–7 members in each ring and optionally containing, in addition to the nitrogen, one or two additional heteroatoms selected from N, O and S, said monocylcic or bicyclic heterocycle optionally substituted with one or more substituents selected from $R^{6a}$;

$R^a$ is $(C_1-C_6)$alkyl, $(C_3-C_6)$cycloalkyl, aryl, or heterocyclyl; and $R^b$ is H, $(C_1-C_6)$alkyl, aryl, heterocyclyl, $(C_3-C_6)$cycloalkyl, $(C=O)OC_1-C_6$ alkyl, $(C=O)C_1-C_6$ alkyl or $S(O)_2R^a$.

4. The compound of claim 3, wherein R², R³, and R⁵ are H.

5. The compound of claim 4, wherein t is 1.

6. The compound of claim 5 wherein R⁴ is selected from:
1) $OC_1-C_6$ alkyleneNR⁷R⁸,
2) $(C=O)_aC_0-C_6$ alkylene-Q, wherein Q is H, OH, $CO_2H$, or $OC_1-C_6$ alkyl,
3) $OC_0-C_6$ alkylene-heterocyclyl, optionally substituted with one to three substituents selected from R6ª,
4) $C_0-C_6$ alkyleneNR⁷R⁸,
5) $(C=O)NR^7R^8$, and
6) $OC_1-C_3$ alkylene-$(C=O)NR^7R^8$.

7. A compound selected from:
6-Chloro-3-(1H-indol-2-yl)-1H-indazole
3-(1H-Indol-2-yl)-1H-indazole
3-(1H-Indol-2-yl)-1H-indazol-5-ylamine
3-(1H-Indol-2-yl)-6-methyl-1H-indazole
3-(1H-Indol-2-yl)-4-chloro-1H-indazole
3-(1H-Indol-2-yl)-7-chloro-1H-indazole 3-(1H-Indol-2-yl)-4-fluoro-1H-indazole
3-(1H-Indol-2-yl)-5-fluoro-1H-indazole
3-(1H-Indol-2-yl)-5-methyl-1H-indazole
3-(1H-Indol-2-yl)-6-trifluoromethyl-1H-indazole
3-(1H-Indol-2-yl)-5,6-dimethyl-1H-indazole
3-(1H-Indol-2-yl)-1H-indazole-6-sulfonic acid amide
3-(1H-indol-2-yl)-1H-indazole-5-sulfonamide
3-(1H-Indol-2-yl)-6-bromo-1H-indazole
3-(1H-Indol-2-yl)-1H-indazole-6-carbonitrile
3-[5-(piperazin-1-ylsulfonyl)-1H-indol-2-yl]-1H-indazole
6-(2-Fluoro-pyridin-4-yl)-3(1H-indol-2-yl)-1H-indazole
4-[3-(1H-Indol-2-yl)-1H-indazol-6-yl]-1H-pyridin-2-one
3-(1H-Indol-2-yl)-6-(1-oxy-pyridin-3-yl)-1H-indazole
3-(1H-Indol-2-yl)-6-(1H-pyrrol-2-yl)-1H-indazole
3-(1H-Indol-2-yl)-6-(1H-pyrrol-3-yl)-1H-indazole
5-[3-(1H-Indol-2-yl)-1H-indazol-6-yl]-1H-pyridin-2-one
3-(1H-Indol-2-yl)-6-(1-oxy-pyridin-4-yl)-1H-indazole
3-(1H-Indol-2-yl)-6-(1H-tetrazol-5-yl)-1H-indazole
3-{5-[(4-methylpiperazin-1-yl)carbonyl]-1H-indol-2-yl}-1H-indazole
1-[2-(1H-Indazol-3-yl)-1H-indol-5-yl]-1-(4-methyl-piperazin-1-yl)-methanone
1-[2-(6-Chloro-1H-indazol-3-yl)-1H-indol-5-yl]-1-piperazin-1-yl-methanone
1-[2-(1H-Indazol-3-yl)-1H-indol-5-yl]-1-piperazin-1-yl-methanone
2-(6-Chloro-1H-indazol-3-yl)-1H-indole-5-sulfonic acid amide
Methyl [2-(6-chloro-1H-indazol-3-yl)-1H-indole-5-yl] sulfone
2-(6-Chloro-1H-indazol-3-yl)-7-fluoro-1H-indole-5-sulfonic acid amide
2-(6-Chloro-1H-indazol-3-yl)-6-fluoro-1H-indole-5-sulfonic acid amide
2-(6-Chloro-1H-indazol-3-yl)-4-fluoro-1H-indole-5-sulfonic acid amide
7-Chloro-2-(6-chloro-1H-indazol-3-yl)-1H-indole-5-sulfonic acid amide
2-(6-Chloro-5-fluoro-1H-indazol-3-yl)-1H-indole-5-sulfonic acid amide
2-(6-Chloro-1H-indazol-3-yl)-1H-indole-5-carboxylic acid methyl ester
2-(6-chloro-1H-indazol-3-yl)-1H-indole-5-carboxylic acid
6-Chloro-3-(5-fluoro-1H-indol-2-yl)-1H-indazole
6-Chloro-3-(5-methyl-1H-indol-2-yl)-1H-indazole
3-[5-(4-Methyl-piperazin-1-ylmethyl)-1H-indol-2-yl]-1H-indazole
3-[5-(4-Methanesulfonyl-piperazin-1-ylmethyl)-1H-indol-2-yl]-1H-indazole
6-Chloro-3-[5-(4-methanesulfonyl-piperazin-1-ylmethyl)-1H-indol-2-yl]-1H-indazole
6-Chloro-3-[5-(4-acetyl-piperazin-1-ylmethyl)-1H-indol-2-yl]-1H-indazole
1-[2-(6-Chloro-1H-indazol-3-yl)-1H-indol-5-ylmethyl]-4-methyl-[1,4]diazepan-5-one
1-{4-[2-(6-Chloro-1H-indazol-3-yl)-1H-indol-5-ylmethyl]-piperazin-1-yl}-2-hydroxy-ethanone
3-{4-[2-(6-Chloro-1H-indazol-3yl)-1H-indol-5-ylmethyl]-piperazin-1-yl}-butyric acid
6-Chloro-3-[4-(4-methanesulfonyl-piperazin-1-ylmethyl)-1H-indol-2-yl]-1H-indazole
3-{4-[2-(6-Chloro-1H-indazol-3-yl)-1H-indol-4-ylmethyl]-piperazin-1-yl}-butyric acid
or a pharmaceutically acceptable salt thereof.

8. A compound according to claim 7 selected from:
2-(6-Chloro-1H-indazol-3-yl)-1H-indole-5-sulfonic acid amide

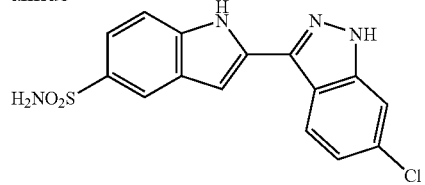

6-Chloro-3-[5-(4-acetyl-piperazin-1-ylmethyl)-1H-indol-2-yl]-1H-indazole

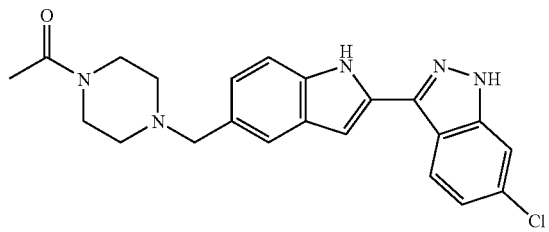

1-{(4-[2-(6-Chloro-1H-indazol-3-yl)-1H-indol-5-ylmethyl]-piperazin-1-yl}-2-hydroxy-ethanone

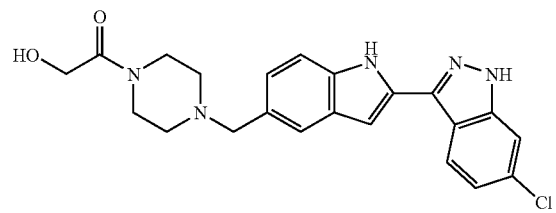

3-{4-[2-(6-Chloro-1H-indazol-3-yl)-1H-indol-5-ylmethyl]-piperazin-1-yl}-butyric acid

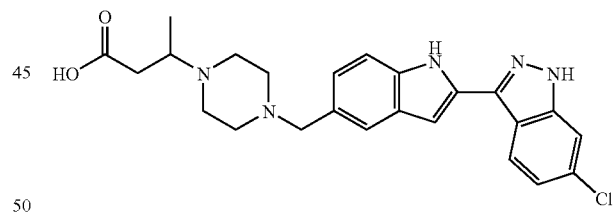

6-Chloro-3-[4-(4-methanesulfonyl-piperazin-1-ylmethyl)-1H-indol-2-yl]-1H-indazole

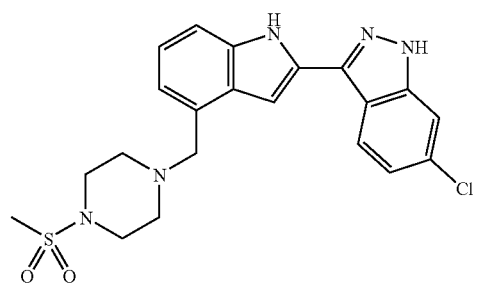

or a pharmaceutically acceptable salt thereof.

9. A pharmaceutical composition which is comprised of a compound in accordance with claim 1 and a pharmaceutically acceptable carrier.

10. A method of treating cancer in a mammal in need of such treatment which is comprised of administering to said mammal a therapeutically effective amount of a compound of claim 1 wherein the cancer is selected from cancers of the brain, genitourinary tract, lymphatic system, stomach, larynx and lung.

11. A method of treating cancer in a mammal in need of such treatment which is comprised of administering to said mammal a therapeutically effective amount of a compound of claim 1 wherein the cancer is selected from histiocytic lymphoma, lung adenocarcinoma, small cell lung cancers, pancreatic cancer, gioblastomas and breast carcinoma.

12. A method of treating cancer wherein is selected from cancers of the brain, genitourinary tract, lymphatic system, stomach, larynx, lung, histiocytic lymphoma, lung adenocarcinoma, small cell lung cancers, pancreatic cancer, gioblastomas and breast carcinoma which comprises administering a therapeutically effective amount of a compound of claim 1 in combination with a compound selected from:
 1) an estrogen receptor modulator,
 2) an androgen receptor modulator,
 3) retinoid receptor modulator,
 4) a cytotoxic agent,
 5) an antiproliferative agent,
 6) a prenyl-protein transferase inhibitor,
 7) an HMG-CoA reductase inhibitor,
 8) an HIV protease inhibitor,
 9) a reverse transcriptase inhibitor, and
 10) another angiogenesis inhibitor.

* * * * *